US012618070B2

(12) United States Patent
Edge et al.

(10) Patent No.: US 12,618,070 B2
(45) Date of Patent: May 5, 2026

(54) INCREASING ATOH1 LIFE TO DRIVE SENSORINEURAL HAIR CELL DIFFERENTIATION

(71) Applicant: Massachusetts Eye and Ear Infirmary, Boston, MA (US)

(72) Inventors: Albert Edge, Brookline, MA (US); Yen-Fu Cheng, Boston, MA (US); Judith Kempfle, Brookline, MA (US); Dunia Abdul-Aziz, Boston, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 981 days.

(21) Appl. No.: 17/686,734

(22) Filed: Mar. 4, 2022

(65) Prior Publication Data

US 2022/0259602 A1 Aug. 18, 2022

Related U.S. Application Data

(60) Division of application No. 16/358,579, filed on Mar. 19, 2019, now Pat. No. 11,286,487, which is a continuation of application No. 15/502,113, filed as application No. PCT/US2015/043976 on Aug. 6, 2015, now abandoned.

(60) Provisional application No. 62/034,459, filed on Aug. 7, 2014, provisional application No. 62/034,040, filed on Aug. 6, 2014.

(51) Int. Cl.

| | |
|---|---|
| *C07K 14/47* | (2006.01) |
| *A61K 9/00* | (2006.01) |
| *A61K 31/407* | (2006.01) |
| *A61K 31/69* | (2006.01) |
| *A61K 31/7105* | (2006.01) |
| *A61K 31/713* | (2006.01) |
| *A61K 38/05* | (2006.01) |
| *A61K 38/06* | (2006.01) |
| *A61K 38/07* | (2006.01) |
| *A61K 38/12* | (2006.01) |
| *A61K 38/15* | (2006.01) |
| *A61K 38/17* | (2006.01) |
| *A61K 45/06* | (2006.01) |
| *A61K 48/00* | (2006.01) |
| *C12N 15/00* | (2006.01) |
| *C12N 15/113* | (2010.01) |
| *A61K 38/00* | (2006.01) |

(52) U.S. Cl.
CPC ........ *C12N 15/1137* (2013.01); *A61K 9/0046* (2013.01); *A61K 31/407* (2013.01); *A61K 31/69* (2013.01); *A61K 31/7105* (2013.01); *A61K 31/713* (2013.01); *A61K 38/05* (2013.01); *A61K 38/06* (2013.01); *A61K 38/07* (2013.01); *A61K 38/12* (2013.01); *A61K 38/15* (2013.01); *A61K 38/1709* (2013.01); *A61K*

*45/06* (2013.01); *A61K 48/0075* (2013.01); *C07K 14/47* (2013.01); *C12N 15/113* (2013.01); *C12Y 603/02019* (2013.01); *A61K 38/00* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 4,522,811 A | | 6/1985 | Eppstein et al. |
| D309,535 S | | 7/1990 | Wilson |
| D360,535 S | | 7/1995 | Sjoberg |
| 5,695,995 A | * | 12/1997 | Weintraub ............. A61P 25/00 |
| | | | 435/360 |
| D447,031 S | | 8/2001 | Oh |
| 6,417,185 B1 | | 7/2002 | Goff et al. |
| 6,489,344 B1 | | 12/2002 | Nuss et al. |
| 6,608,063 B2 | | 8/2003 | Nuss et al. |
| 6,756,511 B2 | | 6/2004 | Castro Pineiro et al. |
| 6,890,956 B2 | | 5/2005 | Churcher et al. |
| 6,984,626 B2 | | 1/2006 | Nadin et al. |
| 7,049,296 B2 | | 5/2006 | Castro Pineiro et al. |
| 7,101,895 B2 | | 9/2006 | Churcher et al. |
| 7,138,400 B2 | | 11/2006 | Collins et al. |
| 7,144,910 B2 | | 12/2006 | Madin et al. |
| 7,183,303 B2 | | 2/2007 | Castro Pineiro et al. |
| 7,206,639 B2 | | 4/2007 | Jacobsen et al. |
| 7,399,633 B2 | | 7/2008 | Bernstein et al. |
| D646,625 S | | 10/2011 | Youn |
| 8,188,069 B2 | | 5/2012 | Miller et al. |
| 8,518,944 B2 | | 8/2013 | Subramanyam et al. |
| 8,617,810 B2 | | 12/2013 | Heller et al. |
| 8,673,634 B2 | | 3/2014 | Li et al. |
| 10,406,163 B2 | | 9/2019 | Edge et al. |

(Continued)

FOREIGN PATENT DOCUMENTS

| | | |
|---|---|---|
| CN | 1441841 | 9/2003 |
| GB | 2459910 | 11/2009 |

(Continued)

OTHER PUBLICATIONS

Forget et al (Dev Cell 29: 649-661, Jun. 23, 2014) (Year: 2014).*

(Continued)

*Primary Examiner* — Kimberly Ballard
*Assistant Examiner* — Aditi Dutt
(74) *Attorney, Agent, or Firm* — Fish & Richardson P.C.

(57) ABSTRACT

The present disclosure provides compositions and methods for treating subjects at risk for or with sensorineural hearing loss by modulating the rate of Atoh1 protein degradation to increase levels of Atoh1 protein.

13 Claims, 17 Drawing Sheets

Specification includes a Sequence Listing.

(56) References Cited

U.S. PATENT DOCUMENTS

| 10,603,295 | B2 | 3/2020 | Edge et al. |
| 10,925,872 | B2 | 2/2021 | Lorrain et al. |
| 2003/0114381 | A1 | 6/2003 | Cotanche et al. |
| 2004/0029862 | A1 | 2/2004 | Belanger et al. |
| 2004/0049038 | A1 | 3/2004 | Collins et al. |
| 2004/0186147 | A1 | 9/2004 | Hannam et al. |
| 2005/0019801 | A1 | 1/2005 | Rubin et al. |
| 2005/0119293 | A1 | 6/2005 | Collins et al. |
| 2005/0143369 | A1 | 6/2005 | Castro Pineiro et al. |
| 2005/0182109 | A1 | 8/2005 | Collins et al. |
| 2005/0182111 | A1 | 8/2005 | Pineiro et al. |
| 2005/0215602 | A1 | 9/2005 | Campbell et al. |
| 2005/0287127 | A1 | 12/2005 | Li et al. |
| 2006/0030837 | A1 | 2/2006 | McKenna et al. |
| 2007/0093878 | A1 | 4/2007 | Edge et al. |
| 2008/0146617 | A1 | 6/2008 | Aud et al. |
| 2008/0267929 | A1 | 10/2008 | Li et al. |
| 2009/0098093 | A1 | 4/2009 | Edge |
| 2009/0099237 | A1 | 4/2009 | Aud et al. |
| 2009/0124568 | A1 | 5/2009 | Heller et al. |
| 2009/0232780 | A1 | 9/2009 | Edge et al. |
| 2009/0297533 | A1 | 12/2009 | Lichter et al. |
| 2009/0306225 | A1 | 12/2009 | Lichter et al. |
| 2010/0273864 | A1 | 10/2010 | Lichter et al. |
| 2011/0020232 | A1 | 1/2011 | Eberhart et al. |
| 2011/0033480 | A1 | 2/2011 | Sarkar et al. |
| 2011/0305674 | A1 | 12/2011 | Edge et al. |
| 2011/0319377 | A1 | 12/2011 | Lichter et al. |
| 2013/0085112 | A1 | 4/2013 | Collard et al. |
| 2013/0210145 | A1 | 8/2013 | Edge |
| 2013/0225543 | A1 | 8/2013 | Jones et al. |
| 2014/0044763 | A1 | 2/2014 | Kustov et al. |
| 2015/0030568 | A1 | 1/2015 | Li et al. |
| 2015/0209406 | A1 | 7/2015 | Chen |
| 2017/0349884 | A1 | 12/2017 | Karp et al. |
| 2018/0148456 | A1 | 5/2018 | Clay et al. |
| 2019/0010449 | A1 | 1/2019 | Edge et al. |
| 2019/0203210 | A1 | 7/2019 | Edge et al. |
| 2019/0247381 | A1 | 8/2019 | Edge et al. |
| 2020/0255800 | A1 | 8/2020 | Edge |
| 2021/0290686 | A1 | 9/2021 | Edge et al. |
| 2021/0299138 | A1 | 9/2021 | Edge et al. |
| 2022/0008433 | A1 | 1/2022 | Edge et al. |

FOREIGN PATENT DOCUMENTS

| JP | 2006-117536 | 5/2006 | |
| JP | 2006/520386 | 9/2006 | |
| JP | 2007/503816 | 3/2007 | |
| JP | 2007/526248 | 9/2007 | |
| JP | 2011-518195 | 6/2011 | |
| JP | 2012-509899 | 4/2012 | |
| WO | WO 1998/028268 | 7/1998 | |
| WO | WO 2000/053632 | 9/2000 | |
| WO | WO 2000/059939 | 10/2000 | |
| WO | WO 2001/070677 | 9/2001 | |
| WO | WO 2002/049038 | 6/2002 | |
| WO | WO 2003/093251 | 11/2003 | |
| WO | WO 2003/093252 | 11/2003 | |
| WO | WO 2003/093253 | 11/2003 | |
| WO | WO 2003/093264 | 11/2003 | |
| WO | WO 2004/039370 | 5/2004 | |
| WO | WO 2004/039800 | 5/2004 | |
| WO | WO 2005/014553 | 2/2005 | |
| WO | WO 2005/030731 | 4/2005 | |
| WO | WO 2006/026570 | 3/2006 | |
| WO | WO 2007/075911 | 7/2007 | |
| WO | WO 2008/076556 | 6/2008 | |
| WO | WO-2008076556 A2 * | 6/2008 | .............. A61P 27/16 |
| WO | WO 2009/087130 | 7/2009 | |
| WO | WO 2009/132050 | 10/2009 | |
| WO | WO 2010/060088 | 5/2010 | |
| WO | WO 2012/005805 | 1/2012 | |
| WO | WO 2014/145205 | 9/2014 | |
| WO | WO 2014/159356 | 10/2014 | |
| WO | WO 2015/168149 | 11/2015 | |
| WO | WO 2016/022776 | 2/2016 | |
| WO | WO 2016/037016 | 3/2016 | |
| WO | WO 2017/151907 | 9/2017 | |
| WO | WO 2018/111926 | 6/2018 | |

OTHER PUBLICATIONS

MSCV retrovirus system, on Mar. 14, 2025, 2 pages (Year: 2025).*

Pickering et al (Sem Cell Dev Biol 16: 39-47, 2005) (Year: 2005).*

Office Action in Japanese Appln. No. 2022-069599, dated Jun. 6, 2023, 3 pages (with English translation).

Abbott et al., "Coordinated regulation of Toll-like receptor and NOD2 signaling by K63-linked polyubiquitin chains," Molecular and Cellular Biology, 2007, 27:6012-6025.

Adam et al., "Cell fate choices and the expression of Notch, Delta and Serrate homologues in the chick inner ear: parallels with *Drosophila* sense-organ development," Development, 125(23):4645-54 (Dec. 1998).

Adamo et al., "LSD1 regulates the balance between self-renewal and differentiation in human embryonic stem cells," Nat Cell Biol, Jun. 2011, 13(6):652-659, 20 pages.

Adhikary et al., The ubiquitin ligase HectH9 regulates transcriptional activation by Myc and is essential for tumor cell proliferation, Cell, 2005, 123 :409-421.

Adler and Raphael, "New hair cells arise from supporting cell conversion in the acoustically damaged chick inner ear," Neuroscience Letters, Feb. 1996, 205: 17-20.

Ahmed and Streit, "LSD1 interacts with cMyb to demethylate repressive histone marks and maintain inner ear progenitor identity," Development, 2018, 145(4):dev160325, 9 pages.

Aletsee et al., "The disintegrin Kistrin inhibits neurite extension from spiral ganglion explants cultured on laminin," Audiol. Neurootol., 6:57-65 (2001).

Armstrong et al, "Porcine neural xenografts in the immunocompetent rat: immune response following grafting of expanded neural precursor cells," Neuroscience, Sep. 2001, 106(1):201-216.

Artavanis-Tsakonas et al., "Notch Signaling," Sci., 1995, 268:225-232.

Azuara et al., "Chromatin signatures of pluripotent cell lines," Nat Cell Biol, May 2006, 8(5):532-538, 11 pages.

Ballas et al., "Regulation of neuronal traits by a novel transcriptional complex," Neuron, Aug. 2001, 31(3):353-365.

Barker et al, "A Role for Complement in the Rejection of Porcine Ventral Mesencephalic Xenografts in a Rat Model of Parkinson's Disease," The Journal of Neuroscience, May 2000, 20(9):3415-3424.

Barker et al., "Identification of stem cells in small intestine and colon by marker gene Lgf5," Nature, 2007, 449: 1003-1007.

Barker, "Wnt Signaling: Volume 1: Pathway Methods and Mammalian Models," in Methods in Molecular Biology, Nov. 2008, 5-15.

Bartolami et al., "Appearance and Distribution of the 275 kD Hair-Cell Antigen During Development of the Avian Inner Ear," J. Comp. Neurol., 314:777-788 (1991).

Basi et al., "Amyloid precursor protein selective gamma-secretase inhibitors for treatment Amyloid precursor protein selective gamma-secretase of Alzheimer's disease," Alzheimer's Research & Therapy, 2:36 (2010) pp. 1-21.

Batts et al., "Notch signaling and Hes labeling in the normal and drug-damaged organ of Corti," Hear Res., 249:15-22 (Mar. 2009).

Becvarovski et al., "Round Window Gentamicin Absorption: An In Vivo Human Model," Laryngoscope, Sep. 2002, 112: 1610-1613.

Ben-Arie et al., "Math1 is essential for genesis of cerebellar granule neurons." Nature, 1997, 390: 169-172.

Ben-Arie et al., "Functional conservation of atonal and Math1 in the CNS and PNS," Development, 2000, 127:1039-1048.

Bermingham et al., "Math1: An Essential Gene for the Generation of Inner Ear Hair Cells," Science, 1999, 284: 1837-1841.

Bernstein et al., "A bivalent chromatin structure marks key developmental genes in embryonic stem cells," Cell, Apr. 2006, 125(2):315-326.

(56)　　　　　References Cited

OTHER PUBLICATIONS

Bernstein et al., "Methylation ofhistone H3 Lys 4 in coding regions of active genes, " Proc Natl Acad Sci U S A, Jun. 2002, 99(13):8695-8700.

Bertrand et al., "Proneural genes and the specification of neural cell types," Nature Reviews Neuroscience, 2002, 3:517-530.

Beurel et al., "Glycogen synthase kinase-3 (GSIG): Regulation, actions, and diseases," Pharmacology & Therapeutics, 2015, 148:114-131.

Bodson et al., "Hair cell progenitors: identification and regulatory genes," Acta Otolaryngol, Mar. 2010, 130(3):312-7.

Borden et al., "Hyaluronic Acid Hydrogel Sustains the Delivery of Dexamethasone across the Round Window Membrane," Audiol Neurootol., 2011, 16(1):1-11.

Bossuyt et al., "Atonal homolog 1 is a tumor suppressor gene," PLoS Biology, 2009, 7:e39.

Bouchard et al., "Pax2 and homeodomain proteins cooperatively regulate a 435 bp enhancer of the mouse Pax5 gene at the midbrain-hindbrain boundary," Develop., 127:1017-28 (2000).

Bramhall, "Lgr5-Positive Supporting Cells Generate New Hair Cells in the Postnatal Cochlea," Stem Cell Reports, Mar. 2014, 2:1-12.

Breuskin et al., "Strategies to regenerate hair cells: identification of progenitors and critical genes," Hear Res, 2008, 236(1-2):1-10.

Brooker et al., "Notch ligands with contrasting functions: Jagged1 and Delta1 in the mouse inner ear," Development, 2006,133:1277-1286.

Brors et al., "EphA4 Provides Repulsive Signals to Developing Cochlear Ganglion Neurites Mediated through Ephrin-B2 and -B3," J. Comp. Neurol., 462:90-100 (2003).

Bryant et al., "Sensory organ development in the inner ear: Molecular and cellular mechanisms," British Medical Bulletin, 63:39-57 (2002).

Burns and Stone, "Development and regeneration of vestibular hair cells in mammals," Semin Cell Dev Biol, 2017, 65: 96-105.

Burns et al, "MYC Gene Delivery to Adult Mouse Utricles Stimulates Proliferation of Postmitotic Supporting Cells In Vitro," PLOS ONE, Oct. 2012, 7: 248704.

Burton et al., "The role of Pax2 in mouse inner ear development," Dev. Biol., 272:161-175 (2004).

CA Office Action in Canadian Appln. No. 2,883,896, dated Jul. 16, 2019, 4 pages.

CA Office Action in Canadian Appln. No. 2,883,896, dated Apr. 1, 2021, 4 pages.

Cafaro et al., "Atoh1 expression defines activated progenitors and differentiating hair cells during avian hair cell regeneration," Developmental dynamics, 2007, 236:156-170.

Cai et al., "Characterization of the transcriptome of nascent hair cells and identification of direct targets of the Atoh1 transcription factor," J Neurosci, Apr. 2015, 35(14):5870-5883.

Cai et al., "Conditional deletion of Atoh1 reveals distinct critical periods for survival and function of hair cells in the organ of Corti," The Journal of Neuroscience, 2013, 10110-10122.

Caiazzo et al., "Direct generation of functional dopaminergic neurons from mouse and human fibroblasts," Nature, 476:224-7 (Jul. 2011).

Carlisle et al., "Specific expression of Kcna10, Pxn and Odf2 in the organ of Corti," Gene Expr Patterns, May 2012, 12:172-179.

Cau et al., "Mash1 activates a cascade of bHLH regulators in olfactory neuron progenitors," Develop., 124:1611-1621 (1997).

Chai et al., "Wnt signaling induces proliferation of sensory precursors in the postnatal mouse cochlea," PNAS, 2012, 109: 8167-8172.

Charron et al., "The Morphogen Sonic Hedgehog is an Axonal Chemoattractant that Collaborates with Netrin-1 in Midline Axon Guidance," Cell., 113:11-23 (2003).

Chen and Segil, "p27$^{Kip1}$ links cell proliferation to morphogenesis in the developing organ of Corti," Development, 1999, 126(8):1581-1590.

Chen et al., "Histone Demethylase LSD1 Promotes Adipocyte Differentiation through Repressing Wnt Signaling," Cell Chem Biol, Sep. 2016, 23(10):1228-1240.

Chen et al., "ARF-BPI/Mule is a critical mediator of the ARF tumor suppressor," Cell, 2005. 121: 1071-1083.

Chen et al., "The role of Math1 in inner ear development: Uncoupling the establishment of the sensory primordium from hair cell fate determination," Develop., 129:2495-2505 (2002).

Cheng et al., "Destabilization of Atoh1 by E3 Ubiquitin Ligase Huwel and Casein Kinase Is Essential for Normal Sensory Hair Cell Development," Journal of Biological Chemistry, Sep. 2016, 291(40):21096-21109.

Cheng, "Role Of The Ubiquitin-Proteasome Pathway In The Inner Ear: Identification Of An E3 Ubiquitin Ligase For Atoh1," Thesis for the Degree of Doctor of Philosophy in Health Sciences and Technology, Harvard-Massachusetts Institute of Technology, Aug. 29, 2014, 1-99.

Chim et al., "Deafness associated with the use of Bortezomib in multiple myeloma," Acta Oncologica, Jan. 2008, 47(2):323-324.

Chonko et al., "Atoh1 directs hair cell differentiation and survival in the late embryonic mouse inner ear," Dev Biol, Sep. 2013, 381(2):401-410.

Clevers, "Wnt/beta-catenin signaling in development and disease," Cell, 2006, 127:469-480.

Colter et al., "Rapid expansion of recycling stem cells in cultures of plastic-adherent cells from human bone marrow," Proc. Natl. Acad. Sci. U.S.A , 97:3213-3218 (2000).

Corrales et al., "Engraftment and Differentiation of Embryonic Stem Cell-Derived Neural Progenitor Cells in the Cochlear Nerve Trunk: Growth of Processes into the Organ of Corti," J. Neurobiol., 66:1489-500 (2006).

Corwin et al., "Regeneration of Sensory Hair Cells After Acoustic Trauma," Science, Jun. 1988, 240:1772-1774.

Cosgrove et al., "Integrin alphalbetal and transforming growth factor-beta1 play distinct roles in alport glomerular pathogenesis and serve as dual targets for metabolic therapy," Am. J. Pathol., 157:1649-59 (2000).

Cox et al., "Spontaneous hair cell regeneration in the neonatal mouse cochlea in vivo," Development, 2014, 141: 816-829.

Crowder and Freeman, "Glycogen Synthase Kinase-3b Activity Is Critical for Neuronal Death Caused by Inhibiting Phosphatidylinositol 3-Kinase or Akt but Not for Death Caused by Nerve Growth Factor Withdrawal," The Journal of Biological Chemistry, Nov. 2000, 275: 34266-34271.

Dabdoub et al., "Abstract # 443: WNt/B-Catenin Signaling in the Developing Mammalian Cochlea," ARO 31st Annual Midwinter Meeting, Phoenix, Arizona, Feb. 16-21, 2008, 3 pages.

Dabdoub et al., "Abstract # 8: Wnt Signaling in the Developing Mammalian Cochlea," ARO 30th Annual Midwinter Meeting, Denver, Colorado, Feb. 10-15, 2007, 2 pages.

D'Arca et al., "Huwe 1 ubiquitin ligase is essential to synchronize neuronal and glial differentiation in the developing cerebellum," PNAS, 2010, 107:5875-5880.

Daudet and Lewis, "Two contrasting roles for Notch activity in chick inner ear development: specification of pro sensory patches and lateral inhibition of hair-cell differentiation," Development, 132:541-51 (Feb. 2005).

Daudet et al., "Notch regulation of progenitor cell behavior in quiescent and regenerating auditory epithelium of mature birds," Dev Biol., 326(1):86-100 (Feb. 1, 2009).

Davis, "Hearing disorders in the population: first phase findings of the MRC National Study of Hearing," Hearing Science and Hearing Disorders, 1983, 35-60.

De Groot et al., "Huwel-mediated ubiquitylation of dishevelled defines a negative feedback loop in the Wnt signaling pathway," Science Signaling, Mar. 2014, 7:ra26.

Declaration of Non-Establishment of International Search Report for PCT/US2009/065747, mailed Apr. 8, 2010.

Deshaies and Joazeiro, "RING domain E3 ubiquitin ligases," Annual Review of Biochemistry, 2009, 78:399-434.

Dezawa et al., "Specific induction of neuronal cells from bone marrow stromal cells and application for autologous transplantation," J. Clin. Invest., 113:1701-1710 (2004).

(56)         References Cited

OTHER PUBLICATIONS

Dobin et al., "STAR: ultrafast universal RNAseq aligner," Bioinformatics, Jan. 2013, 29(1):15-21.

Doetzlhofer et al., "Hey2 regulation by FGF provides a Notch-independent mechanism for maintaining pillar cell fate in the organ of Corti," Dev Cell, 16:58-69 (Jan. 2009).

Dong et al., "Calpain inhibitor MDL28170 modulates Aβ formation by inhibiting the formation of intermediate Aβ46 and protecting Aβ from degradation," The FASEB Journal, Dec. 2005, 21 pages.

D'Onofrio et al., "Advances in the identification of γ-secretase inhibitors for the treatment of Alzheimer's disease," Expert Opinion on Drug Discovery, Jan. 1, 2012, 7(1):19-37.

Doyonnas et al., "Hematopoietic contribution to skeletal muscle regeneration by myelomoncytic precursors," Proc. Natl. Acad. Sci. U.S.A, 101:13507-13512 (2004).

Eatock and Rusch, "Developmental changes in the physiology of hair cells," Cell & Developmental Biology, 1997, 8:265-275.

Edge and Chen, "Hair cell regeneration," Curr Opin Neurobiol, 2008, 18: 377-382.

Edge et al., "Current Applications of Cellular Xenografts," Trans. Proc., 32:1169-1171 (2000).

Eng et al., "An approach to correlate tandem mass spectral data of peptides with amino acid sequences in a protein database," Journal of the American Society for Mass Spectrometry, 1994, 5:976-989.

Escobar-Chávez et al., "Applications of thermo-reversible pluronic F-127 gels in pharmaceutical formulations," J Pharm Pharm Sci., 2006, 9(3):339-58.

European Search Report in Application No. 13836099, dated Mar. 8, 2016, 9 Pages.

Examination Report issued in Australian Patent Application No. 2007334260 on Aug. 23, 2012 (5 pages).

Extended European Search Report issued in corresponding European Patent Application No. 07871464.9, mailed Nov. 17, 2010.

Extended European Search Report issued in EP 0982830, mailed Dec. 7, 2012.

Feng et al., "Blocking caspase-3-dependent pathway preserves hair cells from salicylate-induced apoptosis in the guinea pig cochlea," Mol Cell Biochem., 2011, 353:291-303.

Ferrer-Vaquer et al., "A sensitive and bright single-cell resolution live imaging reporter of Wnt/ss-catenin signaling in the mouse," BMC Dev Biol, Dec. 2010, 10:121, 18 pages.

Final Office Action issued in U.S. Appl. No. 13/130,607 on Oct. 21, 2013, 11 pages.

Flora et al., "Deletion of Atoh1 disrupts Sonic Hedgehog signaling in the developing cerebellum and prevents medulloblastoma," Science, 2009, 326:1424-1427.

Flora et al., "The E-protein Tcf4 interacts with Math 1 to regulate differentiation of a specific subset of neuronal progenitors," PNAS, 2007, 104: 15382-15387.

Forge et al., "Hair Cell Recovery in the Vestibular Sensory Epithelia of Mature Guinea Pigs," The Journal of Comparative Neurology, 1998, 397: 69-88.

Forge et al., "Ultrastructural evidence for hair cell regeneration in the mammalian inner ear," Science, 1993, 259: 1616-1619.

Forget et al., "Shh Signaling Protects Atoh1 from Degradation Mediated By The E3 Ubiquitin Ligase Huwel In Neural Precursors," Developmental Cell, Jun. 2014, 29: 649-661.

Forneris et al., "Histone demethylation catalysed by LSD1 is a flavin-dependent oxidative process," FEBS Lett, Apr. 2005, 579(10):2203-2207.

Frisina, "Age-related hearing loss: ear and brain mechanisms," Annals of the New York Academy of Sciences, 2009, 1170: 708-717.

Fritzsch et al., "Atoh1 Null Mice Show Directed Afferent Fiber Growth to Undifferentiated Ear Sensory Epithelia Followed by Incomplete Fiber Retention," Dev. Dyn., 233:570-583 (2005).

Fritzsch et al., "Lack of Neurotrophin 3 Causes Losses of Both Classes of Spiral Ganglion Neurons in the Cochlea in a Region-Specific Fashion," J. Neurosci., 17:6213-6225 (1997).

Fritzsch, "Development of inner ear afferent connections: forming primaly neurons and connecting them to the developing sensory epithelia," Brain Research Bulletin, 2003, 60:423-433.

Fuerer and Nusse, "Lentiviral vectors to probe and manipulate the Wnt signaling pathway," PLoS One, 2010, 5(2):e9370, 7 pages.

Fujioka et al., "SY3A-H5 A novel y-secretase inhibitor, LY411575, replaced auditory hair cells and recovered hearing loss after severe acoustic trauma in mice," Neurosci Res., 2008, 61(Suppl):S25.

Fujioka et al., "In vivo differentiation toward hair cell: A novel gamma-secretase inhibitor, LY411575, replaced auditory hair cells and ameliorated hearing impairment after severe acoustic trauma in mice," Presented at The 31st Annual Meeting of the Japan Neuroscience Society Symposium "Regeneration of Sensory Cells in the Inner Ear—From Bench to Bedside," Jul. 7, 2008, 30 pages.

Fujioka et al., "Manipulating cell fate in the cochlea: a feasible therapy for hearing loss," Trends Neurosci, 2015, 38: 139-144.

Gage, "Cell therapy," Nature, 392(6679 Suppl):18-24 (1998).

Gao et al., "mTOR drives its own activation via SCF(~TrCP)dependent degradation of the mTOR inhibitor DEPTOR," Molecular Cell, 2011, 44:290-303.

Gao et al., "Quantitative imaging of cochlear soft tissues in wild-type and hearingimpaired transgenic mice by spectral domain optical coherence tomography," Optics Express, 2011, 19:15415-15428.

Garapaty-Rao et al., "Identification of EZH2 and EZH1 Small Molecule Inhibitors with Selective Impact on Diffuse Large B Cell Lymphoma Cell Growth," Chem. Biol, 2013, 20(11):1329-1339.

Ge et al., "Distribution of PLGA nanoparticles in chinchilla cochleae," Otolaryngol Head Neck Surg., Oct. 2007, 137(4):619-23.

Geling et al., "A γ-secretase inhibitor blocks Notch signaling in vivo and causes a severe neurogenic phenotype in zebrafish," EMBO report, 2002, 688-694.

Geng et al., "Comprehensive Expression of Wnt Signaling Pathway Genes during Development and Maturation of the Mouse Cochlea," PLoS One, Feb. 2016, 11(2):e0148339, 18 pages.

Gillespie et al., "LIF is more potent than BDNF in promoting neurite outgrowth of mammalian auditory neurons in vitro," Neuro. Rep., 12:275-279 (2001).

Golub et al., "Hair Cell Replacement in Adult Mouse Utricles after Targeted Ablation of Hair Cells with Diphtheria Toxin," The Journal of Neuroscience, Oct. 2012, 32: 15093-15105.

Gowan et al., "Crossinhibitory Activities of Ngn1 and Math1 Allow Specification of Distinct Dorsal Interneurons," Neuron., 31:219-232 (2001).

Goycoolea and Lundman, "Round window membrane. Structure function and permeability: a review," Microsc Res Tech., 36:201-11 (Feb. 1, 1997).

Gregorieff and Clevers, "Wnt signaling in the intestinal epithelium: from endoderm to cancer," Genes & Development, 2005, 19:877-890.

Groves, "The challenge of hair cell regeneration," Exp Biol Med (Maywood), Apr. 2010, 235(4):434-446.

Gubbels et al., "Functional auditory hair cells produced in the mammalian cochlea by in utero gene transfer," Nature, 2008, 455:537-541.

Guo et al., "Targeting the Notch signaling pathway in cancer therapeutics," Thoracic Cancer, 2014, 5: 473-486.

Haapasalo and Kovacs; "The Many Substrates of Presenilin/γ-Secretase" Journal Alzheimers Disease. 2011: 25(1): 3-28.

Hadland et al., "γ-secretase inhibitors repress thymocyte development," Proc Natl. Acad Sci USA, 98:7487-91 (Jun. 19, 2001).

Han and Shen, "Targeting γ-secretase in breast cancer," Breast Cancer: Targets and Therapy, 2012, 2012: 83-90.

Hanna et al., "Pluripotency and cellular reprogramming: facts, hypotheses, unresolved issues," Cell, Nov. 2010, 143(4):508-525.

Hartman et al., "Hes5 expression in the postnatal and adult mouse inner ear and the drug-damaged cochlea," J Assoc Res Otolaryngol., 10:321-40 (Sep. 2009).

Havenith et al., "Spiral ganglion cell survival after round window membrane application of brain-derived neurotrophic factor using gelfoam as carrier," Hearing Research, Feb. 2011, 272(1-2):168-177.

(56)                    References Cited

OTHER PUBLICATIONS

Hawkins et al., "The developmental genetics of auditory hair cells," Hum. Mol. Genet., 13:R289-296 (2004).

Heintzman et al., "Distinct and predictive chromatin signatures of transcriptional promoters and enhancers in the human genome," Nat Genet, Mar. 2007, 39(3):311-318.

Heller et al., "Parvalbumin 3 is an Abundant Ca2+ Buffer in Hair Cells," J. Assoc. Res. Otolaryngol., 3:488-498 (2002).

Helms et al., "Autoregulation and multiple enhancers control Math1 expression in the developing nervous system," Develop., 127:1185-1196 (2000).

Helms et al., "Overexpression of MATH1 Disrupts the Coordination of Neural Differentiation in Cerebellum Development," Mol. Cell. Neurosci., 17:671-682 (2001).

Hendrickx & Leyns, "Non-conventional Frizzled ligands and Wnt receptors," Develop Growth Differ., 2008, 50:229-243.

Hermann et al., "Efficient generation of neural stem cell-like cells from adult human bone marrow stromal cells," J. Cell. Sci., 117:4411-4422 (2004).

Herold et al., "Miz1 and HectH9 regulate the stability of the checkpoint protein, TopBP1," The EMBO Journal, 2008, 27:2851-2861.

Herzog et al., "Plasticity of marrow-derived stem cells," Blood, 102:3483-3493 (2003).

Hess et al., "Bone marrow-derived stem cells initiate pancreatic regeneration," Nat. Biotechnol., 21:763-770 (2003).

Hildebrand et al, "Advances in Molecular and Cellular Therapies for Hearing Loss," Molecular Therapy, 2008, 16(2):224-236.

Hirabayashi et al., "The Wnt/beta-catenin pathway directs neuronal differentiation of cortical neural precursor cells," Development, 2004, 131: 2791-2801.

Hödar et al., "Genome-wide identification of new Wnt/beta-catenin target genes in the human genome using CART method," BMC Genomics, 2010, 11:348, 15 pages.

Horie et al., "Sustained delivery of lidocaine into the cochlea using poly lactic/glycolic acid microparticles," Laryngoscope, 2010, 120(2):377-83.

Hosoya et al., "Method for efficient screening of substances inducing differentiation into inner ear hair cells with the use of spheres derived from inner ear cells," Otol Jpn, 2008, 18(4): 275 (with English translation).

Hosoya et al., "An efficient screening method using inner-ear derived spheres for selection of compounds that induce hair cell differentiation," Neurosci. Res., 2008, 61S:S57 Abstract, 2 pages.

Hu and Ulfendahl, "Cell replacement therapy in the inner ear," Stem Cell and Development, 15:449-459 (2006).

Hu et al., "Diphtheria Toxin-Induced Cell Death Triggers Wnt-Dependent Hair Cell Regeneration in Neonatal Mice," J Neurosci, 2016, 36:9479-9489.

Hu et al., "Wnt/beta-catenin signaling in murine hepatic transit amplifying progenitor cells," Gastroenterology, Nov. 2007, 133(5):1579-1591.

Hu et al., "Neural cograft stimulates the survival and differentiation of embryonic stem cells in the adult mammalian auditory System," Brain Research, 2005, 1051:137-144.

Hu et al., "Survival and neural differentiation of adult neural stem cells transplanted into the mature inner ear," Exper. Cell. Res., 302:40-47 (2005).

Huang et al., "Lysine 63-linked polyubiquitination is required for EGF receptor degradation," PNAS, Sep. 2013, 110(39):15722-15727.

Huang, "Age-related hearing loss," Minn Med, 2007, 90(10):48-50.

Huibregtse et al., A family of proteins structurally and functionally related to the E6-AP ubiquitin-protein ligase, PNAS, 1995, 92:5249.

Hume et al., "Expression of LHX3 and SOX2 during mouse inner ear development," Gene Expression Patterns, 2007, 7:798-807.

Husseman and Raphael, Gene therapy in the inner ear using adenovirus vectors. Advances in Oto-Rhino-Laryngology, 2009, 66:37-51.

Huynh et al., "The novel gamma secretase inhibitor RO4929097 reduces the tumor initiating potential of melanoma," PLoS One, 6(9):e25264, (2011) 10 pages.

Hyde et al., "Studies to investigate the in vivo therapeutic window of the γ-secretase inhibitor N2-[(2S)-2-(3,5-difluorophenyl)-2-hydroxyethanoyl]-N1-[(7S)-5-methyl-6-oxo-6,7-dihydro-5H-dibenzo[b,d]azepin-7-yl]-L-alaninamide (LY411,575) in the CRND8 mouse," J Pharmacol Exp Ther., 319:1133-43 (Dec. 2006).

Hyun et al., "In Vitro and in Vivo Release of Albumin Using a Biodegradable MPEG-PCL Diblock Copolymer as an in Situ Gel-Forming Carrier," Biomacromolecules, Apr. 2007, 8(4):1093-100.

Ikeda and Dikic, "Atypical ubiquitin chains: new molecular signals. "Protein Modifications: Beyond the Usual Suspects" review series," EMBO Reports, 2008, 9:536-542.

Inaoka et al., "Local application of hepatocyte growth factor using gelatin hydrogels attenuates noise-induced hearing loss in guinea pigs," Acta Otolaryngol., Apr. 2009, 129(4):453-7.

Incesulu and Nadal, "Correlation of acoustic threshold measures and spiral ganglion cell survival in severe to profound sensorineural hearing loss: implications for cochlear implantation," The Annals of Otology, Rhinology, and Laryngology, 1998, 107:906-911.

Inoue et al., "Mule/Huwel/Arf-BP1 suppresses Ras-driven tumorigenesis by preventing c-Myc/Miz1-mediated down-regulation ofp21 and p15," Genes & Development, 2013, 27: 1101-1114.

International Preliminary Report on Patentability for PCT/US2009/065747, issued May 24, 2011.

International Preliminary Report on Patentability in International Application No. PCT/US2013/058446, issued Mar. 10, 2015, 11 pages.

International Preliminary Report on Patentability in International Application No. PCT/US2016/064727, mailed on Jun. 14, 2018, 9 pages.

International Preliminary Report on Patentability in International Application No. PCT/US2017/015379, mailed on Aug. 9, 2018, 11 pages.

International Preliminary Report on Patentability in International Appln. No. PCT/US2019/063418, mailed on Jun. 10, 2021, 9 pages.

International Preliminary Report on Patentability issued in corresponding International Application No. PCT/US2007/084654, mailed May 28, 2009.

International Search Report and Written Opinion in International Application No. PCT/US15/43976, mailed on Jan. 20, 2016, 16 pages.

International Search Report and Written Opinion in International Application No. PCT/US2013/058446, mailed Dec. 26, 2013, 8 pages.

International Search Report and Written Opinion in International Application No. PCT/US2016/064727, mailed on May 1, 2017, 18 pages.

International Search Report and Written Opinion in International application No. PCT/US2017/015379, mailed on May 31, 2017, 18 pages.

International Search Report and Written Opinion in International Appln. No. PCT/US2019/063418, mailed on Apr. 23, 2020, 12 pages.

International Search Report issued in corresponding International Application No. PCT/US2007/84654, mailed Oct. 3, 2008.

Inuzuka et al., "SCFFBW7 regulates cellular apoptosis by targeting MCLI for ubiquitylation and destruction," Nature, 2012, 470:104-109.

Invitation to Pay Additional Fees And, Where Applicable, Protest Fee in International Appln. No. PCT/US2019/063418, mailed on Feb. 24, 2020, 2 pages.

Ito et al., "Neurotrophins Facilitate Neuronal Differentiation of Cultured Neural Stem Cells Via Induction of mRNA Expression of Basic Helix-Loop-Helix Transcription Factors Mash1 and Math1," J. Neurosci. Res., 71:648-658 (2003).

Ivan et al., "HIFalpha targeted for VHL-mediated destruction by praline hydroxylation: implications for 02 sensing," Science, 2001,292:464-468.

Ivanov et al., "Genes required for Drosophila nervous system development identified by RNA interference," Proc. Nat. Acad. Sci., 101:16216-16221 (2004).

(56)    References Cited

OTHER PUBLICATIONS

Izumikawa et al., "Auditory hair cell replacement and hearing improvement by Atoh1 gene therapy in deaf mammals," Nat Med., 11(3)271-6 (Mar. 2005).
Jaakkola et al., "Targeting ofHIF-alpha to the von Hippel-Lindau ubiquitylation complex by 02-regulated prolyl hydroxylation," Science, 2001, 292:468-472.
Jacques et al., "A dual function for canonical Wnt/beta-catenin signaling in the developing mammalian cochlea," Development, Dec. 2012, 139(23):4395-4404, 18 pages.
Jaenisch and Bird, "Epigenetic regulation of gene expression: how the genome integrates intrinsic and environmental signals," Nat Genet, Mar. 2003, 33 Suppl:245-254.
Jahan et al., "Beyond generalized hair cells: molecular cues for hair cell types," Hear Res, Mar. 2013, 297:30-41.
Jarriault et al., "Delta-1 Activation of Notch-1 Signaling Results in HES-1 Transactivation," Mol. Cell. Biol, 1998, 18:7423-7431.
Jarriault et al., "Signalling downstream of activated mammalian Notch," Nature, 1995, 377:355-358.
Jeon et al., "Notch Signaling Alters Sensory or Neuronal Cell Fate Specification of Inner Ear Stem Cells," J. Neurosci, 2011, 31:8351-8358.
Jeon et al., "Bone marrow mesenchymal stem cells are progenitors in vitro for inner ear hair cells," Molecular and Cellular Neurosciences, 34:59-68 (2007).
Jiang et al., "Neuroectodermal differentiation from mouse multipotent adult progenitor cells," Proc. Natl. Acad. Sci .U.S.A, 100:11854-11860 (2003).
Jiang et al., "Pluripotency of mesenchymal stem cells derived from adult marrow," Nature, 418:41-49 (2002).
Jin et al., "Systematic analysis and nomenclature of mammalian F-box proteins," Genes Dev, 2004, 18(21):2573-2580.
Jorstad et al., "Stimulation of functional neuronal regeneration from Müller glia in adult mice," Nature, Aug. 2017, 548(7665):103-107.
Kaneko et al., "Musashi1: an evolutionarily conserved marker for CNS progenitor cells including neural stem cells," Dev Neurosci., 22:139-53 (2000).
Kawamoto et al., "Spontaneous hair cell regeneration in the mouse utricle following gentamicin ototoxicity," Hearing Research, 2009, 247: 17-26.
Kearns et al., "Functional annotation of native enhancers with a Cas9-histone demethylase fusion," Nat Methods, 2015, 12:401-403, 6 pages.
Kehrle et al., "Comparison of Auditory Brainstem Response Results in Normal-Hearing Patients With and Without Tinnitus," Arch Otolaryngol Head Neck Surg., 2008, 134(6):647-651.
Kelley et al., "Regulation of cell fate in the sensory epithelia of the inner ear," Nat Rev Neurosci, 2006, 7: 837-849.
Kerenyi et al., "Histone demethylase LSD1 represses hematopoietic stem and progenitor cell signatures during blood cell maturation," eLife, 2013, 2:e00633, 23 pages.
Kicic et al., "Differentiation of Marrow Stromal Cells into Photoreceptors in the Rat Eye," J. Neurosci., 23:7742-7749 (2003).
Kiernan et al., "Sox2 is required for sensory organ development in the mammalian inner ear," Nature, 434:1031-1035 (2005).
Kim et al., "Dopamine neurons derived from embryonic stem cells function in an animal model of Parkinson's disease," Nature, 418:50-6 (2002).
Kim et al., "NeuroD-null mice are deaf due to a severe loss of the inner ear sensory neurons during development," Develop., 128:417-426 (2001).
Klisch et al., "In vivo Atoh1 targetome reveals how a proneural transcription factor regulates cerebellar development," PNAS, 2011, 108(8):3288-3293.
Knippschild et al., "Metaanalysis to Estimate the Expected Drop Out-Rates Reported in Clinical Trials on Cataract Surgery," 2014, 231: 151-157 (with English abstract).
Knippschild et al., "The CK1 family: contribution to cellular stress response and its role in carcinogenesis," Frontiers in Oncology, May 2014, 4: 32 pages.

Koch et al., "The landscape of histone modifications across 1% of the human genome in five human cell lines," Genome Res, 2007, 17(6):691-707.
Kondo et al., "Sonic Hedgehog and retinoic acid synergistically promote sensory fate specification from bone marrow-derived pluripotent stem cells," Proc. Natl. Acad. Sci. U.S.A., 102(13):4789-4794 (Mar. 2005).
Kondo et al., "Wnt Signaling Promotes Neuronal Differentiation From Mesenchymal Stem Cells Through Activation ofTlx3," Stem Cells, 2011, 29(5):836-46.
Kopan et al., "The Canonical Notch Signaling Pathway: Unfolding the Activation Mechanism," Cell, 2009, 137:216-233.
Kurokawa et al., "A network of substrates of the E3 ubiquitin ligases MDM2 and HUWEI control apoptosis independently ofp53," Science Signaling, 2013, 6:ra32.
Lanford et al., "Notch signalling pathway mediates hair cell development in mammalian cochlea," Nature Genetics, 21:289-292 (1999).
Lang et al., "Contribution of Bone Marrow Hematopoietic Stem Cells to Adult Mouse Inner Ear: Mesenchymal Cells and Fibrocytes," J .Comp. Neurol., 496:187-201 (2006).
Lanzoni et al., "MDL 28170 Attenuates Gentamicin Ototoxicity," Audiological Medicine, 2005, 3:82-89.
Latres et al., "The human F box protein beta-Trcp associates with the Cull/Skp1 complex and regulates the stability of beta-catenin," Oncogene, Jan. 1999, 18:849-854.
Laurent et al., "A specific LSD1/KDM1A isoform regulates neuronal differentiation through H3K9 demethylation," Mol Cell, Mar. 2015, 57(6):957-970.
Ledent et al., "Phylogenetic analysis of the human basic helix-loop-helix proteins," Genome Biology, 2002 3:research0030.1.
Lee et al., "Proteasome inhibitors induce auditory hair cell death through peroxisome dysfunction," Biochem. Biophys. Res. Comm., Jan. 2015, 456(1):269-274.
Lee et al., "Efficient generation of midbrain and hindbrain neurons from mouse embryonic stem cells," Nat. Biotech., 18:675-9, (2000).
Lee et al., "EZH2 generates a methyl degron that is recognized by the DCAF1/DDB1/CUL4 E3 ubiquitin ligase complex," Molecular Cell, 2012, 48:572-586.
Lei et al., "Lysine-specific demethylase 1 promotes the sternness and chemoresistance of Lgr5(+) liver cancer initiating cells by suppressing negative regulators of beta-catenin signaling," Oncogene, Jun. 2015, 34(24):3188-98.
Leon et al., "Insulin-Like Growth Factor-I Regulates Cell Proliferation in the Developing Inner Ear, Activating Glycosyl-Phosphatidylinositol Hydrolysis and Fos Expression," Endocrinol., 136:3494-3503 (1995).
Li et al., "Round Window Membrane Delivery of L-Methionine Provides Protection from Cisplatin Ototoxicity Without Compromising Chemotherapeutic Efficacy," Neuro Toxicology, 2001, 22:163-176.
Li et al., "Correlation of Pax-2 Expression with Cell Proliferation in the Developing Chicken Inner Ear," J. Neurobiol., 60:61-70 (2004).
Li et al., "Generation of hair cells by stepwise differentiation of embryonic stem cells," Proc. Natl. Acad. Sci. U.S.A. Nov. 2003, 100(23):13495-13500.
Li et al., "Pluripotent stem cells from the adult mouse inner ear," Nat. Med., 9:1293-1299 (2003).
Li et al., "Specification of motoneurons from human embryonic stem cells," Nat. Biotechnol., 23:215-21 (2005).
Li et al., "Stem cells as therapy for hearing loss," Trends Mol. Med., 10:309-315 (2004).
Lin et al., "Hair cell damage recruited Lgr5-expressing cells are hair cell progenitors in neonatal mouse utricle," Front Cell Neurosci, Apr. 2015, 9: 1-11.
Lin et al., "Inhibition of notch activity promotes non-mitotic regeneration of hair cells in the adult mouse utricles," J Neurosci., 31(43):15329-15339 (Oct. 26, 2011).
Lo et al., "Mammalian achaete-scute homolog 1 is transiently expressed by spatially restricted subsets of early neuroepithelial and neural crest cells," Genes & Development, 1991, 5: 1524-1537.
Loo et al., "From short peptides to nanofibers to macromolecular assemblies in biomedicine," Biotechnol Adv., 2012, 30(3):593-603.

(56)                      References Cited

OTHER PUBLICATIONS

Loseva et al, "Comparison of reactive processes in the rat brain elicited by xenotransplantation of nervous tissues of chicken or pulmonate snail," Brain Research, 2001, 915:125-132.

Love et al., "Moderated estimation of fold change and dispersion for RNA-seq data with DESeq2," Genome Biol, 2014, 15(12):550, 21 pages.

Lu et al., "Abstract #: 774: The Influence of Glycogen Synthase Kinase 3 On Cell Proliferation in the Murine Vestibular Sensory Epithelium," ARO 31st Annual Midwinter Meeting, Phoenix, Arizona, Feb. 16-21, 2008, 3 pages.

Lu et al., "The Influence of Glycogen Synthase Kinase 3 in Limiting Cell Addition in the Mammalian Ear," Develop. Neurobiol., 68:1059-1075 (2008).

Luistro et al., "Preclinical Profile of a Potent γ-Secretase Inhibitor Targeting Notch Signaling with In vivo Efficacy and Pharmacodynamic Properties," Cancer Res, Oct. 2009, 69(19):7672-7690.

Lumpkin et al., "Math1-driven GFP expression in the developing nervous system of transgenic mice," Gene Expr Patterns, 3:389-95 (Aug. 2003).

Ma and Raible, "Signaling pathways regulating zebrafish lateral line development," Current Biology, 2009, 19:R381-386.

Ma et al., "Neurogenin 1 Null Mutant Ears Develop Fewer, Morphologically Normal Hair Cells in Smaller Sensory Epithelia Devoid of Innervation," Assoc. Res. Otolaryngol., 1:129-143 (2000).

Madisen et al., "A robust and high-throughput Cre reporting and characterization system for the whole mouse brain," Nat Neurosci, 2010, 13: 133-140.

Maiques-Diaz et al., "Enhancer Activation by Pharmacologic Displacement of LSD1 from GFI1 Induces Differentiation in Acute Myeloid Leukemia," Cell Rep, Mar. 2018, 22:3641-3659, 40 pages.

Maksimovic et al., "Epidermal Merkel cells are mechanosensory cells that tune mammalian touch receptors," Nature, 2014, 509:617-621.

Mangi et al., "Mesenchymal stem cells modified with Akt prevent remodeling and restore performance of infarcted hearts," Nat. Med., 9:1195-201 (2003).

Markkanen et al., "Regulation of oxidative DNA damage repair by DNA polymerase A and MutYH by cross-talk of phosphorylation and ubiquitination," PNAS, 2012, 109:437-442.

Maru et al., "Lentivirus-Based Stable Gene Delivery into Intestinal Organoids," Methods Mol Biol, 2016, 1422:13-21.

Masuda et al., "Dual antitumor mechanisms of notch signaling inhibitor in a T-cell acute lymphoblastic leukemia xenograft model," Cancer Sci., 100(12):2444-2450 (Dec. 2009).

Matei et al., "Smaller Inner Ear Sensory Epithelia in Neurog1 Null Mice Are Related to Earlier Hair Cell Cycle Exit," Dev. Dyn., 234:633-50 (2005).

Matsui et al., "Regeneration and replacement in the vertebrate inner ear," Drug Discov. Today, 10:1307-12 (2005).

Matsuoka et al., In Vivo and In Vitro Characterization of Bone Marrow-Derived Stem Cells in the Cochlea, Laryngoscope, Aug. 2006, 116:1363-1367.

McLean et al., "Clonal Expansion of Lgr5-Positive Cells from Mammalian Cochlea and High-Purity Generation of Sensory Hair Cells," Cell Reports, Feb. 2017, 18(8):1917-1929.

Meierhofer et al., "Quantitative analysis of global ubiquitination in HeLa cells by mass spectrometry," Journal of Proteome Research, 2008, 7:4566-4576.

Metzger et al., "LSD1 demethylates repressive histone marks to promote androgen-receptor-dependent transcription," Nature, Sep. 2005, 437(7057):436-439, 5 pages.

Mezey et al., "Transplanted bone marrow generates new neurons in human brains," Proc. Natl. Acad. Sci. U.S.A., 100:1364-1369 (2003).

Miesegaes et al., "Identification and subclassification of new Atoh1 derived cell populations during mouse spinal cord development," Developmental Biology, Mar. 2009, 327:339-351.

Mikulec et al., "Permeability of the round window membrane is influenced by the composition of applied drug solutions and by common surgical procedures," Otol Neurotol., 29:1020-6 (Oct. 2008).

Mitani et al., "Differential Effects between γ-Secretase Inhibitors and Modulators on Cognitive Function in Amyloid Precursor Protein-Transgenic and Nontransgenic Mice," J. Neuroscience, Feb. 2012.

Mizutari et al., "Notch inhibition induces cochlear hair cell regeneration and recovery of hearing after acoustic trauma," Neuron, 2013, 77: 58-69.

Moon et al., "WNT and B-catenin signalling: diseases and therapies," Nature Reviews, Sep. 2004, 5: 689-699.

Moore et al., "Modulation of Wnt Signaling Through Inhibition of Secreted Frizzled-Related Protein I (sFRP-1) with N-Substituted Piperidinyl Diphenylsulfonyl Sulfonamides," J Med.Chem., 2009, 52(1):105-116.

Morrison et al., "Mammalian Merkel cells are descended from the epidermal lineage," Developmental Biology, 2009, 336:76-83.

Murre et al., "Interactions between heterologous helixloop-helix proteins generate complexes that bind specifically to a common DNA sequence.," Cell, 1989, 58:537-544.

Murry et al., "Haematopoietic stem cells do not transdifferentiate into cardiac myocytes in myocardial infarcts," Nature., 428:664-668 (2004).

Nadol, Jr. et al., "Degenerative Changes in the Organ of Corti and Lateral Cochlear Wall in Experimental Endolymphatic Hydrops and Human Meniere's Disease," Acta Otolaryngol, 1995, Suppl 519: 47-59.

Naito Yasushi et al., "Transplantation of bone marrow stromal cells into the cochlea of chinchillas," NeuroReport, Lippincott Williams & Wilkins, 15:1-4 (2004).

Nakagawa, "Aiming for the treatment of inner ear diseases—the forefront of basic research," Bulletin of the Japan Otolaryngology Society, 2008, 11(10):655-663 (with machine abstract).

Naujokat and Saric, "Concise review: role and function of the ubiquitinproteasome system in mammalian stem and progenitor cells," Stem Cells, 2007, 25 :2408-2418.

Non-Final Office Action issued in U.S. Appl. No. 13/130,607 on Apr. 19, 2013, 11 pages.

Non-Final Office Action issued in U.S. Appl. No. 13/130,607 on Oct. 23, 2014, 12 pages.

Notice of Opposition to European Patent in European Application No. 09828380.7, dated Jan. 11, 2018, 39 pages.

Noy et al., "HUWE1 ubiquitinates MyoD and targets it for proteasomal degradation," Biochemical and Biophysical Research Communications, 2012, 418:408-413.

Ocampo et al., "In Vivo Amelioration of Age-Associated Hallmarks by Partial Reprogramming," Cell, Dec. 2016, 167(7):1719-1733. e12, 28 pages.

Oesterle et al., "Sox2 and JAGGED1 expression in normal and drug-damaged adult mouse inner ear," J Assoc Res Otolaryngol., 9:65-89 (Mar. 2008).

Office Action in European Application No. 13836099.5, dated Jul. 25, 2018, 5 pages.

Office Action in Japanese Application No. 2015-178811, dated Jun. 5, 2018, 12 pages (with English translation).

Office Action in Japanese Application No. 2015-178811, dated Oct. 17, 2017, 6 pages (with English translation).

Office Action in Japanese Application No. 2015-531223, dated Jan. 15, 2019, 6 pages (with English translation).

Office Action in Japanese Application No. 2015-531223, dated Jul. 11, 2017, 8 pages (with English translation).

Office Action in Japanese Application No. 2015-531223, dated Jun. 19, 2018, 7 pages (with English translation).

Office Action issued in AU2009316264 on Jan. 16, 2015 (5 pages).

Office Action issued in CA2,669,693 on Apr. 4, 2014 (4 pages).

Office Action issued in EP07871464.9 on May 6, 2014 (5 pages).

Office Action issued in European Application No. 09828380.7 on Mar. 26, 2014 (6 pages).

Office Action issued in Japanese Application No. 2011-537715 issued on Feb. 4, 2014 (translation) 4 pages.

Office Action issued in JP2009-537328 on Feb. 12, 2013 (7 pages).

(56) References Cited

OTHER PUBLICATIONS

Office Action issued in JP2011-537715 on Jan. 20, 2015 with English translation (7 pages).

Office Action issued in JP2015-178811 on Mar. 7, 2017 with English translation (5 pages).

Ohyama et al., "Wnt signals mediate a fate decision between otic placode and epidermis," Development, 2006, 133:865-875.

Okubo and Hogan, "Hyperactive Wnt signaling changes the developmental potential of embryonic lung endoderm," Journal of Biology, 2004, 3: 11.

Orford et al., "Differential H3K4 methylation identifies developmentally poised hematopoietic genes," Dev Cell, May 2008, 14(5):798-809.

Oshima et al., "Differential distribution of stem cells in the auditory and vestibular organs of the inner ear," J Assoc Res Otolaryngol., 8:18-31 (Mar. 2007).

Oshima et al., "Mechanosensitive hair cell-like cells from embryonic and induced pluripotent stem cells," Cell, 2010, 141(4): 704-716.

Pagani et al., "Autologous Skeletal Myoblasts Transplanted to Ischemia-Damaged Myocardium in Humans," J. Am. Coll. Cardiol., 41:879-888 (2003).

Pan et al., "Understanding the evolution and development of neurosensory transcription factors of the ear to enhance therapeutic translation," Cell Tissue Res, Jun. 2012, 349:415-432.

Pan et al., "A novel Atoh1 "self-terminating" mouse model reveals the necessity of proper Atoh1 level and duration for hair cell differentiation and viability," PloS One, 2012, 7:e30358.

Pandya et al., "A structural element within the HUWE1 HECT domain modulates self-ubiquitination and substrate ubiquitination activities," The Journal of Biological Chemistry, 2010, 285:5664-5673.

Park et al., "H3K27 Demethylase JMJD3 Employs the NF-kappaB and BMP Signaling Pathways to Modulate the Tumor Microenvironment and Promote Melanoma Progression and Metastasis," Cancer Res, Jan. 2016, 76(1):161-170.

Parker et al., "An independent construct for conditional expression of atonal homolog-1," Human Gene Therapy Methods, 2014, 25:1-13.

Parker et al., "Primary culture and plasmid electroporation of the murine organ of Corti," Journal of Visualized Experiments, 2010.

Parker, "Biotechnology in the treatment of sensorineural hearing loss: foundations and future of hair cell regeneration," Journal of Speech, Language, and Hearing Research, 2011, 54: 1 709-1731.

Patel et al., "The histone demethylase LSD1 regulates inner ear progenitor differentiation through interactions with Pax2 and the NuRD repressor complex, " PLoS One, Jan. 2018, 13(1):e0191689, 20 pages.

Patzel et al., "Design of siRNAs producing unstructured guide-RNAs results in improved RNA interference efficiency," Nature Biotechnol., 23:1440-1444 (2005).

Pauley et al., "Expression and Function of FGF10 in Mammalian Inner Ear Development," Dev. Dyn., 227:203-215 (2003).

Paulson et al., "A Novel Controlled Local Drug Delivery System for Inner Ear Disease," Laryngoscope, Apr. 2008, 118(4):706-11.

Pedersen, "Cells for Medicine," Scientif. Am., 280:68-73 (1999).

Peng et al., "A proteomics approach to understanding protein ubiquitination," Nature Biotechnology, 2003, 21:921-926.

Petit, "Usher syndrome: from genetics to pathogenesis," Annu Rev Genomics Hum Genet., 2:271-97 (2001).

Pickart, "Ubiquitin enters the new millennium," Molecular Cell, Sep. 2001, 8(3):499-504.

Pirvola et al., "Neurotrophic Factors during Inner Ear Development," Curr. Top. Dev. Biol., 57:207-223 (2003).

Pittenger et al., "Multilineage Potential of Adult Human Mesenchymal Stem Cells," Sci., 284:143-147 (1999).

Piu et al., "OTO-104: A Sustained-Release Dexamethasone Hydrogel for the Treatment of Otic Disorders," Otol Neurotol., Jan. 2011, 32(1):171-9.

Plum et al., "Connexin31-deficiency in mice causes transient placental dysmorphogenesis but does not impair hearing and skin differentiation," Dev Biol., 231:334-47 (2001).

Presente et al., "Notch is required for long-term memory in Drosophila," Proc. Nat. Acad. Sci., 101:1764-1768 (2004).

Price, "CKI, there's more than one: casein kinase I family members in Wnt and Hedgehog signaling," Genes & Development, 20: 399-410.

Purow et al., "Expression of Notch-1 and Its Ligands, Delta-Like-1 and Jagged-1, Is Critical for Glioma Cell Survival and Proliferation," Cancer Res., 65:2353-2363 (2005).

Qyang et al., "The renewal and differentiation of Isl 1 + cardiovascular progenitors are controlled by a Wnt/beta-catenin pathway," Cell Stem Cell, 2007, 1: 165-179.

Railo et al., "Genomic response to Wnt signalling is highly context-dependent—evidence from DNA microarray and chromatin immunoprecipitation screens ofWnt/TCF targets," Exp Cell Res, Oct. 2009, 315(26):2690-2704.

Rask-Andersen et al., "Regeneration of human auditory nerve. In vitro/in video demonstration of neural progenitor cells in adult human and guinea pig spiral ganglion," Hear. Res., 203:180-191 (2005).

Ravid and Hochstrasser, "Diversity of degradation signals in the ubiquitin-proteasome system," Nat Rev Mol Cell Biol, 2008, 9(9):679-90.

RCE and Response to Final Office Action issued in U.S. Appl. No. 13/130,607, filed Apr. 21, 2014, 8 pages.

Rena et al., "D4476, a cell-permeant inhibitor of CK1, suppresses the site-specific phosphorylation and nuclear exclusion of FOXO1a," EMBO reports, 2004, 5: 60-65.

Response to Non-Final Office Action issued in U.S. Appl. No. 13/130,607, filed Jul. 19, 2013, 5 pages.

Response to Non-Final Office Action issued in U.S. Appl. No. 13/130,607 on Oct. 23, 2014, filed Apr. 23, 2015 (10 pages).

Response to Restriction Requirement issued in U.S. Appl. No. 13/130,607, filed Dec. 12, 2012, 2 pages.

Response to Restriction Requirement issued in U.S. Appl. No. 13/759,441 on Dec. 22, 2014, filed Mar. 19, 2015 (4 pages).

Response to U.S. Final Office Action in U.S. Appl. No. 13/130,607, dated Jan. 15, 2016, 9 pages.

Restriction Requirement issued in U.S. Appl. No. 13/130,607 on Oct. 12, 2012, 13 pages.

Restriction Requirement issued in U.S. Appl. No. 13/759,441 on Dec. 22, 2014 (4 pages).

Riccomagno et al., "Wnt-dependent regulation of inner ear morphogenesis is balanced by the opposing and supporting roles of Shh," Genes & Development, 2005, 19: 1612-1623.

Roberson et al., "Direct transdifferentiation gives rise to the earliest new hair cells in regenerating avian auditory epithelium," Journal of Neuroscience Research, 2004,7 8: 461-4 71.

Roccio et al., "Cell cycle reactivation of cochlear progenitor cells in neonatal FUCCI mice by a GSK3 small molecule inhibitor," Sci Rep, Dec. 2015, 5: 1-11.

Ross et al., "Basic helix-loop-helix factors in cortical development," Neuron, Jul. 2003, 39: 13-25.

Rotin and Kumar, "Physiological functions of the HECT family of ubiquitin Ligases," Nature Reviews Molecular Cell Biology, 2009, 10:398-409.

Rubel et al., "Mammalian Vestibular Hair Cell Regeneration," Science, Feb. 1995, 267(5198):701-707.

Ryals and Rubel, "Hair Cell Regeneration After Acoustic Trauma in Adult Coturnix Quail," Science, Jun. 1988, 240:1774-1776.

Ryusuke et al., "Pharmacological inhibition of Notch signaling in the mature guinea pig cochlea" Neuroreport, Lippincott Williams and Wilkins, UK, Dec. 2007, 18(18): 1911-1914.

Sakaguchi et al., "Spatiotemporal patterns of Musashi1 expression during inner ear development," Neuroreport, 15:997-1001 (Apr. 29, 2004).

Sakamoto et al., "Inner ear drug delivery system from the clinical point of view," Acta Otolaryngol Suppl., Nov. 2010, 563:101-4.

Sakamoto et al., "Fates of mouse embryonic stem cells transplanted into the inner ears of adult mice and embryonic chickens," Acta Otolarynol Suppl., 551:48-52 (2004).

(56) References Cited

OTHER PUBLICATIONS

Salt and Plontke, "Principles of local drug delivery to the inner ear," Audiol Neurootol., 14:350-60 (2009).

Samarajeewa et al., "Transcriptional response to Wnt activation regulates the regenerative capacity of the mammalian cochlea," Development, Nov. 2018, 145(23):dev166579, 27 pages.

Samon et al., "Preclinical analysis of the γ-secretase inhibitor PF-03084014 in combination with glucocorticoids in T-cell acute lymphoblastic leukemia," Mol Cancer Ther., 11(7):1565-1575 (Jul. 2012).

Samstein and Platt, "Physiologic and immunologic hurdles to xenotransplantation," Journal of American Society of Nephrology, 12:182-193 (2001).

Sarrazin et al., "Proneural gene requirement for hair cell differentiation in the zebrafish lateral line," Dev. Biol., 295:534-545 (2006).

Satoh and Fekete, "Clonal analysis of the relationships between mechanosensory cells and the neurons that innervate them in the chicken ear," Develop., 132:1687-1697 (2005).

Scheffner and Staub, "HECT E3s and human disease," BMC Biochemistry, Nov. 2007, 8 Suppl 1:S6.

Schwarz et al., "Characterization of human hect domain family members and their interaction with UbcH5 and UbcH7," The Journal of Biological Chemistry, 1998, 273: 12148-12154.

Shakoori et al., "Deregulated GSK3b activity in colorectal cancer: Its association with tumor cell survival and proliferation," Biochem and Biophys Research Comm, 2005, 334: 1365-1373.

Shi et al., "Abstract #: 732: Interaction of B-Catenin with an Atoh1 3' Enhancer Upregulates Atoh1 Expression and Increases Differentiation of Progenitors to Hair Cells," ARO 32nd Annual Midwinter Meeting, Baltimore, Maryland, Feb. 14-19, 2009, 3 pages.

Shi et al., "Generation of hair cells in neonatal mice by beta-catenin overexpression in Lgr5-positive cochlear progenitors," PNAS, 2013, 110: 13851-13856.

Shi et al., "Wnt-responsive lgr5-expressing stem cells are hair cell progenitors in the cochlea," J Neurosci, 2012, 32: 9639-9648.

Shi et al., "β-Catenin Up-regulates Atoh1 Expression in Neural Progenitor Cells by Interaction with an Atoh1 3' Enhancer," J Biol Chem, Jan. 2010, 285(1):392-400.

Shi et al., "β-Catenin Is Required for Hair-Cell Differentiation in the Cochlea," The Journal of Neuroscience, 2014, 34:6470-6479.

Skowyra et al., "F-box proteins are receptors that recruit phosphorylated substrates to the SCF ubiquitin-ligase complex," Cell, 1997, 91:209-219.

Sowa et al., "Defining the human deubiquitinating enzyme interaction landscape," Cell, 2009, 138:389-403.

Sparling et al., "Adipocyte-specific blockade of gamma-secretase, but not inhibition of Notch activity, reduces adipose insulin sensitivity," Molecular Metabolism, 2016, 5: 113-121.

Spence et al., "A ubiquitin mutant with specific defects in DNA repair and multiubiquitination," Molecular and Cellular Biology, 1995, 15:1265-1273.

Staecker et al., "Vestibular hair cell regeneration and restoration of balance function induced by math1 gene transfer," Otology & Neurotology, 2007, 28:223-231.

Stahle et al., "Long-term Progression of Meniere's Disease," Acta Otolaryngol, 1991, Suppl. 485: 78-83.

Stallwood et al., "Small Interfering RNA-Mediated Knockdown of Notch Ligands in Primary CD4+ T Cells and Dendritic Cells Enhances Cytokine Production," J. Immunol., 177:885-895 (2006).

Stambolic et al., "Lithium inhibits glycogen synthase kinase-3 activity and mimics Wingless signalling in intact cells," Current Biology, 1996, 6: 1664-1668.

Stevens et al., "Forced activation of Wnt signaling alters morphogenesis and sensory organ identity in the chicken inner ear," Dev. Biol, 2003, 261: 149-164.

Stojanova et al., "Epigenetic regulation of Atoh1 guides hair cell development in the mammalian cochlea," Development, 2015, 142(20):3529-3536.

Stone and Cotanche, "Identification of the timing of S phase and the patterns of cell proliferation during hair cell regeneration in the chick cochlea," The Journal of Comparative Neurology, 1994, 341:50-67.

Subramanian et al., "Gene set enrichment analysis: a knowledge-based approach for interpreting genome wide expression profiles," PNAS, Oct. 2005, 102(43):15545-15550.

Sumitran et al., "Porcine Embryonic Brain Cell Cytotoxicity Mediated by Human Natural Killer Cells," Cell Transplantation, 1999, 601-610.

Sun et al., "Histone demethylase LSD1 regulates neural stem cell proliferation," Mol Cell Biol, Apr. 2010, 30(8):1997-2005.

Supplementary European Search Report issued in EP09828380 on Nov. 30, 2012 (8 pages).

Swan et al., "Inner ear drug delivery for auditory applications," Advanced Drug Delivery Reviews, 2008, 60: 1583-1599.

Sziklai et al., "Otosclerosis: an organ-specific inflammatory disease with sensorineural hearing loss," Eur. Arch. Otorhinolaryngol., 2009, 266:1711-1718.

Tai and Schuman, "Ubiquitin, the proteasome and protein degradation in neuronal function and dysfunction," Nature Reviews Neuroscience, 2008, 9:826-838.

Takebayashi et al., "Multiple roles of Notch signaling in cochlear development," Developmental Biology, 2007, 307: 165-178.

Tamura et al., "Drug Delivery to the Cochlea Using PLGA Nanoparticles," Laryngoscope, Nov. 2005, 115(11):2000-5.

Tan et al., "Parallel SCF adaptor capture proteomics reveals a role for SCFFBXL1 7 in NRF2 activation via BACH1 repressor turnover," Molecular Cell, 2013, 52:9-24.

Tiveron et al., "Role of Phox2b and Mash1 in the generation of the vestibular efferent nucleus," Developmental Biology, 2003, 260:46-57.

Tsuchiya et al., "Reciprocal targeting ofHath1 and beta-catenin by Wnt glycogen synthase kinase 3beta in human colon cancer," Gastroenterology, 2007, 132:208-220.

U.S. Final Office Action in U.S. Appl. No. 13/130,607, dated Jan. 15, 2016, 26 pages.

Varshavsky, "Naming a targeting signal," Cell, 1991, 64:13-15.

Vats et al, "Stem cells: sources and applications," Clin. Otoaryngol, 2002, 27:227-232.

Vierbuchen et al., "Direct conversion of fibroblasts to functional neurons by defined factors," Nature, 463:1035-41 (Feb. 25, 2010).

Wagers et al., "Little Evidence for Developmental Plasticity of Adult Hematopoietic Stem Cells," Science, 297:2256-2259 (2002).

Wagner and Jung, "New lysine methyltransferase drug targets in cancer," Nature Biotechnology, 2012, 30:622-623.

Wang et al., "Dose-dependent sustained release of dexamethasone in inner ear cochlear fluids using a novel local delivery approach," Audiol Neurootol., 2009, 14(6):393-401.

Wang et al., "LSD1 co-repressor Rcor2 orchestrates neurogenesis in the developing mouse brain," Nat Commun, Jan. 2016, 7:10481, 14 pages.

Wang et al., "Principles of inner ear sustained release following intratympanic administration," Laryngoscope, Feb. 2011, 121(2):385-91.

Wang et al., "Cell fusion is the principal source of bone-marrow-derived hepatocytes," Nature, 422:897-901 (2003).

Wang et al., "Dynamics of noise-induced cellular injury and repair in the mouse cochlea," J Assoc Res Otolaryngol., 3:248-68 (Sep. 2002).

Wang et al., "HUWE1 interacts with BRCA1 and promotes its degradation in the ubiquitin-proteasome pathway," Biochemical and Biophysical Research Communications, 2013.

Warchol et al., "Regenerative proliferation in inner ear sensory epithelia from adult guinea pigs and humans," Science, 1993, 259: 1619-1622.

Warner et al., "Expression of ZIC Genes in the Development of the Chick Inner Ear and Nervous System," Dev. Dyn., 226:702-712 (2003).

Watanabe et al., "Conditioned mesenchymal stem cells produce pleiotropic gut trophic factors," J Gastroenterol, 2014, 49:270-282, 13 pages.

(56)            References Cited

OTHER PUBLICATIONS

Web.Stanford.Edu [online], "Wnt Target genes," 2018, retrieved on Sep. 9, 2022, retrieved from URL<web.stanford.edu/group/nusselab/cgi-bin/wnt/target_genes>, 4 pages.

Weimann et al., "Contribution of transplanted bone marrow cells to Purkinje neurons in human adult brains," Proc. Natl. Acad. Sci. U.S.A., 100:2088-2093 (2003).

White et al., "Mammalian cochlear supporting cells can divide and trans-differentiate into hair cells," Nature, 441:984-987 (2006).

Whyte et al., "Enhancer decommissioning by LSD1 during embryonic stem cell differentiation," Nature, Feb. 2012, 482(7384):221-225.

Wislet-Gendebien et al., "Plasticity of cultured mesenchymal stem cells: switch from nestin-positive to excitable neuron-like phenotype," Stem Cells, 2005, 23:392-402.

Wolfe, "γ-secretase Inhibition and Modulation for Alzheimer's Disease," Curr Alzheimer Res., 5(2):158-164 (Apr. 2008) (Author Manuscript).

Wong et al., "Chronic treatment with the gamma-secretase inhibitor L Y-411,575 inhibits beta-amyloid peptide production and alters lymphopoiesis and intestinal cell differentiation," J Biol Chem., 279:12876-82 (Mar. 26, 2004).

Woods et al., "Math1 regulates development of the sensory epithelium in the mammalian cochlea," Nat. Neurosci., 7:1310-1318 (2004).

Written Opinion of the International Searching Authority for PCT/US2009/065747, mailed Apr. 8, 2010, 3 pages.

Written Opinion of the International Searching Authority issued in corresponding International Application No. PCT/US2007/84654, mailed Oct. 3, 2008, 5 pages.

Wu et al., "A systematic survey of carbonic anhydrase mRNA expression during mammalian inner ear development," Dev Dyn, Mar. 2013, 242(3):269-280.

Wu et al., "Structure of a beta-TrCP 1-Skp 1-beta-catenin complex: destruction motif binding and lysine specificity of the SCF(beta-TrCP 1) ubiquitin ligase," Molecular Cell, 2003, 11:1445-1456.

Xia et al., "Ototoxicity of cisplatin administered to guinea pigs via the round window membrane," J Toxicol Sci., 2012, 37(4):823-830.

Yamada et al., "Rest promotes the early differentiation of mouse ESCs but is not required for their maintenance," Cell Stem Cell, Jan. 2010, 6(1):10-15.

Yamamoto et al., "Inhibition of Notch/RBP-J signaling induces hair cell formation in neonate mouse cochleas," J. Mol. Med., 84(1):37-45 (Jan. 2006).

Yang et al., "EGb 761 (Ginkgo biloba) protects cochlear hair cells against ototoxicity induced by gentamicin via reducing reactive oxygen species and nitric oxide-related apoptosis," J Nutr Biochem., 2011, 22:886-894.

Yang et al., "E3 ubiquitin ligase Mule ubiquitinates Miz1 and is required for TNFalphainduced INK activation," PNAS, 2010, 107:13444-13449.

Yang et al., "Generation and characterization of Atoh1-Cre knock-in mouse line," Genesis, 2010, 48:407-413.

Yang et al., "Requirement of Math 1 for Secretory Cell Lineage Commitment in the Mouse Intestine," Science, 2001, 294:2155.

Ye et al., "Recognition of phosphodegron motifs in human cyclin E by the SCF(Fbw7) ubiquitin ligase," The Journal of biological chemistly, 2004, 279:50110-50119.

Yoneda, "Attempt to regenerate cochlear morphology and function using gene transfer," Otol. Jpn., May 2006, 16(2):135-138 (with machine translation).

Zaragosi et al., "Effects of GSK3 inhibitors on in vitro expansion and differentiation of human adipose-derived stem cells into adipocytes," BMC Cell Biology, 2008, 9: 11.

Zhang et al., "Gene regulatory networks mediating canonical Wnt signal-directed control of pluripotency and differentiation in embryo stem cells," Stem Cells, 2013, 31(12):2667-79.

Zhang et al., "Mule determines the apoptotic response to HDAC inhibitors by targeted ubiquitination and destruction ofHDAC2," Genes & Development, 2011, 25:2610-2618.

Zhao et al., "The HECT-domain ubiquitin ligase Huwel controls neural differentiation and proliferation by destabilizing the N-Myc oncoprotein," Nature Cell Biology, 2008, 10:643-653.

Zhao et al., "The N-Myc-DLL3 cascade is suppressed by the ubiquitin ligase Huwel to inhibit proliferation and promote neurogenesis in the developing brain," Developmental Cell, 2009, 17:210-221.

Zheng and Gao, "Overexpression of Math1 induces robust production of extra hair cells in postnatal rat inner ears," Nat. Neurosci., 2000, 3:580-586.

Zheng et al., "Induction of Cell Proliferation by Fibroblast and Insulin-Like Growth Factors in Pure Rat Inner Ear Epithelial Cell Cultures," J. Neurosci., 17:216-226 (1997).

Zhong et al., "Mule/ARF-BP1, a BH3-only E3 ubiquitin ligase, catalyzes the polyubiquitination of Mcl-1 and regulates apoptosis," Cell, 2005, 21:1085-1095.

Zhou et al., "Nuclear GSK3β promotes tumorigenesis by phosphorylating KDM1A and inducing its deubiquitylation by USP22," Nat Cell Biol, Sep. 2016, 18(9):954-966, 28 pages.

Zibetti et al., "Alternative splicing of the histone demethylase LSD1/KDM1 contributes to the modulation of neurite morphogenesis in the mammalian nervous system," J Neurosci, Feb. 2010, 30(7):2521-2532.

Zine et al., "Hes1 and Hes5 activities are required for the normal development of the hair cells in the mammalian inner ear," J Neurosci., 21:4712-20 (Jul. 1, 2001).

Zine et al., "Notch signaling regulates the pattern of auditory hair cell differentiation in mammals," Development., 2000, 127:3373-3383.

Costa et al., "Atoh1 in sensory hair cell development: constraints and cofactors," Seminars in Cell & Developmental Biology, May 2017, 65:60-68.

Arnold et al., "Sox2⁺ adult stem and progenitor cells are important for tissue regeneration and survival of mice," Cell Stem Cell, Oct. 2011, 9(4):317-29.

Cohen-Salmon et al., "Targeted ablation of connexin26 in the inner ear epithelial gap junction network causes hearing impairment and cell death," Curr Biol., Jul. 2002, 12(13):1106-11.

Elgoyhen and Franchini, "Prestin and the cholinergic receptor of hair cells: positively-selected proteins in mammals," HHS Public Access Author Manuscript, doi: 10.1016/j.heares.2009.12.028, published online Jan. 6, 2010, published in final edited form as: Hear Res, Mar. 2011, 273(1-2):100-8, 19 pages.

Fritzsch et al., "The molecular basis of neurosensory cell formation in ear development: a blueprint for hair cell and sensory neuron regeneration?," Bioessays, Dec. 2006, 28(12):1181-93, 13 pages.

Fujioka et al., "Generating mouse models of degenerative diseases using ere/lox-mediated in vivo mosaic cell ablation," J Clin Invest, Jun. 2011, 121(6):2462-9.

Harding et al., "The effect of an age-related hearing loss gene (Ah1) on noise-induced hearing loss and cochlear damage from low-frequency noise," Hear Res, Jun. 2005, 204(1-2):90-100, 5 pages (Abstract only).

Hudspeth, "Making an effort to listen: mechanical amplification in the ear," Neuron, Aug. 2008, 59(4):530-45.

Kujawa and Liberman, "Conditioning-related protection from 15 acoustic injury: effects of chronic deefferentation and sham surgery," J Neurophysiol, Dec. 1997, 78(6):3095-106.

Löwenheim et al., "Gene disruption of p27$^{Kip1}$ allows cell 15 proliferation in the postnatal and adult organ of corti," Proc Natl Acad Sci U S A, Mar. 1999, 96(7):4084-8.

Maison et al., "Loss of αCGRP reduces sound-evoked activity in the cochlear nerve," J Neurophysiol, Nov. 2003, 90(5):2941-9.

Mantela et al., "The retinoblastoma gene pathway regulates the postmitotic state of hair cells of the mouse inner ear," Development, May 2005, 132(10):2377-2388.

Martinez-Monedero et al., "Differentiation of inner ear stem cells to functional sensory neurons," Dev Neurobiol., Apr. 2008, 68(5):669-684.

Muzumdar et al., "A global double-fluorescent Cre reporter mouse," Genesis, Sep. 2007, 45(9):593-605.

Nayak et al., "Development of the hair bundle and mechanotransduction," Int J Dev Biol., 2007, 51(6-7):597-608.

(56) References Cited

OTHER PUBLICATIONS

Richardson et al., "How the genetics of deafness illuminates auditory physiology," Annu Rev Physiol., 2011, 73:311-34.

Sage et al., "Essential role of retinoblastoma protein in mammalian hair cell development and hearing," Proc Natl Acad Sci U S A, May 2006, 103(19):7345-50.

Sage et al., "Proliferation of functional hair cells in vivo in the absence of the retinoblastoma protein," Science, Feb. 2005, 307(5712):1114-8.

Warchol, "Sensory regeneration in the vertebrate inner ear: Differences at the levels of cells and species," Hear Res, Mar. 2011, 273(1-2):72-9, 5 pages (Abstract only).

Office Action in Korean Appln. No. 10-2018-7024892, dated Sep. 19, 2024, 30 pages (with English translation).

Romand et al., "The retinoic acid receptors RARα and RARγ are required for inner ear development," Mechanisms of Development, Dec. 2002, 119(2):213-223.

Mimasu et al., "Structurally designed trans-2-phenylcyclopropylamine derivatives potently inhibit histone demethylase LSD1/KDM1," Biochemistry, Aug. 2010, 49(30):6494-6503.

Agrup et al., "The inner ear and the neurologist," J Neurol Neurosurg Psychiatry, Feb. 2007, 78(2):114-22.

Massari et al., "Helix-loop-helix proteins: regulators of transcription in eucaryotic organisms," Molecular and Cellular Biology, Jan. 2000, 20(2):429-40.

Park et al., "Zath3, a neural basic helix-loop-helix gene, regulates early neurogenesis in the zebrafish," Biochemical and Biophysical Research Communications, Aug. 2003, 308(1):184-90.

Segev et al., "Nato3 is an evolutionarily conserved bHLH transcription factor expressed in the CNS of Drosophila and mouse," Mechanisms of Development, Aug. 2001, 106(1-2):197-202.

EP Brief Communication in European Appln. No. 13836099.5, dated Jan. 19, 2021, 9 pages.

EP Extended Search Report in EP Appln. No. 17744987.3, dated Jul. 3, 2019, 9 pages.

EP Office Action in European Appln. No. 17744987, dated May 14, 2020, 3 pages.

JP Office Action in Japanese Application No. 2017-132839, dated Jun. 18, 2019, 10 pages (with English translation).

JP Office Action in Japanese Appln. No. 2015-531223, dated Sep. 11, 2019, 5 pages (with English translation).

JP Office Action in Japanese Appln. No. 2015-531223, dated Jan. 5, 2021, 20 pages (with English translation).

JP Office Action in Japanese Appln. No. 2018-540010, dated Mar. 2, 2021, 6 pages (with English translation).

JP Office Action in Japanese Appln. No. 2019-091552, dated Apr. 28, 2020, 8 pages (with English translation).

JP Office Action in Japanese Appln. No. 2019-228284, dated Jan. 26, 2021, 5 pages (with English translation).

* cited by examiner

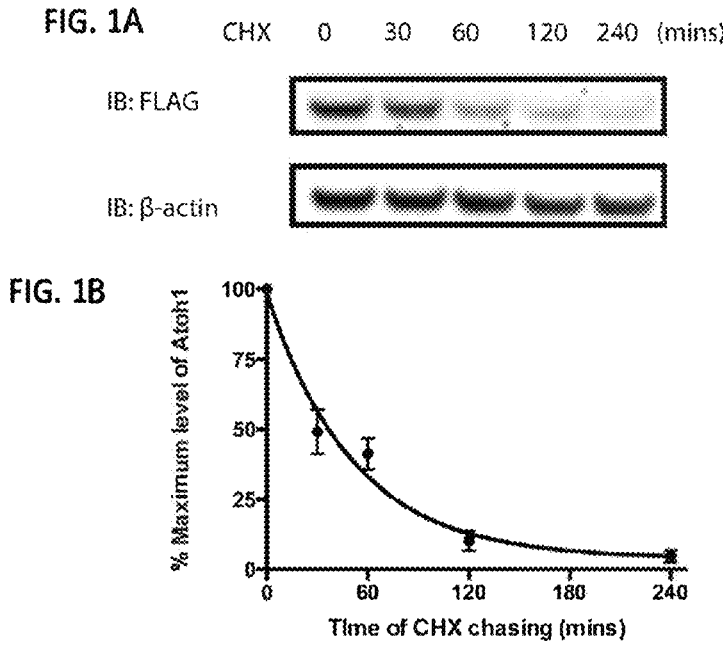
FIG. 1A
FIG. 1B
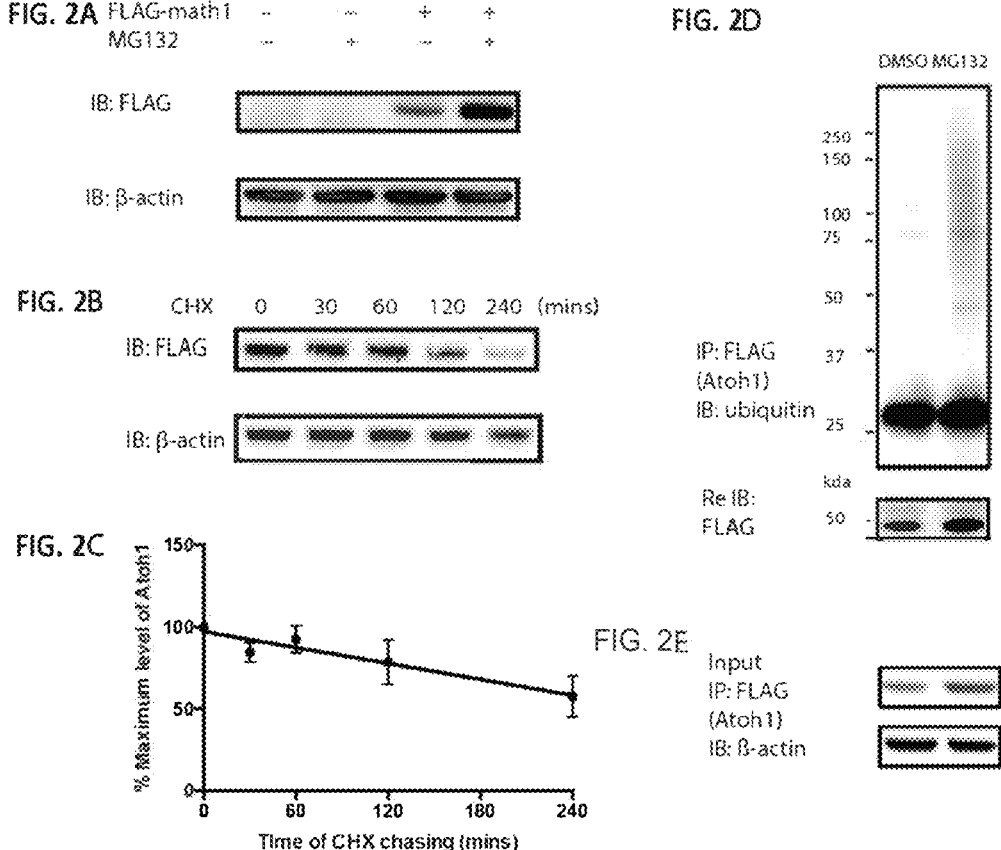
FIG. 2A
FIG. 2B
FIG. 2C
FIG. 2D
FIG. 2E

Huwe1 ⟶

Atoh1 ⟶

~460
~250
~170
~100
~70
~55
~40
~30
(kda)

FLAG-HA-Atoh1 293T     293T
           IP               IP

10% input  blank  IgG  HA  bank  IgG  HA

IB: HUWE1

Re IB: HA (Atoh1)

IP

10% input    IgG    HUWE1

IB: HA (Atoh1)

Re IB: HUWE1

FIG. 8A
| HA-Ubi_WT | + | + | + | – | – | – | + |
| HA-Hbi_K48 | – | – | – | + | + | + | – |
| Huwe1_WT | – | + | – | – | + | – | + |
| Huwe1_C4341S | – | – | + | – | – | + | – |
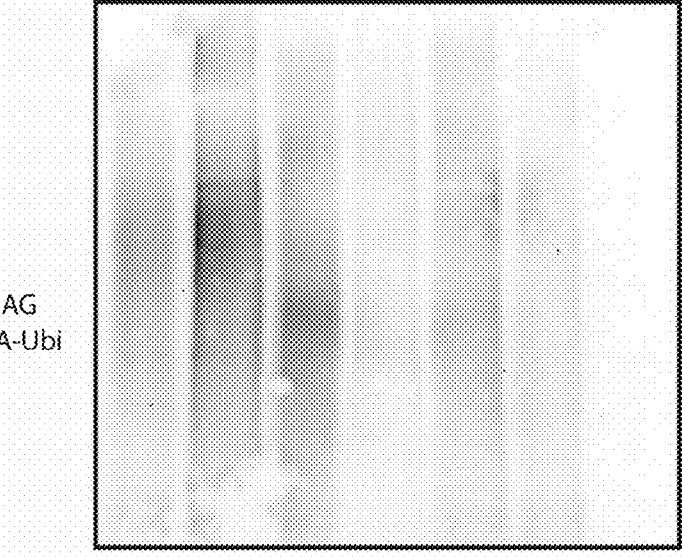
IP: FLAG
IB: HA-Ubi
IP: FLAG           IP: IgG
Re-blot
IB: FLAG
Re-blot
IB: Huwe1
FIG. 8B
5% input
| HA-Ubi_WT | + | + | + | – | – | – |
| HA-Hbi_K48 | – | – | – | + | + | + |
| Huwe1_WT | – | + | – | – | + | – |
| Huwe1_C4341S | – | – | + | – | – | + |
Myc (Huwe1)
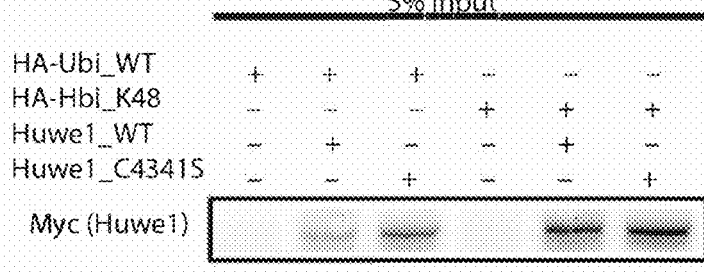
FLAG (Atoh1)
β-actin

FIG. 9A
FIG. 9B
control pHUWE1
shRNA scrambled HUWE1
FLAG (ATOH1)
1    0.56
HUWE1
1    1.82
ß-actin
FLAG (ATOH1)
1    2.44
HUWE1
1    0.53
ß-actin
FIG. 9C
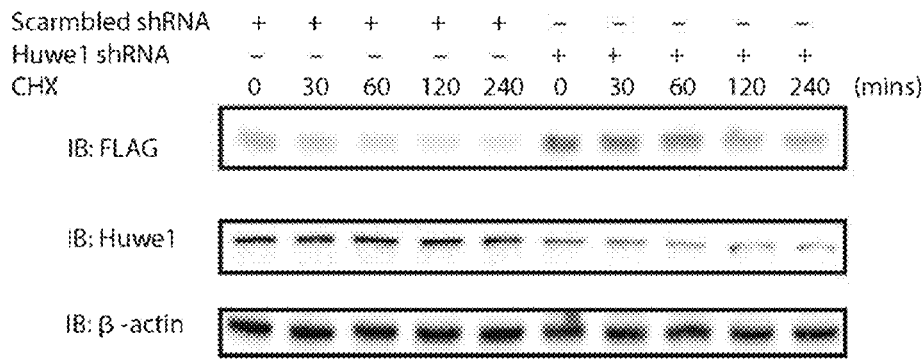
Scarmbled shRNA  +  +  +  +  +  −  −  −  −  −
Huwe1 shRNA    −  −  −  −  −  +  +  +  +  +
CHX    0  30  60  120  240  0  30  60  120  240  (mins)
IB: FLAG
IB: Huwe1
IB: β -actin
FIG. 9D
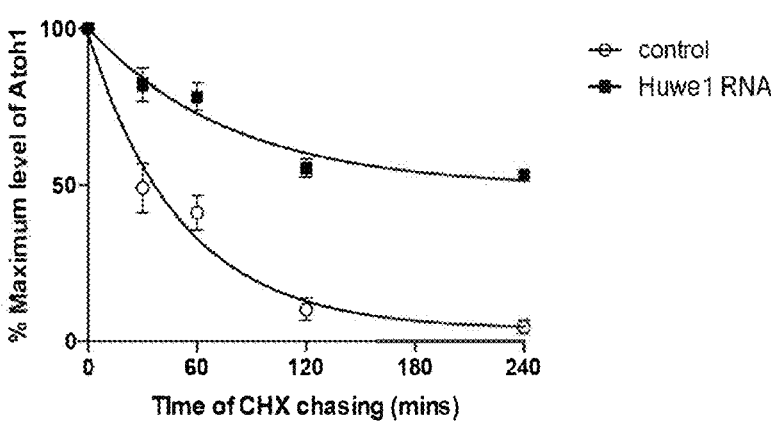
-o- control
-■- Huwe1 RNAi
% Maximum level of Atoh1
Time of CHX chasing (mins)

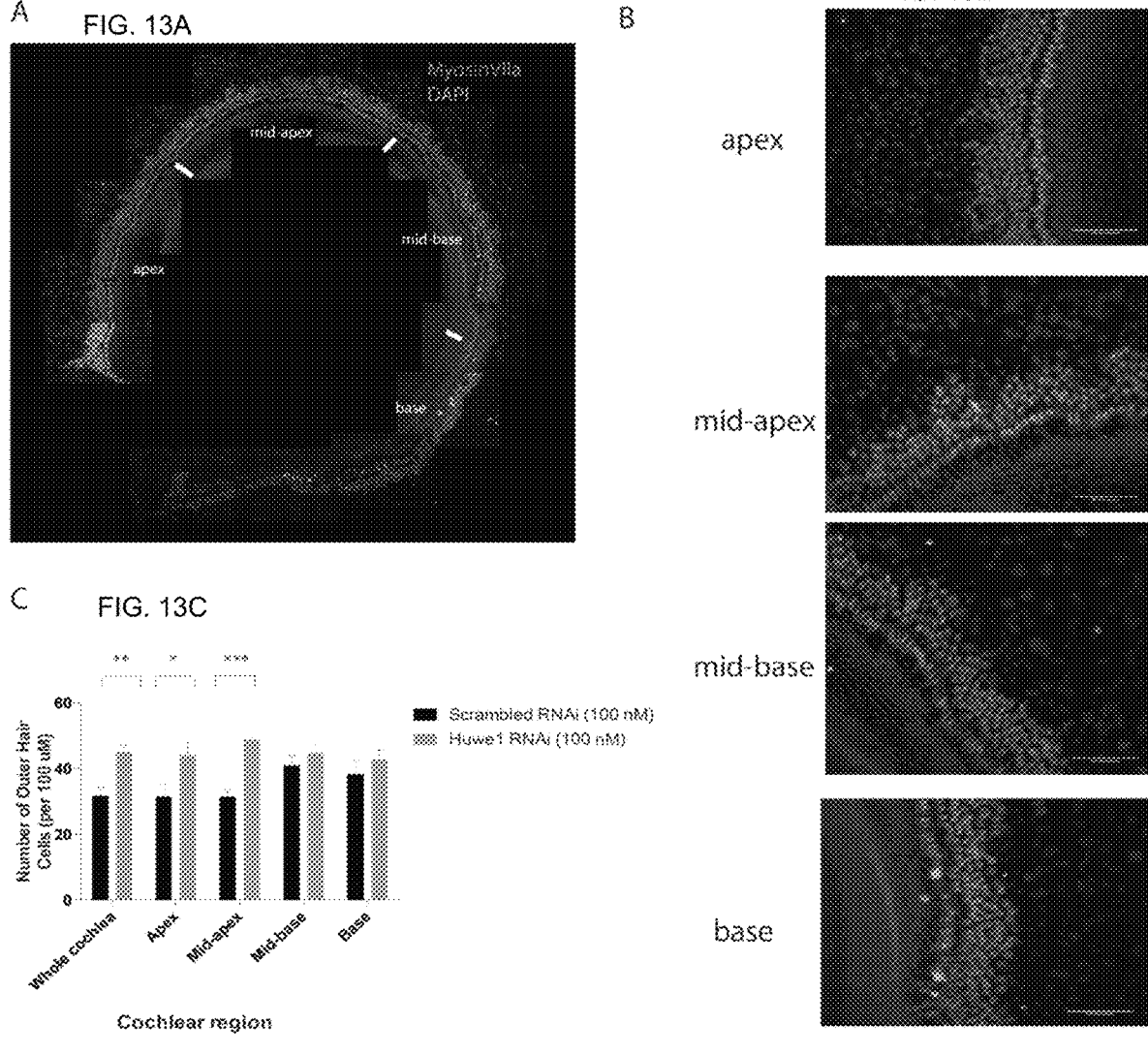
A  FIG. 13A
B  FIG. 13B
C  FIG. 13C

MyosinVIIa / CtBP2 / GluR2
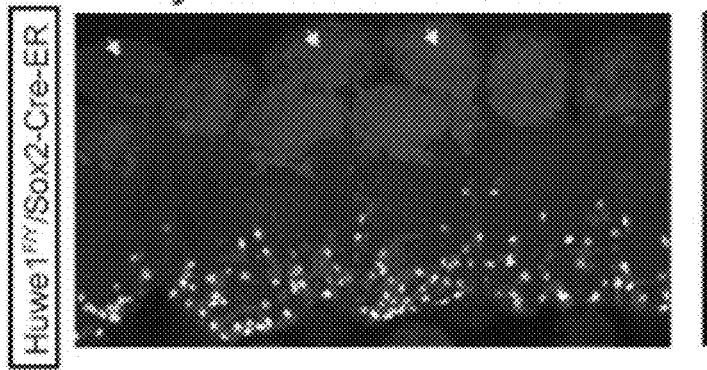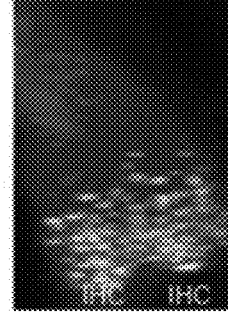
FIG. 16C
MyosinVIIa / CtBP2 / GluR2
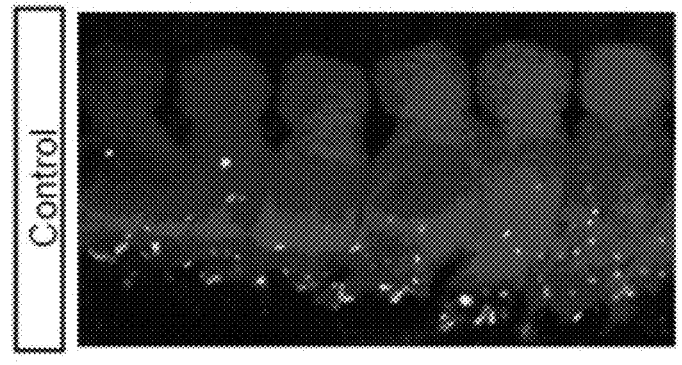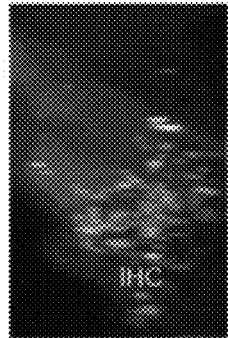
FIG. 16D
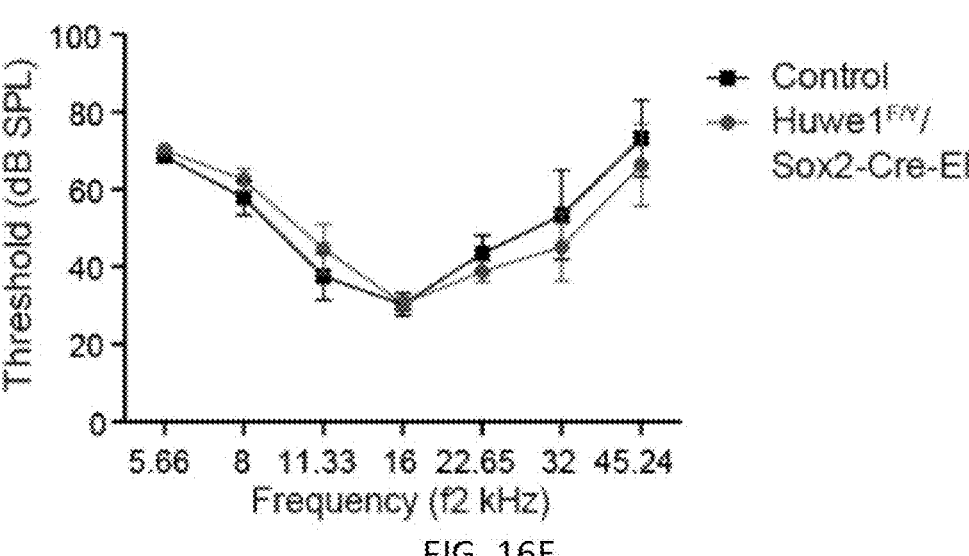
FIG. 16E

INCREASING ATOH1 LIFE TO DRIVE SENSORINEURAL HAIR CELL DIFFERENTIATION

CROSS-REFERENCE TO RELATED APPLICATIONS

This application is a divisional of U.S. patent application Ser. No. 16/358,579, filed Mar. 19, 2019, which is a continuation of U.S. patent application Ser. No. 15/502,113, filed Feb. 6, 2017, now abandoned, which is a 371 U.S. National of PCT Application No. PCT/US2015/043976, filed on Aug. 6, 2015, which claims priority to U.S. Patent Application Ser. No. 62/034,040, filed on Aug. 6, 2014; and U.S. Patent Application Ser. No. 62/034,459, filed on Aug. 7, 2014, the entire contents of which applications are incorporated herein by reference.

SEQUENCE LISTING

This application contains a Sequence Listing that has been submitted electronically as an ASCII text file named "Sequence_Listing.txt." The ASCII text file, created on Mar. 2, 2022, is 10 kilobytes in size. The material in the ASCII text file is hereby incorporated by reference in its entirety.

TECHNICAL FIELD

This invention relates to the generation of sensorineural hair cells, and more particularly to the use of modulation of Atoh1 expression to generate sensorineural hair cells.

BACKGROUND

There are six distinct sensory organs in the mammalian inner ear: the three cristae of the semicircular canals, the two maculae of the saccule and utricle, and the organ of Corti of the cochlea. The organ of Corti is the organ of hearing. The receptor cell for hearing is the hair cell of the cochlea (referred to herein as a hair cell, a sensory hair cell, or a sensorineural hair cell). Hair cells are limited in number and do not regenerate in mammals; damage or death of these cells leads to hearing loss (Edge and Chen, Curr. Opin. Neurobiol., 18:377-382 (2008)). Therapeutic compositions and methods to increase sensorineural hair cell number and/or function in the cochlea are required to address hearing loss.

SUMMARY

The present disclosure provides compositions and methods for generating hair cells by modulating expression of Atoh1 by inhibiting proteasome degradation of the Atoh1 protein. The data presented herein shows a role of the ubiquitin proteasome pathway in post-translational regulation of Atoh1, identifies several amino acids in the N terminus as important in determining lifespan of the Atoh1 protein, and identifies the HECT, UBA and WWE domain containing 1 (Huwe1) protein as an E3 ubiquitin ligase for Atoh1.

Thus, in a first aspect the invention provides methods for treating a disorder, e.g., sensorineural hearing loss or vestibular dysfunction, associated with loss of auditory hair cells in a subject. The methods include administering a therapeutically effective amount of proteasome inhibitor to the subject, e.g., to the inner ear of the subject. Also provided herein is the use of a proteasome inhibitor for the treatment of sensorineural hearing loss associated with loss of auditory hair cells in a subject.

In some embodiments, the proteasome inhibitor is selected from the group consisting of Bortezomib, Carfilzomib, NPI-0052, MLN9708, CEP-18770, and ONX0912.

In some embodiments, the methods include comprising administering an HDAC inhibitor, an EZH2/HMT inhibitor, or a DNMT inhibitor, in combination with a proteasome inhibitor, to the subject, e.g., to the inner ear of the subject.

Also provided herein is the use of one or more of an HDAC inhibitor, an EZH2/HMT inhibitor, or a DNMT inhibitor, in combination with a proteasome inhibitor, for the treatment of sensorineural hearing loss associated with loss of auditory hair cells in a subject.

In some embodiments, the HDAC inhibitor is selected from the group consisting of: Sodium Butyrate, Trichostatin A, hydroxamic acids, cyclic tetrapeptides, trapoxin B, depsipeptides, benzamides, electrophilic ketones, aliphatic acid compounds, phenylbutyrate, valproic acid, hydroxamic acids, vorinostat (SAHA), belinostat (PXD101), LAQ824, panobinostat (LBH589), entinostat (MS275), romidepsin, C1994, and mocetinostat (MGCD0103). In some embodiments, the EZH2/HMT inhibitor is selected from the group consisting of Deazaneplanocin A; GSK J1; GSK126; EPZ005687; E7438; EI1 (Qi et al., 2012, supra); EPZ-6438; GSK343; BIX-01294, UNC0638, BRD4770, EPZ004777, AZ505 and PDB 4e47, and those described in Garapaty-Rao et al., Chem. Biol. 20(11):1329-1339 (2013); 20130303555; and WO2012/005805; see, e.g., Wagner and Jung, Nature Biotechnology 30:622-623(2012). In some embodiments, the DNMT inhibitor is selected from the group consisting of azacytidine, decitabine, Zebularine (1-((3-D-ribofuranosyl)-1,2-dihydropyrimidin-2-one), procainamide, procaine, (−)-epigallocatechin-3-gallate, MG98, hydralazine, RG108, and Chlorogenic acid. In some embodiments, the proteasome inhibitor is selected from the group consisting of Bortezomib, Carfilzomib, NPI-0052, MLN9708, CEP-18770, and ONX0912.

In some embodiments, the methods uses include application of the HDAC inhibitor, DNMT inhibitor, the EZH2/HMT inhibitor, or the proteasome inhibitor, to the round window membrane, e.g., intra-tympanic injection, intra-labyrinthine delivery, or direct delivery into the inner ear fluids, e.g., using a microfluidic device or infusion pump.

In another aspect, the invention provides long-lived human Atoh1 variant polypeptides comprising mutations at amino acids 328, 331, and/or 334.

In some embodiments, the long-lived human Atoh1 variant polypeptide is at least 80% identical to SEQ ID NO:1.

In some embodiments, the long-lived human Atoh1 variant polypeptide comprises SEQ ID NO:1 with a mutation selected from the group consisting of S328A, S331A, S334A, S328A/S331A, S328A/S331A, S331A/S334A, and S328A/S331A/S334A.

In some embodiments, the long-lived human Atoh1 variant polypeptide comprises SEQ ID NO:1 with a mutation at 5334, e.g., S334A.

In another aspect, the invention provides nucleic acids encoding the long-lived human Atoh1 variant polypeptides described herein, and expression vectors comprising the nucleic acids; in some embodiments, the nucleic acid encoding the long-lived human Atoh1 variant polypeptide is operably linked with an inducible promoter or a tissue specific promoter, e.g., a Lgr5, GFAP, Sox2, p27Kip, FGFR3, Prox1, or Sox2 promoter. Also provided are cells and transgenic animals harboring the nucleic acids and optionally expressing the long-lived human Atoh1 variant polypeptide comprises.

In a further aspect, the invention provides methods for treating a subject suffering from a disorder, e.g., sensorineural hearing loss or vestibular dysfunction, associated with loss of auditory hair cells. The methods include administering a therapeutically effective amount of a nucleic acid encoding a long-lived human Atoh1 variant polypeptide described herein to the subject, e.g., to the inner ear of the subject.

In yet another aspect, the invention features methods for treating a subject suffering from a disorder, e.g., sensorineural hearing loss or vestibular dysfunction, associated with loss of auditory hair cells. The methods include administering a therapeutically effective amount of an inhibitory nucleic acid targeting Huwe1 to the subject, e.g., to the inner ear of the subject. In some embodiments, the inhibitory nucleic acid is selected from the group consisting of antisense oligonucleotides; small interfering RNA (siRNA); and short, hairpin RNA (shRNA).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-B. Atoh1 is a short-lived protein. (A) FLAG-HA-Atoh1 293T cells were treated with cycloheximide (100 ug/ml) and harvested at the indicated times. Lysates were processed for Western blotting with FLAG antibody (Atoh1) or β-actin antibody (loading control). Labels indicate the time of chase. (B) Protein half-lives based on densitometry. The ratio of Atoh1 to β-actin was plotted after normalizing to the initial ratio set to 100. Error bars indicate SEM.

FIGS. 2A-E. Atoh1 is degraded by the ubiquitin-proteasome pathway. (A) Proteasome inhibitor stabilized Atoh1 expression in HEK cell. HEK cells were transfected with FLAG-Atoh1 plasmid (1 ug/ml) for 24 hours, and incubated with either DMSO or MG132 (10 uM) for 3 hours and immunoprecipitated using FLAG (Atoh1) or beta-actin (loading control) antibodies. (B) FLAG-HA-Atoh1 293T cells were treated with cycloheximide (100 ug/ml) and MG132 (10 uM) at the indicated times and immunoprecipitated with FLAG (Atoh1) or beta-actin (loading control) antibodies. Time of treatment is indicated. (C) Half-lives based on densitometry from 3 experiments are shown. The ratio of Atoh1 to β-actin was plotted after normalization. Error bars indicate SEM. (D) & (E). Atoh1 is polyubiquitylated and degraded by the ubiquitin-proteasome pathway. FLAG-HA-Atoh1 293T cells were treated with either DMSO or MG132 (10 uM) for 6 hours. Lysates were immunoprecipitated with anti-FLAG antibody and subjected to immunoblotting with a ubiquitin antibody. FLAG was used to assess immunoprecipitation. MG132 treatment increased the density of the poly-ubiquitin chains of Atoh1, and increased the level of protein as seen both by reprobing the blot and assessing the input protein (E). β-actin is a loading control.

FIGS. 8A-B. Cysteine at position 4341 of Huwe1 is critical for ubiquitin transfer to Atoh1. (A) Wild-type, but not C4341A-mutant Huwe1, promotes polyubiquitylation of Atoh1. HeLa cells were co-transfected with FLAG-Atoh1, HA-ubiquitin (WT) or mutant lysine 48 only (K48), and Myc-Huwe1 WT or C4341A plasmids. FLAG-Atoh1 was immunoprecipitated under denaturing conditions using anti-FLAG antibody, and polyubiquitylation of Atoh1 and total Atoh1 level were detected by Western blotting with anti-HA and anti-FLAG antibodies. Exogenous Huwe1 level was determined with an anti-Myc antibody. The lysates were immunoprecipitated with IgG as a control. (B) Five percent of total extracts from the experiment shown in A were analyzed by Western blot with an anti-Myc antibody to detect exogenous Huwe1 and an anti-FLAG antibody; anti-β-actin was used as a loading control.

FIGS. 9A-D. Huwe1 plasmid increased and Huwe1 siRNA inhibited degradation of Atoh1. (A) FLAG-HA-Atoh1 293T cells were transfected with Huwe1 for 48 hours. Quantification of Atoh1, Huwe1 and a loading control (HSC70) were performed by Western blotting and densitometry. (B) FLAG-HA-Atoh1 293T cells were transfected with Huwe1 shRNA for 72 hours. (C) & (D). The half-life of Atoh1 was increased by Huwe1 knockdown. FLAG-HA-Atoh1 293T cells were transfected with either control or Huwe1 shRNA for 72 hours, and treated with cycloheximide (CHX) for the indicated times. Atoh1 (FLAG) and Huwe1 were analyzed by Western blotting and densitometry normalized to loading controls in three experiments. The ratio of Atoh1 to β-actin was plotted. Error bars indicate SEM.

FIGS. 13A-C. Huwe1 knockdown increases hair cell generation in organ of Corti explants. (A) & (B). Organs of Corti treated with Huwe1 siRNA (100 nM) for 72 hours have increased numbers of hair cells in the apex (0-25%), mid-apex (25-50%), mid-base (50-75%), and base (75-100%). (C) Outer hair cell counts in the apex, mid-apex, mid-base, and base or the whole cochlea (mean±SEM per 100 mm; *p<0.05, p<0.01 *p<0.001, n=7 for both groups).

FIGS. 16A-F. An extra row of inner hair cells in Huwe1 conditional knockout mice (A) E18.5 organ of Corti from conditional knockout of Huwe1 at E15.5. Additional inner hair cells can be seen throughout the cochlea after knockout of Huwe1 in Sox2-positive supporting cells at E15.5. Myosin VIIa labels hair cells and Sox2 labels supporting cells; DAPI is a nuclear marker. The white line marks the location of the orthogonal view shown beneath the surface view, and yellow and white brackets indicate inner and outer hair cells, respectively. Arrows point to extra inner hair cells. The scale bar is 25 μm. (B) E18.5 organ of Corti from Sox2-Cre control mice showing a single row of inner hair cells. (C), (D) Z- (left) and X- (right) projection confocal images of the inner hair cell region in the P30 organ of Corti from a Huwe1 conditional knockout (C) or control (D) ear. Deletion of Huwe1 was performed at P2. The cochleas were immunostained with antibodies against myosin VIIa, CtBP2 and GluR2. Arrows indicate extra inner hair cells. (E), (F) Thresholds recorded at P30 from Huwe1 conditional knockout (n=3) and control (n=5) ears for DPOAE (E) and ABR (F). Error bars indicate SEM.

DETAILED DESCRIPTION

Figure 3:
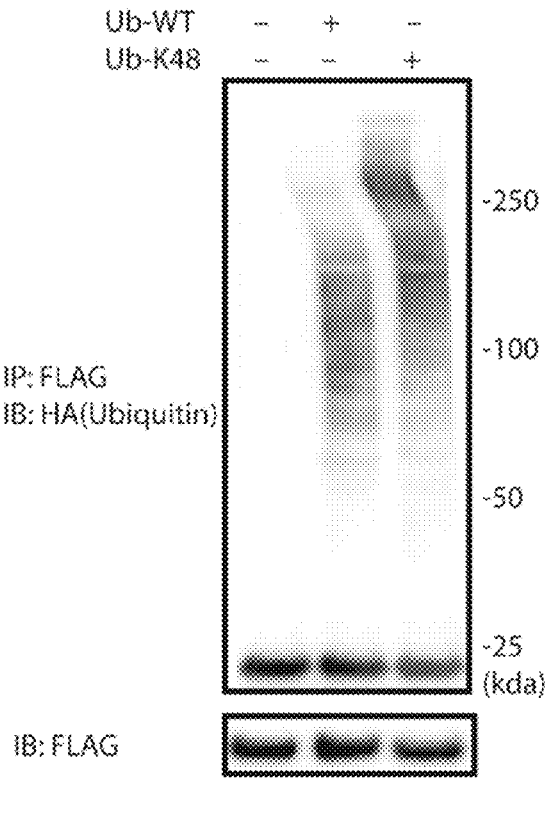
FIG. 3. Atoh1 forms K48 linked polyubiquitin chain. 293T cells were co-transfected with FLAG-Atoh1 and either wild-type HA-ubiquitin (WT) or ubiquitin with all lysines except K48 mutated, or empty vector. FLAG-Atoh1 was immunoprecipitated and blotted with antibodies against HA (ubiquitin) and FLAG (Atoh1). FLAG antibody was used to confirm the immunoprecipitation of Atoh1.

The present disclosure is based, at least in part, on the surprising discovery that inhibition of protein degradation increases levels of Atoh1 protein, which is expected to increase generation of hair cells from inner ear progenitor cells. As shown herein reducing proteasome activity led to an increase in levels of Atoh1 protein. As increased Atoh1 leads to an increase in generation of hair cells, these methods are expected to increase generation of hair cells from progenitors.

It is widely accepted that although cells capable of generating hair cells are present in the inner ear, natural hair cell regeneration in the inner ear is low (Li et al., Trends Mol. Med., 10, 309-315 (2004); Li et al., Nat. Med., 9, 1293-1299 (2003); Rask-Andersen et al., Hear. Res., 203, 180-191 (2005)). As a result, lost or damaged hair cells may not be adequately replaced by natural physiological processes (e.g., cell differentiation), and a loss of hair cells occurs. In many individuals, such hair cell loss can result in, e.g., sensorineural hearing loss, hearing impairment, and balance disorders. Therapeutic strategies that increase the number of hair cells in the inner ear will benefit a subject with hair cell loss, e.g., with one or more of these conditions.

In some embodiments, the present disclosure provides compositions and methods for preventing and/or treating auditory disease in a subject by increasing the number of sensory hair cells of the inner ear (e.g., hair cells), e.g., in the inner ear of the subject, by administering to the subject (e.g., to the inner ear of the subject) compositions that decrease protein degradation, e.g., Atoh1 degradation, in target cells.

Atoh1 is important for specifying hair cell fate and its expression is tightly regulated (Kelly et al., Nat. Rev. Neurosci., 7:837-849 (2006)). Once activated, Atoh1 interacts with its 3' enhancer in a positive feedback loop to maintain expression (Helms et al., Development, 127: 1185-1196 (2000)). Despite the reported importance of Atoh1 for hair cell differentiation (Bermingham et al., Science, 284:

1837-1841 (1999); Zheng and Gao, Nat. Neurosci., 3:580-586 (2000); Izumikawa et al., Nat. Med., 11:271-276 (2005); Kelly et al., Nat. Rev. Neurosci., 7:837-849 (2006); Gubbels et al., Nature, 455:537-541 (2008); Jeon et al., J. Neurosci., 31:8351-8358 (2011)), pathways and factors involved in its regulation are reportedly poorly understood (Fritzsch et al., Dev. Dyn., 233:570-583 (2005)).

As described herein, targeted modulation of protein degradation can be used to regulate Atoh1 and promote hair cell differentiation.

Post-Translational Regulation—the Ubiquitin-Proteasome Pathway

Post-translational modification is the chemical modification of a protein after its translation, which can include phosphorylation, acetylation, sumoylation, and ubiquitylation.

The ubiquitin-proteasome pathway plays an important role in biological processes integral to the development and physiology of eukaryotic cells. Specific proteins are labeled by polyubiquitin chains in an energy-consuming process and then targeted to the proteasome where they are degraded to small peptides. The system is highly selective and precisely regulated; it not only degrades misfolded or damaged proteins but also is essential for regulation of cell-signaling pathways, determining the half-lives ranging from minutes to days.

Ubiquitin, a 76 amino acid protein with a molecular weight of 8.5 kD, is involved in several biological processes. Isopeptide linkages to its 7 lysine residues generate a diverse set of monubiquitin or polyubiquitin chains. While K48-linked polyubiquitin chains signal for proteasomal degradation, monoubiquitylation is a signal for endocytosis or nuclear trafficking. K63-linked polyubiquitin chains signal endocytosis, ribosome modification and DNA repair (Pickart, Molecular cell. Sep. 1 2001; 8(3):499-504).

The ubiquitin system consists of three critical enzymes: ubiquitin-activating enzyme (E1), ubiquitin-conjugating enzyme (E2), and ubiquitin ligase (E3). E3 catalyzes the formation of polyubiquitin chains (and occasional monoubiquitin chains) by transferring ubiquitins that have been activated by E1 and E2 to internal lysine residues on specific substrates.

E3 ligases are classified by the occurrence of HECT (homologous to the E6-AP COOH terminus) or RING prised of Cul1, 2, 3, 4A, 4B, 5 and 7 (Jin et al., Genes Dev. 2004; 18(21):2573-2580). Cullin serves as a scaffold for assembly of the multiple subunits and transfer of ubiquitin from E2 to the substrate protein. The C-terminus of cullin binds the ring-finger protein (RING box, Rbx1) to form the core E3 ubiquitin ligase, while the N-terminus binds the adaptor module protein to mediate the interaction between cullin and its specific substrate. Cul4A E3 ubiquitin ligases contain the cullin 4A scaffold and the DDB1 (damaged DNA binding protein 1) adaptor protein. Substrate specificity is conferred by a set of substrate receptors, DDB1-and-CUL4A-associated factors (DCAF).

Although various pathways have been shown to upregulate Atoh1 expression at the transcriptional level (Jeon et al., The Journal of neuroscience: the official journal of the Society for Neuroscience. 2011; 31(23):8351-8358; Shi et al., Journal of biological chemistry. 2010; 285(1):392-400; Examples 1-10, below), post-transcriptional regulation of Atoh1 is largely unexplored. The present inventors hypothesized that inhibition of post-translational degradation could increase the level of Atoh1 protein and force progenitors toward a hair cell fate. There was a seemingly contradictory role of Sox2 in regulation of Atoh1, as Sox2 increased expression of Atoh1 mRNA but did not increase the level of Atoh1 protein. Example 11 herein shows a role of the ubiquitin proteasome pathway in the post-translational regulation of Atoh1.

Long-Lived Atoh1 Proteins

In one aspect, the invention provides long-lived Atoh1 variant polypeptides comprising one or more mutations at amino acids 328, 331, and/or 334, i.e., mutations at amino acids 328, 331, and/or 334 to any amino acid other than serine, e.g., alanine, asparagine, glutamine, threonine, tyrosine, or cysteine, preferably alanine or glycine, wherein the variant is resistant to proteasome degradation and thus has a longer half life. Also provided are isolated nucleic acid molecules that encode a long-lived Atoh1 variant polypeptide as described herein.

The sequence of human Atoh1, also known as ATH1; HATH1; MATH-1; and bHLHa14, is available in GenBank at Acc. No. NM_005172.1 (mRNA) and NP_005163.1 (protein). SEQ ID NO:1 shows the long-lived Atoh1 variant human protein sequence with the mutation sites at amino acids 328, 331 and/or 334 shown as "X."

```
                                                              (SEQ ID NO:1)
  1 msrllhaeew aevkelgdhh rqpqphhlpq pppppqppat lqarehpvyp pelslldstd
 61 prawlaptlq gictaraaqy llhspelgas eaaaprdevd grgelvrrss ggassskspg
121 pvkvreqlck lkggvvvdel gcsrqrapss kqvngvqkqr rlaanarerr rmhglnhafd
181 qlrnvipsfn ndkklskyet lqmaqiyina lsellqtpsg geqpppppas cksdhhhlrt
241 aasyeggagn ataagaqqas ggsqrptppg scrtrfsapa saggysvqld alhfstfeds
301 altammaqkn lspslpgsil qpvqeenXkt XprXhrsdge fsphshysds deas
```

(Really Interesting New Gene) domains. The human genome encodes over 600 E3 ligases, most belonging to the RING family (Deshaies and Joazeiro, Annual review of biochemistry. 2009:78:399-434). HECT domain ligases form a transient and covalent linkage with ubiquitin via a conserved cysteine, while RING domain ligases transfer ubiquitin from E2 to the substrate, without direct ubiquitylation.

RING domain E3 ligases can be further classified into single subunit, dimeric RING finger (RF), and modular classes. Modular RING E3 ligases function as part of a multi-protein complex and substrate proteins are recruited by separate subunits. Examples of modular E3 ligases include the cullin-RING ligase (CRL) superfamily, com- In one embodiment, the protein includes an amino acid sequence at least about 80%, 85%, 90%, 95%, 98% or more identical to SEQ ID NO:1, wherein one or more of amino acids 328, 331 and/or 334 are not serine. For use in the methods described herein, the protein must retain the ability to promote differentiation of a supporting cell into an auditory hair cell.

In some embodiments, an isolated nucleic acid molecule of the invention includes a nucleotide sequence encoding a variant Atoh1 human protein shown in SEQ ID NO:1, wherein one or more of amino acids 328, 331 and/or 334 are not serine, i.e., are alanine, glycine, or another amino acid. In some embodiments, the nucleic acid molecule includes sequences encoding the variant Atoh1 human protein (i.e., "the coding region" or "open reading frame"), as well as 5' untranslated sequences. Alternatively, the nucleic acid molecule can include only a coding region and, e.g., no flanking sequences that normally accompany the subject sequence. The protein includes one of the following mutations: S328A, S331A, S334A, S328A/S331A, S328A/S331A, S331A/ S334A, or S328A/S331A/S334A. An exemplary nucleic acid sequence is shown in SEQ ID NO:2, with the codons encoding amino acids 328, 331 and 334 shown as NNN.

sequence, then the molecules are identical at that position. The percent identity between the two sequences is a function of the number of identical positions shared by the sequences, taking into account the number of gaps, and the length of each gap, which need to be introduced for optimal alignment of the two sequences. In another embodiment, the percent identity of two amino acid sequences can be assessed as a function of the conservation of amino acid residues within the same family of amino acids (e.g., positive charge,

```
   1 ATGTCCCGCC TGCTGCATGC AGAAGAGTGG GCTGAAGTGA AGGAGTTGGG AGACCACCAT

61 CGCCAGCCCC AGCCGCATCA TCTCCCGCAA CCGCCGCCGC CGCCGCAGCC ACCTGCAACT

121 TTGCAGGCGA GAGAGCATCC CGTCTACCCG CCTGAGCTGT CCCTCCTGGA CAGCACCGAC

181 CCACGCGCCT GGCTGGCTCC CACTTTGCAG GGCATCTGCA CGGCACGCGC CGCCCAGTAT

241 TTGCTACATT CCCCGGAGCT GGGTGCCTCA GAGGCCGCTG CGCCCCGGGA CGAGGTGGAC

301 GGCCGGGGGG AGCTGGTAAG GAGGAGCAGC GGCGGTGCCA GCAGCAGCAA GAGCCCCGGG

361 CCGGTGAAAG TGCGGGAACA GCTGTGCAAG CTGAAAGGCG GGGTGGTGGT AGACGAGCTG

421 GGCTGCAGCC GCCAACGGGC CCCTTCCAGC AAACAGGTGA ATGGGGTGCA GAAGCAGAGA

481 CGGCTAGCAG CCAACGCCAG GGAGCGGCGC AGGATGCATG GGCTGAACCA CGCCTTCGAC

541 CAGCTGCGCA ATGTTATCCC GTCGTTCAAC AACGACAAGA AGCTGTCCAA ATATGAGACC

601 CTGCAGATGG CCCAAATCTA CATCAACGCC TTGTCCGAGC TGCTACAAAC GCCCAGCGGA

661 GGGGAACAGC CACCGCCGCC TCCAGCCTCC TGCAAAAGCG ACCACCACCA CCTTCGCACC

721 GCGGCCTCCT ATGAAGGGGG CGCGGGCAAC GCGACCGCAG CTGGGGCTCA GCAGGCTTCC

781 GGAGGGAGCC AGCGGCCGAC CCCGCCCGGG AGTTGCCGGA CTCGCTTCTC AGCCCCAGCT

841 TCTGCGGGAG GGTACTCGGT GCAGCTGGAC GCTCTGCACT TCTCGACTTT CGAGGACAGC

901 GCCCTGACAG CGATGATGGC GCAAAGAAT TTGTCTCCTT CTCTCCCCGG GAGCATCTTG

961 CAGCCAGTGC AGGAGGAAAA CNNNAAAACT NNNCCTCGGN NNCACAGAAG CGACGGGGAA

1021 TTTTCCCCCC ATTCCCATTA CAGTGACTCG GATGAGGCAA GTTAG
```

In some embodiments, an isolated nucleic acid molecule encoding a variant Atoh1 human protein described herein includes a nucleotide sequence that is at least about 85% or more identical to the entire length of a nucleotide sequence shown in SEQ ID NO:2. In some embodiments, the nucleotide sequence is at least about 90%, 91%, 92%, 93%, 94%, 95%, 96%, 97%, 98%, 99% or 100% identical to SEQ ID NO:2. The encoded protein includes at least one of the following mutations: S328A, S331A, S334A, S328A/ S331A, S328A/S331A, S331A/S334A, or S328A/S331A/ S334A.

Calculations of homology between sequences are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90% or 100%. The amino acid residues or nucleotides at corresponding amino acid positions or nucleotide positions are then compared. When a position in the first sequence is occupied by the same amino acid residue or nucleotide as the corresponding position in the second negative charge, polar and uncharged, hydrophobic) at corresponding positions in both amino acid sequences (e.g., the presence of an alanine residue in place of a valine residue at a specific position in both sequences shows a high level of conservation, but the presence of an arginine residue in place of an aspartate residue at a specific position in both sequences shows a low level of conservation).

For purposes of the present invention, the comparison of sequences and determination of percent identity between two sequences can be accomplished using blastn with Match/Mismatch scores of 1 and -2, respectively, and a linear gap penalty. See Zhang et al., J Comput Biol 2000; 7(1-2):203-14.

Recombinant Expression Vectors, Host Cells and Genetically Engineered Cells

In another aspect, the invention includes vectors, preferably expression vectors, containing a nucleic acid encoding a long-lived Atoh1 variant polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses. Additional information regarding vectors is provided below.

A vector can include a long-lived Atoh1 variant-encoding nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce long-lived Atoh1 variants as described herein.

The recombinant expression vectors of the invention can be designed for expression of long-lived Atoh1 variant proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, CA. Alternatively, the recombinant expression vector can be transcribed and translated in vitro, e.g., using T7 promoter regulatory sequences and T7 polymerase.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). For example, promoters that are primarily or only active in auditory or supporting cells can be used, e.g., a Lgr5, GFAP, Sox2, p27Kip, FGFR3, Prox1, or Sox2 promoter.

Another aspect the invention provides a host cell which includes a nucleic acid molecule described herein, e.g., a long-lived Atoh1 variant-encoding nucleic acid molecule within a recombinant expression vector or a long-lived Atoh1 variant-encoding nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a long-lived Atoh1 variant protein can be expressed in bacterial cells such as *E. coli*, insect cells, yeast or mammalian cells (e.g., Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a long-lived Atoh1 variant protein. Accordingly, the invention further provides methods for producing a long-lived Atoh1 variant protein using the host cells of the invention. In one embodiment, the method includes culturing the host cell of the invention (into which a recombinant expression vector encoding a long-lived Atoh1 variant protein has been introduced) in a suitable medium such that a long-lived Atoh1 variant protein is produced. In another embodiment, the method further includes isolating a long-lived Atoh1 variant protein from the medium or the host cell.

In another aspect, the invention features, a cell or purified preparation of cells which include a long-lived Atoh1 variant transgene, and that optionally express the long-lived Atoh1 variant. The cell preparation can consist of human or non-human cells, e.g., rodent cells, e.g., mouse or rat cells, rabbit cells, or pig cells. In some embodiments, the long-lived Atoh1 variant transgene is under control of an inducible promoter as is known in the art. Such cells can serve as a model for studying disorders that are related to Atoh1 expression.

In another aspect, the invention features a cell transformed with nucleic acid which encodes a long-lived Atoh1 variant polypeptide. The cell can be, e.g., a mammalian cell, e.g., a mesenchymal stem cell, human embryonic stem cell, inner ear-derived stem cell (see, e.g., Li et al., Nat Med. 9(10):1293-9 (2003)), hair cell progenitor, or induced pluripotent stem cell, or a cell derived therefrom, e.g., an endodermal/mesodermal progenitor that expresses Brachyury and GATA6, or an inner ear progenitor cell that expresses Sox2, which could be made from an ES cell or induced pluripotent stem cell derived from a blood cell or fibroblast, e.g., as described in Li et al., Proc Natl Acad Sci USA. 100(23):13495-500 (2003); or Oshima et al., Cell. 141(4): 704-716 (2010); see also Breuskin et al., Hear Res. 236(1-2):1-10 (2008); Bodson et al., Acta Otolaryngol. 130(3):312-7 (2010); and Jahan et al., Hear Res. 297:30-41 (2013). Alternatively, the cell can be a more differentiated cell, e.g., a fibroblast or other non-auditory cell type.

Cells, e.g., progenitor cells, expressing a long-lived human Atoh1 variant polypeptide as described herein can be introduced into an individual subject to increase the number of hair cells and treat sensorineural hearing loss or vestibular dysfunction associated with loss of auditory hair cells in the subject. Preferably, the cells are injected into the cochlea as described herein. Once implanted in an individual, the cells produce a long-lived human Atoh1 variant polypeptide described herein and differentiate into hair cells. In some embodiments, the Atoh1 is under the control of an inducible promoter, and the cells are implanted into the subject in a progenitor state, and induced to express the long-lived Atoh1 once in situ. A number of inducible promoters are known in the art, e.g., metallothionein, heat shock protein, tetracycline or minocycline promoters. See, e.g., U.S. Pat. No. 8,673,634 and Devarajan et al., J. Funct. Biomater. 2:249-270 (2011) for a review of gene delivery and stem cell based therapies for regenerating inner ear hair cells.

Transgenic animals expressing the long-lived human Atoh1 variant polypeptides described herein are also within the present invention. As used herein, a "transgenic animal" is a non-human animal, preferably a mammal, more preferably a rodent such as a rat or mouse, in which one or more of the cells of the animal includes a long-lived human Atoh1 variant transgene. Other examples of transgenic animals include non-human primates, sheep, dogs, cows, goats, chickens, amphibians, and the like. A long-lived human Atoh1 variant transgene is exogenous DNA encoding a long-lived human Atoh1 variant described herein that preferably is integrated into or occurs in the genome of the cells of a transgenic animal. A long-lived human Atoh1 variant transgene can direct the expression of the encoded gene product in one or more cell types or tissues of the transgenic animal, e.g., in cells of the inner ear of the animal. Thus, a transgenic animal can be one in which an endogenous Atoh1 gene has been altered by, e.g., by homologous recombination between the endogenous gene and an exogenous long-lived human Atoh1 variant-encoding DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence, e.g. as described above, can be operably linked to a transgene of the invention to direct expression of a long-lived human Atoh1 variant protein to particular cells. A transgenic founder animal can be identified based upon the presence of a long-lived human Atoh1 variant-encoding transgene in its genome and/or expression of long-lived human Atoh1 variant mRNA in tissues or cells of the animals. A transgenic founder animal can then be used to breed additional animals carrying the transgene. Moreover, transgenic animals carrying a transgene encoding a long-lived human Atoh1 variant protein can further be bred to other transgenic animals carrying other transgenes.

Methods of Treatment

The compounds and methods described herein are appropriate for the treatment of mammalian (e.g., human) subjects who have or are at risk of developing hearing disorders resulting from cochlear hair cell loss, preferably post-neonatal (e.g., child, adolescent or adult, e.g., above the age of 1, 2, 3, 4, 5, 6, 7, 8, 9, 10, 11, 12 or 13 years) subjects. The methods described herein can be used to treat cochlear hair cell loss and any disorder that arises as a consequence of hair cell loss in the ear, such as hearing impairments or deafness. These subjects can receive treatment with an agent described herein. The approach may be optimal for treatment of acute hearing loss shortly after the damage has occurred, and may be less effective after longer time periods when Notch signaling has returned to its baseline level in the adult.

In some instances, methods include selecting a subject. Subjects suitable for treatment include those at risk of hair cell loss or with hair cell loss and/or those at risk of sensorineural hearing loss or with sensorineural hearing loss. Any subject experiencing or at risk for developing hearing loss is a candidate for the treatment methods described herein. A human subject having or at risk for developing a hearing loss can hear less well than the average human being, or less well than a human before experiencing the hearing loss. For example, hearing can be diminished by at least 5, 10, 30, 50% or more.

The subject can have hearing loss associated with cochlear hair cell loss for any reason, or as a result of any type of event. For example, a subject can be deaf or hard-of-hearing as a result of an infection or physical ototoxic insult, e.g., a traumatic event, such as a physical trauma to a structure of the ear that does not irreversibly damage the supporting cells. In preferred embodiments, the subject can have (or be at risk of developing) hearing loss as result of exposure to a sudden loud noise, or a prolonged exposure to loud noises. For example, prolonged or repeated exposures to concert venues, airport runways, and construction areas can cause inner ear damage and subsequent hearing loss; subjects who are subjected to high levels of environmental noise, e.g., in the home or workplace, can be treated using the methods described herein. A subject can have a hearing disorder that results from aging, e.g., presbycusis, which is generally associated with normal aging processes; see, e.g., Huang, Minn Med. 90(10):48-50 (2007) and Frisina, Annals of the New York Academy of Sciences, 1170: 708-717 (2009), and can occur in subjects as young as 18, but is generally more marked in older subjects, e.g., subjects over age 40, 45, 50, 55, 60, 65, 70, 75, 80, 85, or 90. A subject can have tinnitus (characterized by ringing in the ears) due to loss of hair cells. A subject can experience a chemical ototoxic insult, wherein ototoxins include therapeutic drugs including antineoplastic agents, salicylates, quinines, and aminoglycoside antibiotics, e.g., as described further below, contaminants in foods or medicinals, and environmental or industrial pollutants. In general, subjects who have a known genetic disease associated with hearing loss (e.g., mutations in connexin 26, Alport, and so on), or a known cause of hearing loss that is associated with structural damage to the inner ear (e.g. penetrating trauma), that would not be correctable or ameliorated by the present methods are excluded from the present methods.

In some embodiments, the methods include administering to the subject a compound described herein within one, two, three, four, five, six, or seven days, or one, two, three, four, five, or six weeks of exposure to an ototoxic insult, e.g., a physical (noise, trauma) or chemical (ototoxin) insult that results in or could result in a loss of hair cells, and causes an increase in Notch signaling in the subject.

In some embodiments, a subject suitable for the treatment using the compounds and methods featured in the invention can include a subject having a vestibular dysfunction, including bilateral and unilateral vestibular dysfunction; the methods include administering a therapeutically effective amount of an agent described herein, e.g., by systemic administration or administration via the endolymphatic sac (ES). Vestibular dysfunction is an inner ear dysfunction characterized by symptoms that include dizziness, imbalance, vertigo, nausea, and fuzzy vision and may be accompanied by hearing problems, fatigue and changes in cognitive functioning. Vestibular dysfunctions that can be treated by the methods described herein can be the result of a genetic or congenital defect; an infection, such as a viral or bacterial infection; or an injury, such as a traumatic or nontraumatic injury, that results in a loss of vestibular hair cells. In some embodiments, balance disorders or Meniere's disease (idiopathic endolymphatic hydrops) may be treated by the methods described herein. Vestibular dysfunction is most commonly tested by measuring individual symptoms of the disorder (e.g., vertigo, nausea, and fuzzy vision).

Alternatively or in addition, the compounds and methods featured in the invention can be used prophylactically, such as to prevent, reduce or delay progression of hearing loss, deafness, or other auditory disorders associated with loss of hair cells. For example, a composition containing one or more compounds can be administered with (e.g., before, after or concurrently with) an ototoxic therapy, i.e., a therapeutic that has a risk of hair cell toxicity and thus a risk of causing a hearing disorder. Ototoxic drugs include the antibiotics neomycin, kanamycin, amikacin, viomycin, gentamycin, tobramycin, erythromycin, vancomycin, and streptomycin; chemotherapeutics such as cisplatin; nonsteroidal anti-inflammatory drugs (NSAIDs) such as choline magnesium trisalicylate, diclofenac, diflunisal, fenoprofen, flurbiprofen, ibuprofen, indomethacin, ketoprofen, meclofenamate, nabumetone, naproxen, oxaprozin, phenylbutazone, piroxicam, salsalate, sulindac, and tolmetin; diuretics; salicylates such as aspirin; and certain malaria treatments such as quinine and chloroquine. For example, a subject undergoing chemotherapy can be treated using the compounds and methods described herein. The chemotherapeutic agent cisplatin, for example, is known to cause hearing loss. Therefore, a composition containing one or more compounds can be administered with cisplatin therapy (e.g., before, after or concurrently with) to prevent or lessen the severity of the cisplatin side effect. Such a composition can be administered before, after and/or simultaneously with the second therapeutic agent. The two agents may be administered by different routes of administration.

In general, the compounds and methods described herein can be used to generate hair cell growth in the ear and/or to increase the number of hair cells in the ear (e.g., in the inner, middle, and/or outer ear). For example, the number of hair cells in the ear can be increased about 2-, 3-, 4-, 6-, 8-, or 10-fold, or more, as compared to the number of hair cells before treatment. This new hair cell growth can effectively restore or establish at least a partial improvement in the subject's ability to hear. For example, administration of an agent can improve hearing loss by about 5, 10, 15, 20, 40, 60, 80, 100% or more.

In some instances, compositions can be administered to a subject, e.g., a subject identified as being in need of treatment, using a systemic route of administration. Systemic routes of administration can include, but are not limited to, parenteral routes of administration, e.g., intravenous injection, intramuscular injection, and intraperitoneal injection; enteral routes of administration e.g., administration by the oral route, lozenges, compressed tablets, pills, tablets, capsules, drops (e.g., ear drops), syrups, suspensions and emulsions; transdermal routes of administration; and inhalation (e.g., nasal sprays).

In some instances, compositions can be administered to a subject, e.g., a subject identified as being in need of treatment, using a systemic or local route of administration. Such local routes of administration include administering one or more compounds into the ear of a subject and/or the inner ear of a subject, for example, by injection and/or using a pump.

In some instances, compositions can be can be injected into the ear (e.g., auricular administration), such as into the luminae of the cochlea (e.g., the Scala media, Sc vestibulae, and Sc tympani). For example, compositions can be administered by intratympanic injection (e.g., into the middle ear), intralabyrinthine delivery (e.g., to the stapes foot plate), and/or injections into the outer, middle, and/or inner ear. Such methods are routinely used in the art, for example, for the administration of steroids and antibiotics into human ears. Injection can be, for example, through the round window of the ear or through the cochlea capsule. In another exemplary mode of administration, compositions can be administered in situ, via a catheter or pump. A catheter or pump can, for example, direct a pharmaceutical composition into the cochlea luminae or the round window of the ear. Exemplary drug delivery apparatus and methods suitable for administering one or more compounds into an ear, e.g., a human ear, are described by McKenna et al., (U.S. Publication No. 2006/0030837) and Jacobsen et al., (U.S. Pat. No. 7,206,639). In some embodiments, a catheter or pump can be positioned, e.g., in the ear (e.g., the outer, middle, and/or inner ear) of a subject during a surgical procedure. In some embodiments, a catheter or pump can be positioned, e.g., in the ear (e.g., the outer, middle, and/or inner ear) of a subject without the need for a surgical procedure.

In some instances, compositions can be administered in combination with a mechanical device such as a cochlea implant or a hearing aid, which is worn in the outer ear. An exemplary cochlea implant that is suitable for use with the present invention is described by Edge et al., (U.S. Publication No. 2007/0093878).

In some instances, compositions can be administered according to any of the Food and Drug Administration approved methods, for example, as described in CDER Data Standards Manual, version number 004 (which is available at fda.give/cder/dsm/DRG/drg00301.htm).

In some instances, the present disclosure includes treating a subject by administering to the subject cells produced using the compositions and methods disclosed herein. In general, such methods can be used to promote complete or partial differentiation of a cell to or towards a mature cell type of the inner ear (e.g., a hair cell) in vitro. Cells resulting from such methods can then be transplanted or implanted into a subject in need of such treatment. Cell culture methods required to practice these methods, including methods for identifying and selecting suitable cell types, methods for promoting complete or partial differentiation of selected cells, methods for identifying complete or partially differentiated cell types, and methods for implanting complete or partially differentiated cells are described herein. Target cells suitable for use in these methods are described above.

In some instances, methods can include administering one or more compositions disclosed herein and cells produced using the compositions and methods disclosed herein to a subject.

Administration of cells to a subject, whether alone or in combination with compounds or compositions disclosed herein, can include administration of undifferentiated, partially differentiated, and fully differentiated cells, including mixtures of undifferentiated, partially differentiated, and fully differentiated cells. As disclosed herein, less than fully differentiated cells can continue to differentiate into fully differentiated cells following administration to the subject.

Where appropriate, following treatment, the subject can be tested for an improvement in hearing or in other symptoms related to inner ear disorders. Methods for measuring hearing are well-known and include pure tone audiometry, air conduction, and bone conduction tests. These exams measure the limits of loudness (intensity) and pitch (frequency) that a subject can hear. Hearing tests in humans include behavioral observation audiometry (for infants to seven months), visual reinforcement orientation audiometry (for children 7 months to 3 years); play audiometry for children older than 3 years; and standard audiometric tests for older children and adults, e.g., whispered speech, pure tone audiometry; tuning fork tests; brain stem auditory evoked response (BAER) testing or auditory brain stem evoked potential (ABEP) testing. Oto-acoustic emission testing can be used to test the functioning of the cochlear hair cells, and electro-cochleography provides information about the functioning of the cochlea and the first part of the nerve pathway to the brain. In some embodiments, treatment can be continued with or without modification or can be stopped.

Modulation of Post-Translational Degradation of Atoh1 Protein

The present disclosure provides that the levels of Atoh1 can be modulated to promote hair cell differentiation. Accordingly, the present disclosure provides compositions and methods for modulating Atoh1 protein levels in a target cell to promote differentiation of the target cell towards or to a hair cell. Modification of Atoh1 protein levels can be achieved, e.g., by increasing the half-life of Atoh1 protein.

Thus, the methods described herein include the administration of compounds that decrease degradation of Atoh1. Such compounds include proteasome inhibitors.

Based on chemical structure and active moiety, proteasome inhibitors can be classified into a number of groups: boronates (e.g., Bortezomib, MLN9708 (Ixazomib citrate), MLN2238, and CEP-18770 (Piva et al., Blood. 2008 Mar. 1; 111(5):2765-75), Delanzomib), epoxyketones (Carfilzomib, ONX 0912 (Oprozomib), and epoxomicin), aldehydes (e.g., MG-132, PSI (Figueiredo-Pereira et al., J. Neurochem. 63, 1578-1581 (1994)), and fellutamide), alpha-ketoaldehydes, beta-lactones (e.g., lactacystin, omuralide, PS-519, belactosin A, and Marizomib (NPI-0052)), vinyl sulfones (e.g., NIP-L$_3$VS and MV151), syrbactins (SylA and GlbA), and bacterial (e.g., HT1171 and GL5i. A number of other proteasome inhibitors are known in the art, including disulfiram, PR-924 (Kuhn et al., Blood. 2009; 113:4667-4676) and ISPI-101 (Hurchla et al., Leukemia. 2013; 27:430-440). See, e.g., Crawford et al., J Cell Commun Signal. 2011; 5(2): 101-110; Gupta et al., "Novel Proteasome Inhibitors for Multiple Myeloma," Contemporary oncology, summer 2013, available online at onclive.com/publications/contemporary-oncology/2013/Summer-2013/Novel-Proteasome-Inhibitors-for-Multiple-Myeloma; Moreau et al., Blood August 2012, 120 (5) 947-959; Kisselev et al., Chemistry & Biology 19:99-115 (2012); and Metcalf et al., Proteasome inhibitor patents (2010-present), informa healthcare doi: 10.1517/13543776.2014.877444.

Gene Therapy Using Nucleic Acids Encoding Long-Lived Atoh1 Proteins

Nucleic acids encoding a long-lived Atoh1 variant polypeptide as described herein comprising mutations at amino acids 328, 331, and/or 334, i.e., mutations at amino acids 328, 331, and/or 334 to any amino acid other than serine, e.g., alanine, asparagine, glutamine, threonine, tyrosine, or cysteine, preferably alanine or glycine, can be incorporated into a gene construct to be used as a part of a gene therapy protocol to treat subjects suffering from sensorineural hearing loss or vestibular dysfunction as a result of loss of auditory hair cells.

The present invention includes vectors, e.g., targeted expression vectors, for in vivo transfection and expression of a polynucleotide that encodes a long-lived Atoh1 variant as described herein, preferably in particular cell types, especially supporting cells. For example, promoters that are primarily or only active in auditory or supporting cells can be used, e.g., a Lgr5, GFAP, Sox2, p27Kip, FGFR3, Prox1, or Sox2 promoter. Expression constructs of such components can be administered in any effective carrier, e.g., any formulation or composition capable of effectively delivering the component gene to cells in vivo. Approaches include insertion of the gene in viral vectors, including recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered naked or with the help of, for example, cationic liposomes (lipofectamine) or derivatized (e.g., antibody conjugated), polylysine conjugates, gramacidin S, artificial viral envelopes or other such intracellular carriers, as well as direct injection of the gene construct or CaPO$_4$ precipitation carried out in vivo.

A preferred approach for in vivo introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, Blood 76:271 (1990)). A replication defective retrovirus can be packaged into virions, which can be used to infect a target cell through the use of a helper virus by standard techniques. Protocols for producing recombinant retroviruses and for infecting cells in vitro or in vivo with such viruses can be found in Ausubel, et al., eds., Current Protocols in Molecular Biology, Greene Publishing Associates, (1989), Sections 9.10-9.14, and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ΨCrip, ΨCre, Ψ2 and ΨAm. Retroviruses have been used to introduce a variety of genes into many different cell types, including epithelial cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573).

Another viral gene delivery system useful in the present methods utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al., BioTechniques 6:616 (1988); Rosenfeld et al., Science 252:431-434 (1991); and Rosenfeld et al., Cell 68:143-155 (1992); and Crystal, Human Gene Therapy 25:3-11 (2014). Suitable adenoviral vectors derived from the adenovirus strain Ad type 5 (e.g., dl324) or other strains of adenovirus (e.g., Ad2, Ad3, or Ad7 etc.), with E1 (and optionally one or both of E3 and E4) deleted, are known to those skilled in the art. Recombinant adenoviruses can be advantageous in certain circumstances, in that they are not capable of infecting non-dividing cells and can be used to infect a wide variety of cell types, including epithelial cells (Rosenfeld et al., (1992) supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham, J. Virol. 57:267 (1986). In some embodiments, the viral vector is an AAV5, e.g., an E1, E3, E4-deleted Adenovirus serotype 5 (Ad5) vector, or Ad28 adenovector. Exemplary viral vectors comprising wild type Atoh1 are described in Parker et al., Human Gene Therapy Methods 25(1): 1-13 (2014); Atkinson et al. PLoS ONE 9(7): e102077 (2014); Izumikawa et al. Nature Medicine, 11(3): 271-276 (2005); Schlecker et al. Gene Therapy, 2011, 18: 884-890, and in US20040237127 and US20140005257; the entire contents of 20040237127 and US20140005257 are specifically incorporated herein. See also Devarajan et al., J. Funct. Biomater. 2:249-270 (2011) for a review of gene delivery and stem cell based therapies for regenerating inner ear hair cells.

Yet another viral vector system useful for delivery of nucleic acids is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro. and Immunol. 158:97-129 (1992). It is also one of the few viruses that may integrate its DNA into non-dividing cells, and exhibits a high frequency of stable integration (see for example Flotte et al., Am. J. Respir. Cell. Mol. Biol. 7:349-356 (1992); Samulski et al., J. Virol. 63:3822-3828 (1989); and McLaughlin et al., J. Virol. 62:1963-1973 (1989). Vectors containing as little as 300 base pairs of AAV can be packaged and can integrate. Space for exogenous DNA is limited to about 4.5 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993).

In addition to viral transfer methods, such as those illustrated above, non-viral methods can also be employed to cause expression of a nucleic acid compound described herein (e.g., a long-lived Atoh1 variant as described herein) in the tissue of a subject. Typically non-viral methods of gene transfer rely on the normal mechanisms used by mammalian cells for the uptake and intracellular transport of macromolecules. In some embodiments, non-viral gene delivery systems can rely on endocytic pathways for the uptake of the subject gene by the targeted cell. Exemplary gene delivery systems of this type include liposomal derived systems, poly-lysine conjugates, and artificial viral envelopes. Other embodiments include plasmid injection systems such as are described in Meuli et al., J. Invest. Dermatol. 116(1):131-135 (2001); Cohen et al., Gene Ther. 7(22): 1896-905 (2000); or Tam et al., Gene Ther. 7(21):1867-74 (2000).

In some embodiments, a gene encoding a compound described herein, e.g., a long-lived Atoh1 variant as described herein, is entrapped in liposomes bearing positive charges on their surface (e.g., lipofectins), which can be tagged with antibodies against cell surface antigens of the target tissue (Mizuno et al., No Shinkei Geka 20:547-551 (1992); PCT publication WO91/06309; Japanese patent application 1047381; and European patent publication EP-A-43075).

In clinical settings, the gene delivery systems for the therapeutic gene can be introduced into a subject by any of a number of methods, each of which is familiar in the art. For instance, a pharmaceutical preparation of the gene delivery system can be introduced systemically, e.g., by intravenous injection, and specific transduction of the protein in the target cells will occur predominantly from specificity of transfection, provided by the gene delivery vehicle, cell-type or tissue-type expression due to the transcriptional regulatory sequences controlling expression of the receptor gene, or a combination thereof.

In some embodiments, initial delivery of the recombinant gene is more limited, with introduction into the subject being quite localized, i.e., into the inner ear or cochlea of the subject. For example, the gene delivery vehicle can be introduced by injection through the round window membrane, e.g., by intra-tympanic injection of a liquid or gel formulation or by direct delivery into the inner ear fluids, e.g., using a microfluidic device. Injection can be, for example, through the round window of the ear or through the cochlea capsule, into the liquid of the inner ear, or into the scala media. Alternatively, in some embodiments, the compound can be administered onto the round window membrane, which can be reached from the middle ear: the injection can be through the ear drum into the middle ear to allow passage of the formulation through the round window membrane. In another exemplary mode of administration, compositions can be administered in situ, via a catheter or pump, e.g., an infusion pump. A catheter or pump can, for example, direct a pharmaceutical composition into the cochlea luminae or the round window of the ear. Exemplary drug delivery apparatus and methods suitable for administering one or more compounds into an ear, e.g., a human ear, are described by McKenna et al., (U.S. Publication No. 2006/0030837) and Jacobsen et al., (U.S. Pat. No. 7,206, 639). In some embodiments, a catheter or pump can be positioned, e.g., in the ear (e.g., the outer, middle, and/or inner ear) of a subject during a surgical procedure. In some embodiments, a catheter or pump can be positioned, e.g., in the ear (e.g., the outer, middle, and/or inner ear) of a subject without the need for a surgical procedure. In some embodiments, the compositions are delivered via a pump, e.g., a mini-osmotic pump, see, e.g., Takemura et al., Hear Res. 2004 October; 196(1-2):58-68, or a catheter, see, e.g., Charabi et al., Acta Otolaryngol Suppl. 2000; 543:108-10.

In some instances, compositions can be administered in combination with a mechanical device such as a cochlea implant or a hearing aid, which is worn in the outer ear. An exemplary cochlea implant that is suitable for use with the present invention is described by Edge et al., (U.S. Publication No. 2007/0093878).

In some instances, compositions can be administered according to any of the Food and Drug Administration approved methods, for example, as described in CDER Data Standards Manual, version number 004 (which is available at fda.give/cder/dsm/DRG/drg00301.htm).

The pharmaceutical preparation of the gene therapy construct can consist essentially of the gene delivery system in an acceptable diluent, or can comprise a slow release matrix in which the gene delivery vehicle is embedded. Alternatively, where the complete gene delivery system can be produced intact from recombinant cells, e.g., retroviral vectors, the pharmaceutical preparation can comprise one or more cells, which produce the gene delivery system.

Targeting Huwe1 Using Inhibitory Nucleic Acids

As shown herein, reducing Huwe1 expression extends the half-life of Atoh1. Thus, the methods described herein can include reducing Huwe1 expression using inhibitory nucleic acids that target the Huwe1 gene or mRNA; the sequence of the human Huwe1 mRNA is in GenBank at Acc. No. NM_031407.6; the genomic sequence is at NP_113584.3. Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, modified bases/locked nucleic acids (LNAs), antagomirs, peptide nucleic acids (PNAs), and other oligomeric compounds or oligonucleotide mimetics which hybridize to at least a portion of the target Huwe1 nucleic acid and modulate its function. In some embodiments, the inhibitory nucleic acids include antisense oligonucleotides, e.g., antisense RNA, antisense DNA, chimeric antisense oligonucleotides, or antisense oligonucleotides comprising modified linkages or nucleotide; interfering RNA (RNAi), e.g., small interfering RNA (siRNA), or a short hairpin RNA (shRNA); or combinations thereof. The inhibitory nucleic acids can be modified, e.g., to include a modified nucleotide (e.g., locked nucleic acid) or backbone (e.g., backbones that do not include a phosphorus atom therein), or can by mixmers or gapmers; see, e.g., WO2013/006619, which is incorporated herein by reference for its teachings related to modifications of oligonucleotides. siRNAs directed against Huwe1 are commercially available, e.g., from Origene and Santa Cruz Biotechnology, Inc.

Pharmaceutical Formulations

The methods described herein include the manufacture and use of pharmaceutical compositions that include proteasome inhibitors, inhibitory nucleic acids targeting Huwe1, or long-lived Atoh1 proteins or nucleic acids as active ingredients. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions, e.g., dexamethasone; prednisone; gentamicin; brain-derived neurotrophic factor (BDNF); recombinant human insulin-like growth factor 1 (rhIGF-1), FGF, R-spondin. Alternatively or in addition, the one or more supplementary active compounds can include histone deacetylase (HDAC) inhibitors and/or DNMT inhibitors and/or Ezh2 Histone Methyl Transferase (HMT) inhibitors, e.g., as described in U.S. Provisional Patent Application No. 61/985,170, filed on Apr. 28, 2014, which is incorporated herein by reference in its entirety.

The present pharmaceutical compositions are formulated to be compatible with the intended route of administration. In some embodiments, the compositions are delivered systemically, e.g., by parenteral, e.g., intravenous, intradermal, or subcutaneous administration.

In some embodiments, the compositions are administered by application to the round window membrane, e.g., application of a liquid or gel formulation to the round window membrane. Application to the round window membrane can be accomplished using methods known in the art, e.g., intra-tympanic injection of a liquid or gel formulation or by direct delivery into the inner ear fluids, e.g., using a microfluidic device.

In some embodiments, the compositions are delivered via a pump, e.g., a mini-osmotic pump, see, e.g., Takemura et al., Hear Res. 2004 October; 196(1-2):58-68, or a catheter, see, e.g., Charabi et al., Acta Otolaryngol Suppl. 2000; 543:108-10.

Methods of formulating suitable pharmaceutical compositions are known in the art, see, e.g., *Remington: The Science and Practice of Pharmacy,* 21st ed., 2005; and the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freezedrying, which yield a powder of the active ingredient plus any additional desired ingredient from a previously sterile-filtered solution thereof.

In some embodiments, the therapeutic compounds are prepared with carriers that will protect the therapeutic com-pounds against rapid elimination from the body, such as a controlled release formulation, including implants and microencapsulated delivery systems. Liposomal suspen-sions (including liposomes targeted to selected cells with monoclonal antibodies to cellular antigens) can also be used as pharmaceutically acceptable carriers. These can be pre-pared according to methods known to those skilled in the art, for example, as described in U.S. Pat. No. 4,522,811. Nanoparticles, e.g., poly lactic/glycolic acid (PLGA) nan-oparticles (see Tamura et al., Laryngoscope. 2005 Novem-ber; 115(11):2000-5; Ge et al., Otolaryngol Head Neck Surg. 2007 October; 137(4):619-23; Horie et al., Laryngoscope. 2010 February; 120(2):377-83; Sakamoto et al., Acta Oto-laryngol Suppl. 2010 November; (563):101-4) can also be used.

In some embodiments, the carrier comprises a polymer, e.g., a hydrogel, that increases retention of the compound on the round window and provides local and sustained release of the active ingredient. Such polymers and hydrogels are known in the art, see, e.g., Paulson et al., Laryngoscope. 2008 April; 118(4):706-11 (describing a chitosan-glycero-phosphate (CGP)-hydrogel based drug delivery system); other carriers can include thermo-reversible triblock copo-lymer poloxamer 407 (see, e.g., Wang et al., Audiol Neu-rootol. 2009; 14(6):393-401. Epub 2009 Nov. 16, and Wang et al., Laryngoscope. 2011 February; 121(2):385-91); polox-amer-based hydrogels such as the one used in OTO-104 (see, e.g., GB2459910; Wang et al., Audiol Neurotol 2009; 14:393-401; and Piu et al., Otol Neurotol. 2011 January; 32(1):171-9); Pluronic F-127 (see, e.g., Escobar-Chavez et al., J Pharm Pharm Sci. 2006; 9(3):339-5); Pluronic F68, F88, or F108; polyoxyethylene-polyoxypropylene triblock copolymer (e.g., a polymer composed of polyoxypropylene and polyoxyethylene, of general formula E106 P70 E106; see GB2459910, US20110319377 and US20100273864); MPEG-PCL diblock copolymers (Hyun et al., Biomacro-molecules. 2007 April; 8(4):1093-100. Epub 2007 Feb. 28); hyaluronic acid hydrogels (Borden et al., Audiol Neurootol. 2011; 16(1):1-11); gelfoam cubes (see, e.g., Havenith et al., Hearing Research, February 2011; 272(1-2):168-177); and gelatin hydrogels (see, e.g., Inaoka et al., Acta Otolaryngol. 2009 April; 129(4):453-7); other biodegradable, biocompat-ible polymers can be used, such as ethylene vinyl acetate, polyanhydrides, polyglycolic acid, collagen, polyorthoe-sters, and polylactic acid. Tunable self-assembling hydro-gels made from natural amino acids L and D can also be used, e.g., as described in Hauser et al e.g. Ac-LD6-COOH (L) e.g. Biotechnol Adv. 2012 May-June; 30(3):593-603. Such formulations can be prepared using standard tech-niques, or obtained commercially, e.g., from Alza Corpora-tion and Nova Pharmaceuticals, Inc.

The pharmaceutical compositions can be included in a container, pack, or dispenser together with instructions for administration.

Dosage

An "effective amount" is an amount sufficient to effect beneficial or desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the thera-peutic compounds selected. The compositions can be admin-istered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treat-ment of a subject with a therapeutically effective amount of the therapeutic compounds described herein can include a single treatment or a series of treatments. In some embodi-ments, e.g., in subjects exposed to prolonged or repeated exposures to noise, e.g., normal noises such as are associated with activities of daily life (such as lawnmowers, trucks, motorcycles, airplanes, music (e.g., from personal listening devices), sporting events, etc.), or loud noises, e.g., at concert venues, airports, and construction areas, that can cause inner ear damage and subsequent hearing loss; e.g., subjects who are subjected to high levels of environmental noise, e.g., in the home or workplace, can be treated with repeated, e.g., periodic, doses of the pharmaceutical com-positions, e.g., to prevent (reduce the risk of) or delay progression or hearing loss.

Dosage, toxicity and therapeutic efficacy of the therapeu-tic compounds can be determined by standard pharmaceu-tical procedures, e.g., in cell cultures or experimental ani-mals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While com-pounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. For example, samples of the perilymph or endolymph can be obtained to evaluate pharmacokinetics and approximate an effective dosage, e.g., in animal models, e.g., after administration to the round window. The dosage of such compounds lies preferably within a range of con-centrations that include the ED50 with little or no toxicity. The dosage may vary within this range depending upon the dosage form employed and the route of administration utilized. For any compound used in the method of the invention, the therapeutically effective dose can be esti-mated from cell culture assays, and/or a dose may be formulated in animal models; alternatively, for those com-pounds that have been previously used in humans, clinically desirable concentrations can be used as a starting point. Such information can be used to more accurately determine useful doses in humans. An exemplary dose for gene therapy using an adenoviral vector is between about $10^{10}$ and $5\times10^{10}$, delivered in a volume between 10-100 μl, preferably between 20 and 40 μl.

Kits

The compositions and/or cells disclosed herein can be provided in a kit. For example, kits can include one or more active compounds as described herein, such as in a compo-sition that includes the compound(s), and optionally infor-mational material. The informational material can be descriptive, instructional, marketing or other material that relates to the methods described herein and/or to the use of the agent for the methods described herein. For example, the informational material relates to the use of the compound to treat a subject who has, or who is at risk for developing, an auditory hair cell loss hearing. The kits can also include paraphernalia for administering one or more compounds to a cell (in culture or in vivo) and/or for administering to a patient, and any combination of the methods described herein.

In one embodiment, the informational material can include instructions for administering the pharmaceutical composition and/or cell(s) in a suitable manner to treat a human, e.g., in a suitable dose, dosage form, or mode of administration (e.g., a dose, dosage form, or mode of administration described herein). In another embodiment, the informational material can include instructions to administer the pharmaceutical composition to a suitable subject, e.g., a human, e.g., a human having, or at risk for developing, auditory hair cell loss.

The informational material of the kits is not limited in its form. In many cases, the informational material (e.g., instructions) is provided in printed matter, such as in a printed text, drawing, and/or photograph, such as a label or printed sheet. However, the informational material can also be provided in other formats, such as Braille, computer readable material, video recording, or audio recording. Of course, the informational material can also be provided in any combination of formats.

In addition to the compound(s), the composition of the kit can include other ingredients, such as a solvent or buffer, a stabilizer, a preservative, a fragrance or other cosmetic ingredient, and/or a second agent for treating a condition or disorder described herein. Alternatively, the other ingredients can be included in the kit, but in different compositions or containers than the compound. In such embodiments, the kit can include instructions for admixing the agent and the other ingredients, or for using one or more compounds together with the other ingredients.

The kit can include one or more containers for the pharmaceutical composition. In some embodiments, the kit contains separate containers, dividers or compartments for the composition and informational material. For example, the composition can be contained in a bottle (e.g., a dropper bottle, such as for administering drops into the ear), vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the pharmaceutical composition. For example, the kit can include a plurality of syringes, ampoules, foil packets, or blister packs, each containing a single unit dose of the pharmaceutical composition. The containers of the kits can be air tight and/or waterproof, and the containers can be labeled for a particular use. For example, a container can be labeled for use to treat a hearing disorder.

As noted above, the kits optionally include a device suitable for administration of the composition (e.g., a syringe, pipette, forceps, dropper (e.g., ear dropper), swab (e.g., a cotton swab or wooden swab), or any such delivery device).

EXAMPLES

The invention is further described in the following examples, which do not limit the scope of the invention described in the claims.

Methods

The following materials and methods were used in the Examples below.

Cell Culture

HEK cells, FLAG-HA-Atoh1 293T cells and HeLa cells were grown in DMEM supplemented with 10% heat-inactivated fetal bovine serum, 2 mM Glutamax and penicillin (100 U/ml)/streptomycin (100 µg/ml) (all from Invitrogen). All cultures were maintained in a 5% CO2/20% humidified incubator (Forma Scientific).

Generation of Atoh1 Plasmids and Stably Expressing Cell Line

To generate FLAG Atoh1 plasmids, a construct consisting of Atoh1 cDNA modified to include two consecutive FLAG-tag sequences (GATTACAAGGATGACGA) preceding the start codon, was subcloned into pcDNA3.1(+) (Parker et al., 2014).

Atoh1 mutants, including deletions (Δ10-93 for deletion 1, Δ94-105 for deletion 2, Δ214-305 for deletion 3 and Δ306-347 deletion 4) and mutations at the C-terminus (serine 309, 325, 328, 331 or 334 to alanine) were generated using the QuickChange Site-directed Mutagenesis Kit (Stratagene). All mutants were sequenced in their entirety.

Figure 15:
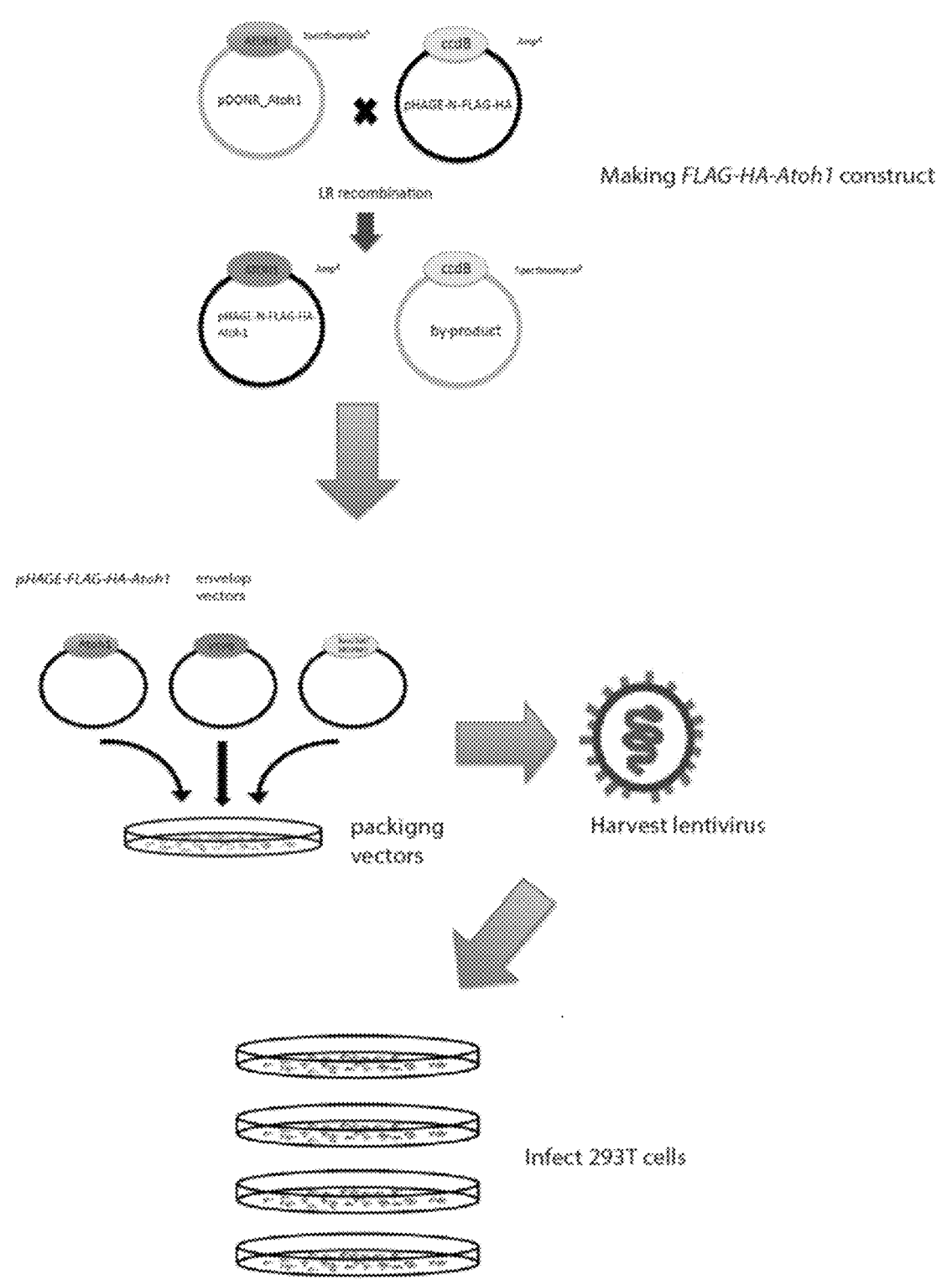
FIG. 15. Generation of a FLAG-HA-Atoh1 stably expressing cell line. A construct containing the transgene was incorporated into a lentiviral vector. After recombination of the FLAG-HA-Atoh1 construct to place the transgene under the promoter, FLAG-HA-Atoh1 along with the packaging plasmids were transfected into 293T cells. Lentivirus particles expressing FLAG-HA-Atoh1 were harvested and infected into 293T cells again. Cells expressing the transgene were selected by growth in medium containing puromycin.

To generate FLAG-HA-Atoh1 plasmids, sequence-verified Atoh1 clones in pDONR223 were recombined into the Gateway destination vector pHAGE-N-Flag-HA (Invitrogen) using λ recombinase (Sowa et al., 2009). To generate lentivirus for the 293T cell line stably expressing Atoh1, 1 µg of pHAGE-N-FLAG-HA-Atoh1 cDNA was co-transfected with 4 helper plasmids (2 µg of VSVG, 1 µg each of Tat1b, Mgpm2, and CMV-Rev) using Lipofectamine 2000 (Invitrogen) in 10 cm dishes of 293T cells. Virus particles were harvested 48 hours post-transfection and used to infect 293T cells. Puromycin (Sigma, 1 µg/ml) was used for the selection of infected cells (Sowa et al., 2009). See FIG. 15.

Western Blotting

Proteins extracted with RIPA buffer from whole cells were separated on 4-12% NuPAGE Bis-Tris gels (Invitrogen) and electrotransferred to 0.2 µm nitrocellulose membranes (Bio-Rad). The membranes were probed with mouse anti-FLAG (Sigma-Aldrich), mouse anti-HA (Sigma-Aldrich), mouse anti-ubiquitin (Santa Cruz), mouse anti-β-actin (Sigma-Aldrich), or mouse anti-HSC70 (1:10,000, Santa Cruz Biotechnology) antibodies, followed by HRP-conjugated, anti-rabbit or anti-mouse IgG, or anti-mouse light chain antibody (Jackson Immunoresearch Laboratories). The blots were processed with ECL or ECL-Plus Western Blot Substrates (Thermo). Band intensity was quantified by densitometry using Quantity One software (Bio-Rad). Each band was normalized to β-actin or HSC70 and expressed as a ratio to the control.

Cycloheximide Chase Assays for Stability

HEK cells were transfected with either FLAG-Atoh1 (wild-type), or indicated mutant FLAG-Atoh1 plasmids (1 µg/ml) using Lipofectamine 2000 (3 µl per 1 µg of cDNA, Invitrogen). Forty-eight hours after transfection, 100 µg/ml cycloheximide (Sigma) was added to block protein synthesis. Cells were harvested at 0, 30, 60, 120, and 240 minutes. Equal amounts of protein from each treatment were taken for Western blotting. Protein bands were quantified by densitometry. The half-lives of indicated proteins were calculated using GraphPad Prism 6 software and a one-phase exponential-decay model.

Co-Immunoprecipitation

To determine if the ubiquitin-proteasome pathway was involved in Atoh1 degradation, HEK cells were transfected with FLAG-Atoh1 (1 µg/ml) using Lipofectamine 2000

(Invitrogen) for 48 hours and either DMSO or MG132 (10 µM) for 6 hours. Transfected cells were lysed in Pierce IP Lysis Buffer (Thermo) containing 1× complete protease inhibitors and 1×PhosSTOP phosphatase inhibitors (Roche). Lysates were immunoprecipitated with Anti-FLAG M2 Affinity Gel (Sigma-Aldrich) and immunoblotted by the procedures mentioned above.

To determine K48 polyubiquitylation, HEK cells were co-transfected with FLAG Atoh1 (1 µg/ml) and wild-type, K48 ubiquitin plasmids or empty vector (0.5 µg/ml, from Addgene) using Lipofectamine 2000 (Invitrogen). At 48 hours post-transfection, cells were lysed and immunoprecipitated with anti-FLAG M2 Affinity gel and immunoblotted.

Luciferase Assay $10^5$ HEK cells were seeded into a 96-well plate 1 day before transfection. 50 ng of firefly report construct with an Atoh1 E-box associated motif (AtEAM), 5 ng of *Renilla*-luciferase construct, and 50 ng of wild-type or mutated Atoh1 plasmids were mixed 0.3 ul of Lipofectamine 2000 and incubated with the cells for 48 hours, until cells were lysed. Luciferase activity were measure by the Dual Luciferase Reporter Assay System (Promega) in a Victor3 plate reader (Perkin Elmer).

Protein Purification

HEK293T cells with stable expression of Atoh1 from 15-cm tissue culture dishes at approximately 80% confluence were lysed in a total volume of 4 ml of lysis buffer (50 mM Tris pH 7.8, 150 mM sodium chloride, 0.5% NP40 plus EDTA-free protease inhibitor cocktail (Roche) and incubated at 4° C. for 45 minutes. Lysates were centrifuged at 13,000 rpm for 10 minutes at 4° C. and filtered through 0.45 µm spin filters (Millipore) to remove cell debris. Sixty µl of immobilized anti-HA resin (Sigma; 50% slurry) were used to immunoprecipitate the cleared lysates by gentle inversion overnight. Once the binding was complete, resin containing immuno-complex was washed with lysis buffer 4 times, followed by PBS 4 times. Atoh1 was eluted with HA peptide (250 µg/ml) in PBS for 30 minutes (3×50 µl) at room temperature. Ten percent of the eluate was electrophoresed on a NuPAGE Novex 4-12% Bis-Tris gel and silver stained to confirm immunoprecipitation of Atoh1 and the remaining eluate was subjected to trichloroacetic acid (TCA) precipitation for subsequent IP-MS/MS analysis.

In other experiments, specific bands stained for Commassie blue after elution were excised for peptide mass spectrometric sequencing at the core facility of Harvard Medical School.

Mass Spectrometry

For identification of Atoh1 interacting proteins, the TCA-precipitated protein pellet was re-suspended in 25 µg/µl of sequencing grade trypsin (25 µg/µl in 30 µl 100 mM ammonium bicarbonate pH 8.0 with 10% acetonitrile) and incubated at 37° C. for 4 hours. Digested samples were loaded onto stagetips and washed. Peptides were eluted with 50% formic acid/5% acetonitrile to neutralize the trypsin, followed by drying and re-suspension in 10 µl of 5% formic acid/5% acetonitrile. The resulting spectra were analyzed against a human database by SEQUEST, a tandem mass spectrometry data analysis program for peptide sequencing and protein identification (Eng et al. Journal of the American Society for Mass Spectrometry 5:976-989 (1994). The list of proteins was loaded into CompPASS for further processing and analysis (Sowa et al., 2009).

Co-Immunoprecipitation

FLAG-HA-Atoh1 293T were lysed with IP buffer and the lysates were immunoprecipitated with HA-resin (Sigma), IgG conjugated A/G agarose, or empty A/G agarose (Santa Cruz Biotechnology) and immunoblotted with antibodies against HA and Huwe1. For reciprocal immunoprecipitation, similar lysates were immunoprecipitated with A/G agarose conjugated with rabbit anti-Huwe1 antibody (Novus Biological) and immunoblotted with antibodies against HA or Huwe1.

To explore the role of Huwe1 on ubiquitylation of Atoh1, we generated Myc-Huwe1 with cysteine 4341 mutated to alanine (Myc-Huwe1-C4341) by recombining Huwe1 pENTR plasmids (Addgene) into pDEST-CMV-N-Myc using Gateway cloning. FLAG-HA-Atoh1 293T cells were transfected with wild-type Huwe1, Huwe1 shRNA (Sigma) or empty vector for 48 hours and treated with MG132 (10 µM) or vehicle for 6 hours. Cell lysates were immunoprecipitated with anti-FLAG-resin (Sigma) and immunoblotted with mouse anti-ubiquitin antibody (Santa Cruz Biotechnology) or reblotted with mouse anti-FLAG or rabbit anti-Huwe1 antibodies.

Wild-type or mutant Myc-Huwe1, wild-type or K48 HA-ubiquitin, and FLAG-Atoh1 plasmids were co-transfected into HeLa cells. After 48 hours, cell lysates were immunoprecipitated with anti-FLAG resin and immunoblotted with mouse anti-HA, mouse anti-FLAG and rabbit anti-Huwe1 antibodies. Input was blotted with mouse anti-Myc, mouse anti-FLAG, and mouse anti-β-actin antibodies as loading controls.

Neonatal Cochlear Explant Culture

Cochlear tissues were dissected from 1-day postnatal CD-1 mice (Charles River Laboratories). Spiral ganglion, Reissner's membrane, and the hook region of the organ of Corti were removed to obtain a flat cochlear surface preparation (Parker et al., 2010). Explants were plated onto 4-well plates (Greiner Bio-One) coated with Matrigel (BD Biosciences) diluted 1:10 in DMEM supplemented with 10% fetal bovine serum overnight.

Huwe1 Knockdown in the Organ of Corti

As described previously, postnatal day 1 mouse organs of Corti were cultured on Matrigel-coated coverslips overnight. The organs were incubated with Huwe1 or scrambled siRNA (IDT-DNA, 100 nM) for 72 hours.

Detection of Proliferation by Incorporation of 5-Ethynyl-2'-Deoxyuridine (EdU)

To evaluate cell proliferation, organs of Corti were incubated with 3 µM 5-ethynyl-2'-deoxyuridine (EdU) in combination with siRNA treatment and replenished after 36 hours. The tissue was fixed, blocked and permealized as described.

RNA Preparation for Quantitative RT-PCR

Total RNA was extracted with the RNeasy Mini Kit (Qiagen) according to the manufacturer's instructions. 1 µg RNA was reverse transcribed to cDNA using the Improm-II Reverse Transcription System (Promega). The reverse transcription conditions were 25° C. for 10 min followed by 37° C. for 60 min; the reaction was terminated at 95° C. for 5 min. The cDNA products were mixed with LightCycler Taqman Master Mix (Roche) and Taqman primers (Invitrogen) in a 96-well plate according to the manufacturer's instructions. The qPCR was run in triplicate on an ABI 7700 Real-Time PCR machine (Applied Biosystems, Inc.) with the initial denaturation at 95° C. for 2 min, denaturation at 95° C. for 15 s, and annealing/extension at 60° C. for 1 min for 45 cycles. Huwe1 gene expression was calculated relative to 18S RNA, and the amount of cDNA applied was adjusted to bring the Ct value for 18S RNA to within one half-cycle.

Detection of Proliferation by Incorporation of EdU

To evaluate cell proliferation, organ of Corti tissue was incubated with EdU in combination with siRNA treatment and replenished after 36 hours. The tissue was fixed, blocked and permeabilized as described. 70 μl of Alexa-Flour 488-conjugated azide cocktail (Invitrogen) was added to each well and incubated in a light-proof chamber at room temperature for 30 minutes. Tissues were washed with PBS before adding secondary antibodies.

Imaging and Cell Counting

Organs of Corti were analyzed using a Leica TCS SP5 confocal microscope. Inner and outer hair cells and supporting cells (in the outer hair cell region) were counted in cochlear whole mounts. High-power fluorescent images of the organ of Corti were merged in Adobe Illustrator CS6; total length and cell counts were determined with ImageJ software (NIH). Organs of Corti were divided into four regions (apex, mid-apex, mid-base, and base) and hair cell and supporting cells counts were obtained per 100 μm. Each counted segment was 1200-1400 μm.

Mouse Genotyping

The Sox2-Cre-ER mouse was described previously (Arnold et al., Cell Stem Cell 9, 317-329 (2011); Bramhall et al., Stem Cell Reports 2, 311-322 (2014)). The Sox2-flox mice were obtained from the Jackson Laboratory. The Huwe1-flox mouse was also previously described (Hao et al., J Exp Med 209, 173-186 (2012)). The Sox2-Cre-ER mouse was genotyped with Cre primers: forward, 5'-TGG GCG GCA TGG TGC AAG TT-3' and reverse, 5'-CGG TGC TAA CCA GCG TTT TC-3'). The Huwe1-flox mouse was genotyped with the following primers: forward, 5' GTA TGG TCA TGA TTG AGT GCT TGG AAC T 3' and reverse, 5' TAT ACC TGA ACA CAT GGG CAT ATA CAT 3'. The Sox2-flox mice were genotyped by PCR according to Jackson Laboratory recommendations.

Cochlear Function Tests

Distortion product otoacoustic emissions (DPOAEs) and auditory brainstem responses (ABRs) were recorded as described previously52. The ABR stimuli were 5-ms tone pips with a 0.5 ms rise-fall time delivered at 30/s. Sound level was incremented in 5-dB steps, from 25 dB below threshold to 80 dB sound pressure level (SPL). DPOAEs were recorded for primary tones with a frequency ratio of 1.2 and with the level of the f2 primary 10 dB less than f1 level, incremented together in 5-dB steps. The 2f1-f2 DPOAE amplitude and surrounding noise floor were extracted. DPOAE threshold is defined as the f1 level required to produce a response amplitude of 0 dB SPL.

Statistical Analysis

The mean values and standard error of the mean were calculated and analyzed for significance by an unpaired two-tailed Student's t-test with indicated alpha (0.05, 0.01 or 0.001) with Prism 6 software.

Example 1: Atoh1 is a Short-Lived Protein

To determine the half-life of Atoh1, we used cycloheximide to prevent new protein synthesis and followed the time course of disappearance of previously synthesized Atoh1 by Western blotting during a chase period. We transfected 293T cells with FLAG-HA-Atoh1 and treated with cycloheximide at 48 hours after transfection.

Pre-existing Atoh1 was completely degraded by 2 hours after inhibition of new protein synthesis. The half-life, as measured by densitometry in three experiments was 35.31 minutes (95% confidence interval: 24.11+/−65.97 minutes; FIG. 1).

Example 2. Atoh1 is Degraded by the Ubiquitin-Proteasome Pathway

Since Atoh1 is a highly unstable protein with a turnover rate of less than 1 hour, we assessed the mechanism of degradation. When treated with MG132, a potent proteasome inhibitor, the level of Atoh1 was significantly increased (FIG. 2), suggesting that inhibition spared Atoh1 from proteasomal degradation. Proteasome inhibition extended the half-life of Atoh1 in a cycloheximide chase assay (FIG. 2), indicating that it interfered with Atoh1 degradation.

We then assessed polyubiquitylation of Atoh1 in the presence of a proteasome inhibitor which would prevent degradation of the ubiquitinated protein. We prepared HEK cells stably transfected with FLAG-HA-Atoh1 and treated with MG132 to inhibit proteasomal degradation. The cell lysates were immunoprecipitated with anti-FLAG antibody, and the pattern of ubiquitylation was assessed with an anti-ubiquitin antibody. Western blotting of immunoprecipitated FLAG-Atoh1 revealed high molecular weight forms of Atoh1, indicating polyubiquitylation (FIG. 2D). Increased density of these high molecular weight forms was seen in samples treated with proteasome inhibitor, MG132, indicating accumulation of polyubiquitylated Atoh1.

To determine if Atoh1 forms K48-linked polyubiquitin, the form of ubiquitin chain targeted for proteasomal degradation, we co-transfected HEK cells with FLAG-Atoh1 and ubiquitin plasmid with mutations in all lysines except K48, or without mutations. The formation of high molecular weight bands above the Atoh1 bands on immunoblots suggested that K48 ubiquitin chains were formed on Atoh1 in both cases (FIG. 3).

Figures 4A, 4B:
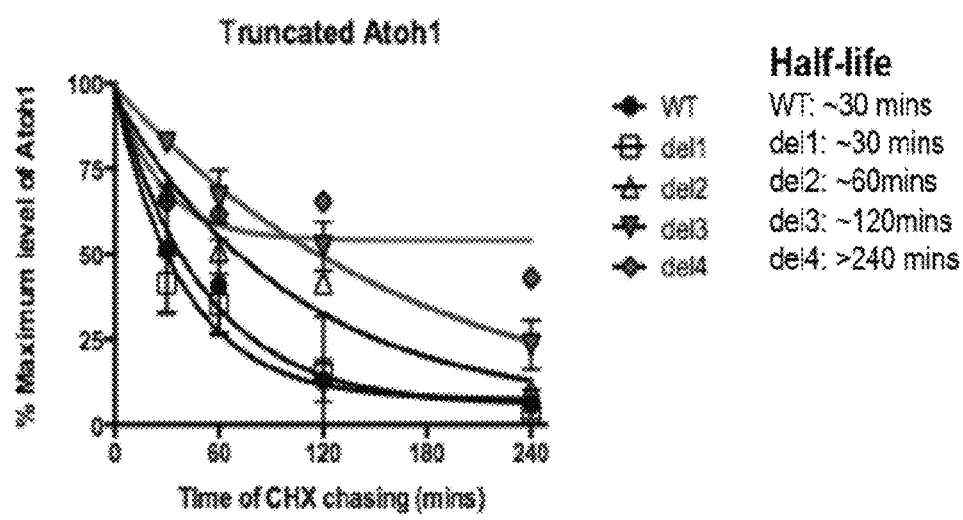
FIGS. 4A-B. Evolutionarily conserved serines in the C-terminus of Atoh1 account for its stability. (A) Half-life analysis of truncated Atoh1 over a 4-hour time frame. HEK cells were transfected with either wild-type or truncated FLAG-Atoh1 for 48 hours, and incubated with cycloheximide (100 ug/ml) for the indicated times. (3-actin served as a loading control for input protein. (B) Quantification of protein half-lives. Error bars indicate the ratio of Atoh1 to β-actin.

Example 3. Evolutionarily Conserved Serines in the C-Terminus Account for Atoh1 Stability We next generated a panel of two N-terminal (Δ10-93 for deletion 1 and Δ94-105 for deletion 2) and two C-terminal (Δ214-305 for deletion 3 and Δ306-347 deletion 4) deletions of Atoh1 plasmids (FIG. 4), retaining the bHLH domain in order to assess which regions might affect degradation. Atoh1-deletion 4 has the longest half-life in a cycloheximide chase assay, suggesting that motifs affecting the half-life of Atoh1 fall between amino acids 306 and 347 (FIG. 4B).

Figures 5A, 5B, 5C:
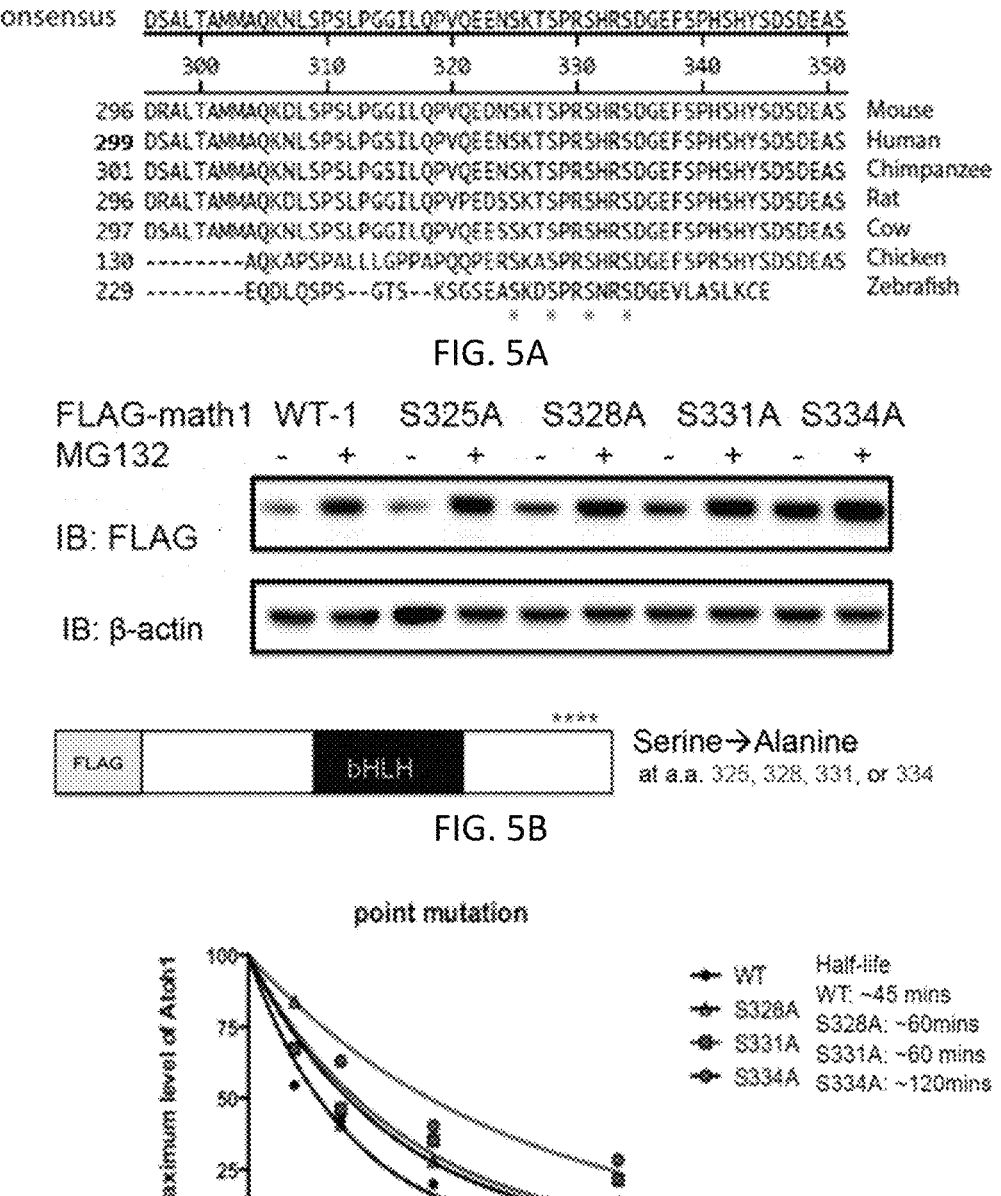
FIGS. 5A-C. 5334 is a critical residue for Atoh1 degradation. (A) C-terminus of Atoh1 (area 4) of different species were aligned. Conserved serines at 325, 328, 331 and 334 are marked with asterisks. (B) HEK cells were transfected with wild-type or mutated FLAG-Atoh1 plasmids for 40 hours and treated with either vehicle (DMSO) or MG132. After treatment with inhibitor for 6 hours, S334A had the smallest increase in Atoh1 (vehicle treatment is marked with a minus sign), while wild-type or other mutated Atoh1 proteins showed large increases in Atoh1. (C) Half-life analysis of mutated Atoh1 proteins over a 4-hour time frame. HEK cells were transfected with either wild-type or mutated FLAG-Atoh1 plasmids for 48 hours, and incubated with cycloheximide (100 ug/ml) for the indicated times. The ratio of Atoh1 to β-actin based on densitometry was plotted.

Cross-species sequence comparison by MegaAlign (DNAstar, Madison, Wis.) indicated that serines 309, 325, 328, 331 and 334 were conserved across species (FIG. 5A, right panel). Since conservation may relate to biological function, we generated mutated Atoh1 plasmids containing alanine in the place of each serine (S309A, S325A, S328A, S331A, and S334). Mutation at positions 328 and 331 modestly prolonged Atoh1 half-life, while mutation at position 334 had a dramatic effect (FIG. 5B). We conclude that Ser 334 in the C-terminus of Atoh1 contains a motif that specifies proteasomal Atoh1 for degradation.

Example 4. Generation of Atoh1 Plasmids and Stably Expressing Cell Line

To generate FLAG Atoh1 plasmids, construct consisting of the Atoh1 sequence modified by cloning to include two consecutive FLAG-tag sequences (GATTA- CAAGGATGACGA) preceding the start codon, was sub-cloned into pcDNA3.1(+) (Parker et al., Hum Gene Ther Methods 25, 1-13 (2014)).

Atoh1 mutants including deletions (410-93 for deletion 1, 494-105 for deletion 2, 4214-305 for deletion 3 and 4306-347 deletion 4) and mutations at the C-terminus (serine 309, 325, 328, 331 or 334 to alanine) were generated using the QuickChange Site-directed Mutagenesis Kit (Stratagene). All mutants were sequenced in their entirety.

To generate FLAG-HA-Atoh1 plasmids, sequence-verified Atoh1 clones in pDONR223 were recombined into the Gateway destination vector pHAGE-N-Flag-HA using λ recombinase (Sowa et al., Cell 138, 389-403 (2009)). To generate lentivirus for the 293T cell line stably expressing Atoh1, 1 ug of pHAGE-N-FLAG-HA Atoh1 cDNA was co-transfected with 4 helper plasmids (2 ug of VSVG, 1 ug of Tat1b, Mgpm2, and CMV-Rev) using Lipofectamine 2000 transfection agent (Invitrogen) in 10 cm dishes of 293T cells. Virus particles were harvested 48 hours post-transfection and used to infect 293T cells. Puromycin (Sigma, 1 ug/ml) was used for selection of infected cells (Sowa et al., Cell 138, 389-403 (2009)).

Example 5. Stability Assays—Cycloheximide Chase

HEK cells were transfected with either FLAG Atoh1 (wild type), or indicated mutant FLAG Atoh1 plasmids (1 ug/ml) using Lipofectamine 2000 (3 ul per 1 ug of cDNA, Invitrogen). Forty eight hours after transfection, 100 ug/ml cycloheximide (C4859, Sigma) was added to block protein synthesis. Cells were harvested at 0, 30, 60, 120, and 240 minutes. Equal amounts of proteins from each treatment were taken for Western blotting. Protein bands were quantified by densitometry using Quantity One Software (Bio-Rad), with β-actin for normalization. The half-lives of indicated proteins were calculated using GraphPad Prism 6 software and a one-phase exponential-decay model.

Example 6. Identifying Atoh1-Interacting Proteins by Mass Spectrometry

We performed immuoprecipitation followed by mass spectrometry (IP/MS), to identify binding partners of Atoh1 and searched the partners for E3 ubiquitin ligases that could be involved in the ubiquitin-proteasomal degradation (Sowa et al., Cell 138, 389-403 (2009)). We used a stably expressing 293T cell line prepared by lentiviral infection of pHAGE-FLAG-HA-Atoh1 Lysates of FLAG-HA-Atoh1 293T cells immunoprecipitated with HA antibody were subjected to LC-MS/MS analysis to identify proteins associated with Atoh1. We used ComPASS, an unbiased comparative approach for identifying high-confidence candidate interacting proteins, to interrogate datasets for parallel mass spectral studies (Sowa et al., Cell 138, 389-403 (2009)). The scoring metrics, DN and Z, were used to assign scores to each protein. Proteins with a DN score greater one and a Z score great than 3.5 were considered high confidence interacting partners (Table I).

E-proteins, E12 and E47 (TCF3 products), which are known interacting partners of Atoh1, were obtained in the high confidence candidates and validated the IP/MS approach. Another E-protein, TCF12, which has not been reported to bind Atoh1, was also found as Atoh1 binding partner.

Two de-ubiquitinating enzymes, USP11 and USP47, were observed associated with Atoh1. These enzymes cleave the bond between ubiquitin and substrate protein. E3 ubiquitin ligase, Huwe1, was also observed in the high confidence proteins and was the only ligase that passed the criteria for DN and Z scores among the Atoh1 interactors.

TABLE I

Identifying Atoh1-interacting proteins by mass spectrometry. Lysates of FLAG-HA-Atoh1 293T cells were immuno-precipitated with HA antibody and subjected to proteomic analysis by LC-MS/MS. ComPASS, an unbiased comparative approach for identifying high-confidence candidate interacting proteins, was utilized to interrogate data sets and assign the DN and Z scoring metrics. Proteins with a DN score greater than 1 and a Z score greater than 3.5 fulfilled these criteria.

|  | Symbol | GeneID | $D^N$_Score | Z_score |
|---|---|---|---|---|
| ATOH1 | ATOH1 | 474 | 8.37 | 5.74 |
| E3 ligase | HUWE1 | 10075 | 1.50 | 5.56 |
| Ubiquitin-related enzymes | USP11 | 8237 | 1.41 | 5.42 |
| (deubiquitylases) | USP47 | 55031 | 2.00 | 5.54 |
| E-protein | TCF3 | 6929 | 3.16 | 5.57 |
|  | TCF12 | 6938 | 2.45 | 5.71 |
| Cell Death and Survival | AHSA1 | 10598 | 1.00 | 5.03 |
|  | ATP2A1 | 487 | 1.41 | 5.71 |
|  | MAPK3 | 5595 | 2.00 | 5.71 |
|  | PRDX4 | 10549 | 1.23 | 4.60 |
|  | PRPS1 | 5631 | 1.23 | 4.60 |
|  | SRI | 6717 | 1.41 | 5.71 |
| Cell movement | ENAH | 55740 | 1.41 | 5.71 |
|  | FLNC | 2318 | 1.15 | 5.21 |
|  | GFAP | 2670 | 2.45 | 5.71 |
|  | PDE4D | 5144 | 1.41 | 5.71 |
|  | SLC3A2 | 6520 | 1.41 | 5.71 |
|  | TUBA1C | 84790 | 1.39 | 2.88 |
|  | TUBA4A | 7277 | 3.00 | 3.77 |
|  | TUBB2B | 347733 | 2.58 | 4.36 |
|  | ZYX | 7791 | 1.58 | 5.48 |
| OTHERS | AAMP | 14 | 1.00 | 5.03 |
|  | ACOX1 | 51 | 1.41 | 5.71 |
|  | BCKDHA | 593 | 2.00 | 5.54 |
|  | CCDC124 | 115098 | 1.00 | 5.03 |
|  | CPOX | 1371 | 2.00 | 5.54 |
|  | CTPS2 | 56474 | 2.45 | 5.60 |
|  | EIF2C1 | 26523 | 1.00 | 5.16 |
|  | EIF2C2 | 27161 | 3.16 | 5.72 |
|  | EIF2C3 | 192669 | 1.00 | 5.16 |
|  | FHL3 | 2275 | 1.00 | 5.16 |
|  | NEK9 | 91754 | 2.83 | 5.54 |
|  | NT5DC2 | 64943 | 2.00 | 5.71 |
|  | PDXK | 8566 | 1.41 | 5.71 |
|  | SEC23A | 10484 | 1.23 | 5.24 |
|  | SEC23B | 10483 | 1.00 | 5.03 |
|  | SERPINH1 | 871 | 1.00 | 3.92 |
|  | TNRC6C | 57690 | 2.00 | 5.71 |
|  | YARS2 | 51067 | 1.41 | 5.71 |

Example 7. Immunoprecipitation Confirms Binding of Huwe1 to Atoh1

Figures 6A, 6B, 6C:
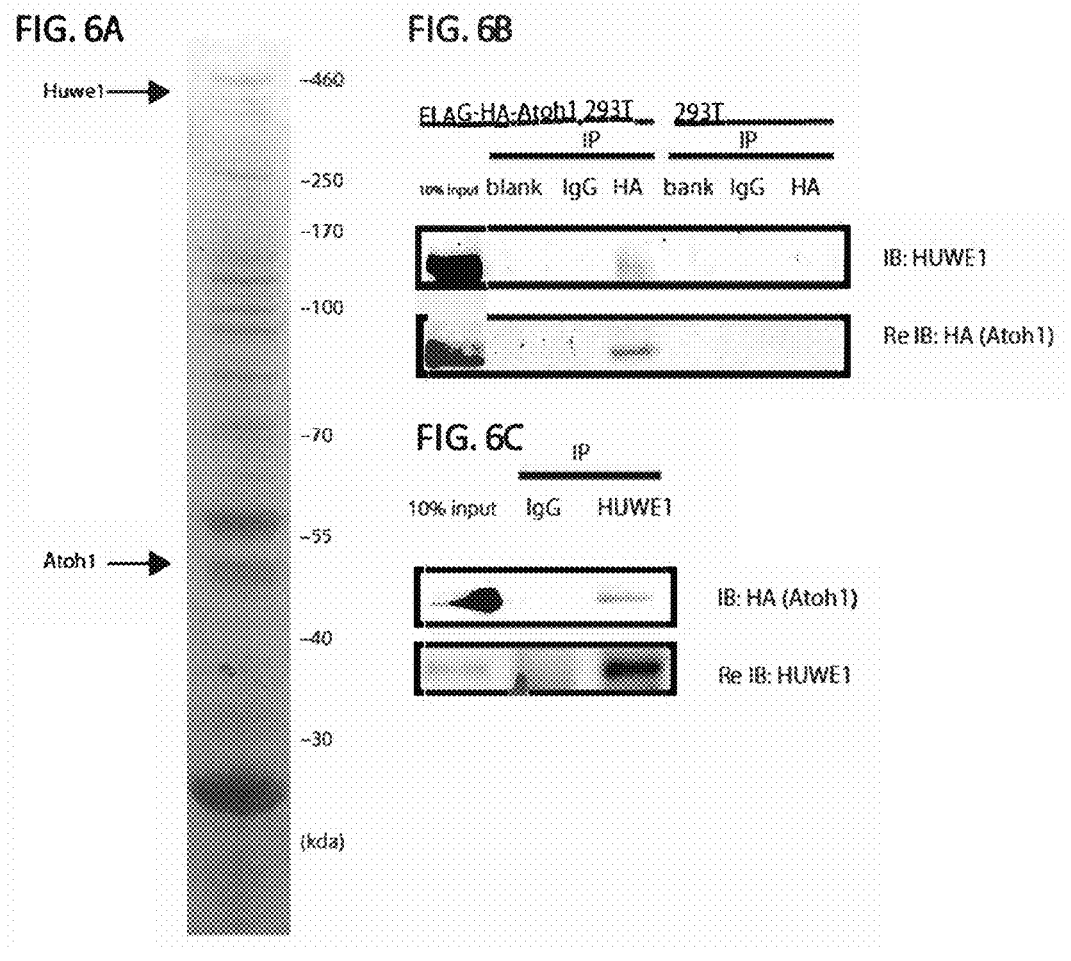
FIGS. 6A-C. Reciprocal immunoprecipitation confirmed interaction of endogenous Huwe1 with Atoh1. (A) Coomassie blue staining of Atoh1-associated proteins. FLAG-HA tagged Atoh1 was purified from whole cell extracts of a stably transfected 293T cell line. Associated proteins were detected by silver staining. The areas indicated by the arrows were cut out for mass spectrometry (Table II) and Western blotting. (B) FLAG-HA-Atoh1 293T lysates were immunoprecipitated with the indicated antibodies (IgG and HA) and subjected to immunoblotting with an antibody to Huwe1. The blot was stained with an HA antibody to measure the efficiency of immunoprecipitation. (C) Endogenous Huwe1 interacts with Atoh1. FLAG-HA-Atoh1 293T cell lysates were subjected to immunoprecipitation using IgG or Huwe1 antibody, followed by immunoblotting by HA antibodies to show the interaction with Atoh1 protein. Stripping and re-blotting with Huwe1 antibody was used to detect the efficiency of immunoprecipitation.

We first asked whether Huwe1 formed a physical complex with Atoh1 in HEK cells through reciprocal co-immunoprecipitation analyses (FIG. 6). Mass spectrometric analysis of a Coomassie blue-stained band at 450 kDa from a lysate immunoprecipitatied with an Atoh1 antibody identified Huwe1 as an interacting protein (FIG. 6 and Table II). Mass spectrometry of the band at 45 kDa confirmed that the immunoprecipitated protein was FLAG-HA-Atoh1 (Table II).

Example 8. Is Huwe1 an E3 Ubiquitin Ligase for Atoh1?

Figure 7A:
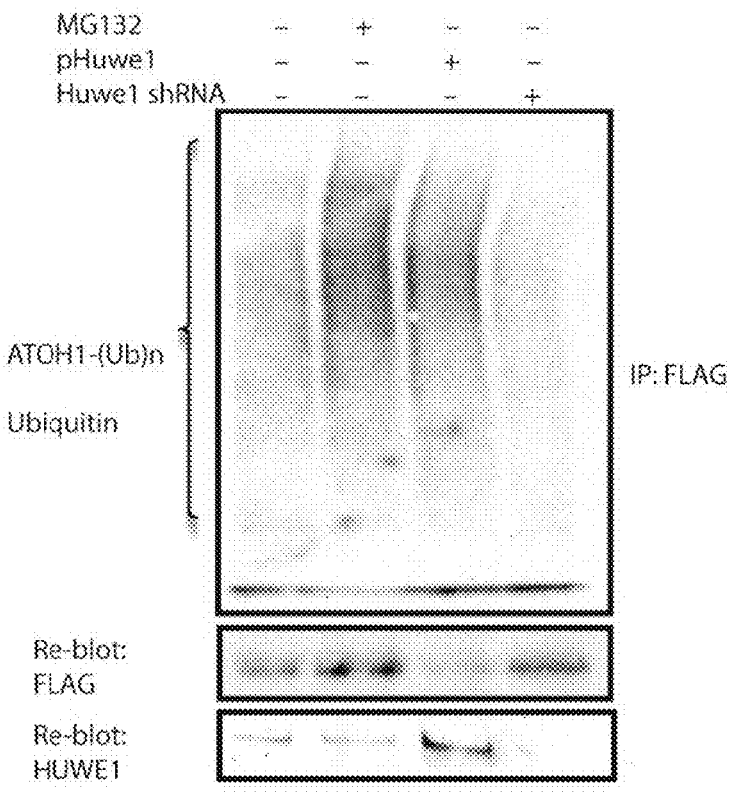
FIGS. 7A-B. Ubiquitylation of Atoh1 by Huwe1 occurs at K48. (A) FLAG-HA-Atoh1 cells were transfected with empty vector, Huwe1, or Huwe1 shRNA for 72 hours, and lysates were immunoprecipitated with antibodies against FLAG; lysates treated with MG132 for 4 hours before harvest serve as a positive control. An anti-ubiquitin antibody was used to detect ubiquitin conjugates; blots were stripped and re-blotted with FLAG and Huwe1 antibodies. The lowest panel shows total extracts immunoblotted with an anti-FLAG antibody to detect FLAG-tagged Atoh1. (B) 293T cells co-transfected with empty vector or Huwe1 and wild-type HA-ubiquitin (WT) or mutant lysine 48 (K48) plasmids for 72 hours were lysed and subjected to immunoprecipitation with an anti-FLAG antibody. Ubiquitin conjugates were detected with an anti-HA antibody. The lower panel shows blots stripped and re-blotted with an anti-FLAG antibody.
Figure 7B:
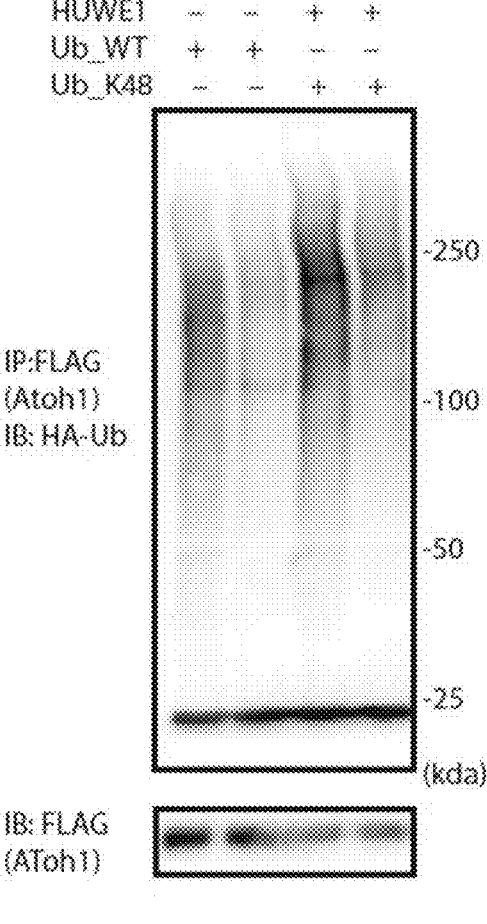

To determine whether Huwe1 can act as an E3 ubiquitin ligase for Atoh1, we performed an in vivo ubiquitylation assay. Increased ubiquitylation of Atoh1 was observed after transfecting Huwe1 plasmids into FLAG-HA-Atoh1 293T cells, after co-immunoprecipitation, indicating a role of Huwe1 as an E3 ubiquitin ligase (FIG. 7A). Furthermore, decreased poly-ubiquitylation was observed after Huwe1 knockdown, suggesting that E3 ubiquitin ligase activity on Atoh1 was inhibited.

We also tested whether the ability of Huwe1 to transfer ubiquitin to Atoh1 was affected when a mutant form of Huwe1 that had serine in the place of a critical cysteine in the HECT domain (Huwe1 C4341S) (ref) was used (FIG. 8). The resulting decrease in both wild-type and K48 poly-ubiquitylated Atoh1 indicated that this active site residue was required for the ubiquitylation of Atoh1.

TABLE II

Mass spectrometric analysis of suspected Huwe1 and Atoh1. Coomassie blue stained bands indicated in FIG. 6 were excised and subjected to mass spectrometric analysis. Table II-1 validates Huwe1 as a binding partner of Atoh1. Table II-2 identifies the immunoprecipitated protein as Atoh1.

| Gene Symbol | Total peptide | Unique peptide | Average peptide score | Protein coverage |
|---|---|---|---|---|
| Table II-1. Mass spectrometric identification of Atoh1 binding proteins | | | | |
| HUWE1 | 279 | 122 | 3.5367 | 28.78% |
| PRKDC | 161 | 112 | 3.3479 | 25.48% |
| MAP1B | 133 | 78 | 3.7349 | 37.68% |
| DYNC1H1 | 87 | 75 | 3.2275 | 18.02% |
| KIF11 | 79 | 46 | 3.3049 | 37.97% |
| SRRM2 | 53 | 38 | 3.7266 | 20.75% |
| MACF1 | 51 | 50 | 3.2235 | 8.57% |
| MYCBP2 | 51 | 47 | 3.3464 | 13.64% |
| MDN1 | 41 | 37 | 3.3880 | 8.79% |
| HERC2 | 36 | 34 | 3.2990 | 9.08% |
| RNF213 | 32 | 30 | 3.0488 | 6.38% |
| UBR5 | 31 | 26 | 3.3120 | 12.54% |
| UTRN | 30 | 30 | 3.4022 | 10.81% |
| MGA | 29 | 27 | 3.6467 | 13.52% |
| AKAP9 | 26 | 26 | 2.9820 | 8.08% |
| PRRC2C | 26 | 21 | 3.2923 | 8.08% |
| CEP350 | 23 | 21 | 3.1575 | 11.08% |
| SON | 22 | 20 | 3.6486 | 9.66% |
| PLEC | 17 | 16 | 2.8815 | 3.86% |
| MAP1A | 15 | 14 | 3.2701 | 8.46% |
| DMXL1 | 13 | 12 | 3.1873 | 5.48% |
| TRRAP | 12 | 12 | 3.1620 | 3.91% |
| SACS | 12 | 12 | 2.5812 | 2.88% |
| GOLGB1 | 12 | 10 | 2.8166 | 3.28% |
| Table II-2. Mass spectrometric identification of Atoh1 | | | | |
| TUBB2A | 159 | 40 | 3.0903 | 55.51% |
| ATOH1 | 155 | 19 | 2.1144 | 34.18% |
| TUBA1A | 112 | 34 | 3.1383 | 66.08% |
| RPL4 | 106 | 36 | 2.4767 | 53.63% |
| EEF1A1 | 103 | 28 | 2.6454 | 58.87% |
| TUFM | 72 | 38 | 3.2781 | 68.36% |
| RPL3 | 67 | 29 | 2.5399 | 45.66% |
| SSB | 65 | 30 | 2.8608 | 5.43% |
| RBMX | 65 | 27 | 2.5009 | 47.06% |
| ENO1 | 62 | 34 | 3.1674 | 58.29% |
| PSMC5 | 52 | 31 | 3.5295 | 64.29% |
| PSMC2 | 50 | 29 | 2.9925 | 63.74% |
| YARS2 | 11 | 8 | 3.3677 | 29.77% |
| TUBA1C | 7 | 11 | 3.6062 | 15.14% |
| SERPINH1 | 9 | 7 | 2.5123 | 20.81% |
| ACOX1 | 5 | 4 | 2.8799 | 10.30% |
| BCKDHA | 5 | 3 | 2.6629 | 9.44% |
| PRPS1 | 3 | 3 | 2.6642 | 18.46% |
| TUBB2B | 2 | 1 | 3.0318 | 2.70% |
| TUBA4A | 1 | 1 | 3.4258 | 31.31% |

TABLE II-continued

Mass spectrometric analysis of suspected Huwe1 and Atoh1. Coomassie blue stained bands indicated in FIG. 6 were excised and subjected to mass spectrometric analysis. Table II-1 validates Huwe1 as a binding partner of Atoh1. Table II-2 identifies the immunoprecipitated protein as Atoh1.

| Gene Symbol | Total peptide | Unique peptide | Average peptide score | Protein coverage |
|---|---|---|---|---|
| PRDX4 | 1 | 1 | 3.1432 | 7.01% |
| AAMP | 1 | 1 | 2.3377 | 2.53% |
| PDE4B | 1 | 1 | 2.2331 | 2.04% |

Example 9. Huwe1 Knockdown Extends the Half-Life of Atoh1

To determine whether Huwe1 affected the stability of Atoh1, FLAG-HA-Atoh1 293T cells were transfected with Huwe1 plasmids or Huwe1 shRNA for gain- or loss-of-function experiments respectively. Huwe1 overexpression reduced Atoh1, while Huwe1 knockdown stabilized Atoh1 (FIG. 9).

The half-life of Atoh1 measured by a cycloheximide-chase assay also revealed that Huwe1 shRNA extended the half-life of Atoh1 in FLAG-HA-Atoh1 293T cells (FIGS. 9, C & D). These results support the hypothesis that Huwe1 degrades Atoh1 through the ubiquitin-proteasome pathway.

Example 10. Inhibition of Proteasomal Activity Stabilizes Cochlear Atoh1

Figure 10:
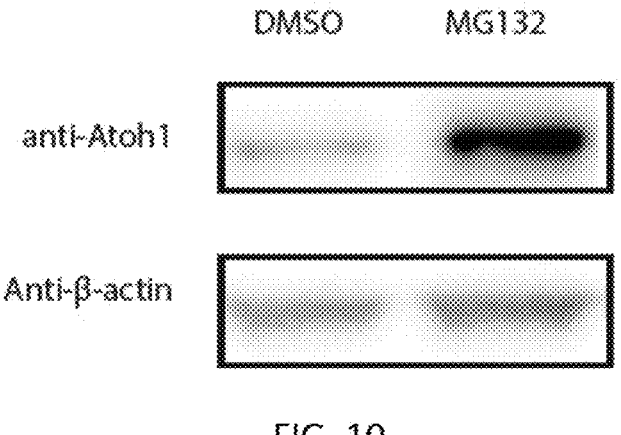
FIG. 10. Inhibition of proteasome activity stabilizes Atoh1 in the cochlea. The organ of Corti from a P1 mouse was treated with proteasome inhibitor, MG132 (10 uM) for 3 hours. Atoh1 levels were higher in the MG132-treated organ of Corti. DMSO served as control; β-actin is a loading control.

To test whether proteasomal activity regulated Atoh1 in the cochlea we treated P1 organ of Corti explants with proteasome inhibitor, MG132 (10 uM). Atoh1 was increased by the treatment indicating that it was stabilized by the treatment (FIG. 10).

Example 11. Huwe1 Knockdown Increased Atoh1 in the Organ of Corti

Figure 11:
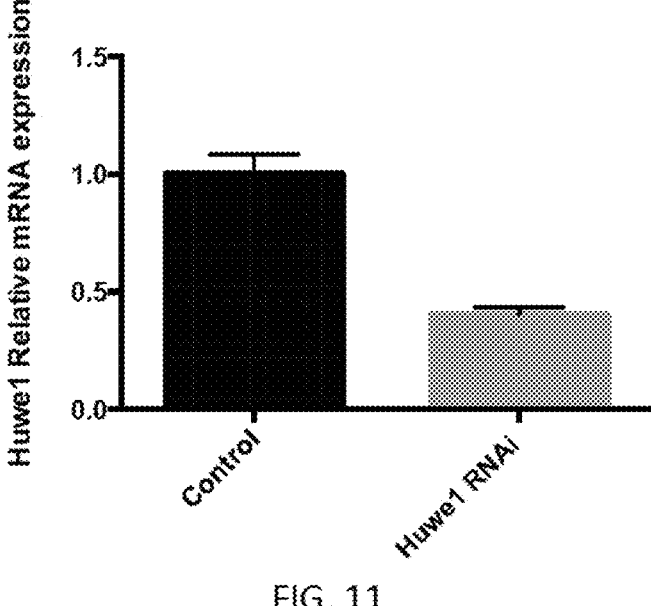
FIG. 11. qRT-PCR of RNAi-treated organ of Corti. P1 organ of Corti was treated with indicated siRNA (100 nM) for 72 hours. Huwe1 siRNA suppressed Huwe1 expression by 59.5%, compared to scrambled siRNA. Error bars indicate SEM.
Figure 12:
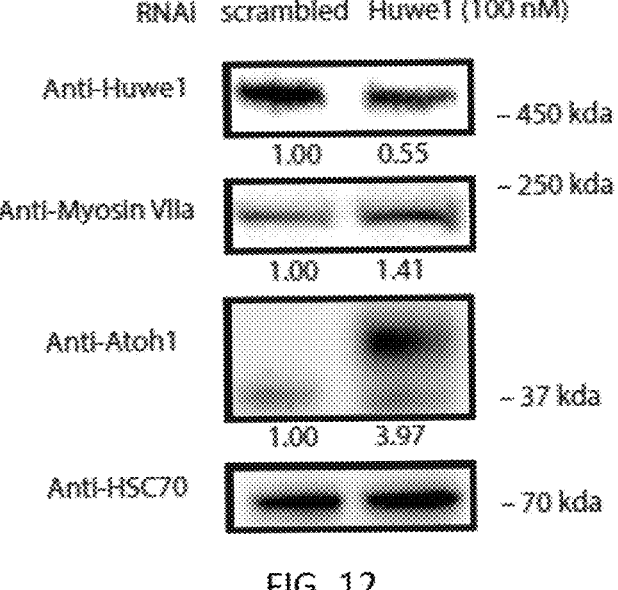
FIG. 12. Huwe1 knockdown stabilizes Atoh1. P1 organs of Corti were treated with the indicated siRNA (100 nM) for 72 hours. Huwe1, myosin VIIa and Atoh1 were quantified after Western blotting by densitometry normalized to a loading control (HSC70).

Treatment of organ of Corti explants from P1 mice with 100 nM Huwe1 siRNA for 72 hours suppressed Huwe1 gene expression by 59.5% as measured by real-time qRT-PCR (FIG. 11) and decreased protein level by 55% by Western blot (FIG. 12). RNAi-mediated depletion of Huwe1 caused a marked accumulation of Atoh1 in the cochlea based on densitometry. Hair cell marker, myosin VIIa, was also upregulated by Huwe1 siRNA, indicating a potential increase in the number of hair cells after stabilization of Atoh1 by knockdown of Huwe1.

Example 12. Huwe1 Knockdown Increased Hair Cell Generation in the Organ of Corti Since Huwe1 knockdown stabilized Atoh1, we assessed its effect on hair cell generation in the cochlea. Treatment of organ of Corti explants with 100 nM Huwe1 siRNA significantly increased the number of myosin VIIa-positive cells in the outer hair cell region (FIG. 13A) ($45.06 \pm 2.10$ vs $31.68 \pm 2.66$ after treatment with scrambled siRNA, $p<0.01$). Huwe1 siRNA significantly increased hair cell formation in the apex ($44.01 \pm 3.95$ vs $31.48 \pm 3.85$, $p<0.05$) and mid-apex ($48.80 \pm 1.78$ vs $31.43 \pm 2.33$, $p<0.001$) when the organ of Corti was quantified in four regions of equal length. Slight increases in the mid-base (44.76±2.86 vs 40.81±3.08) and base (42.72±2.90 vs 38.26±4.13) were not significant (FIGS. 13B and 13C).

Example 13. New Hair Cells are not a Result of Proliferation

Figures 14A, 14B:
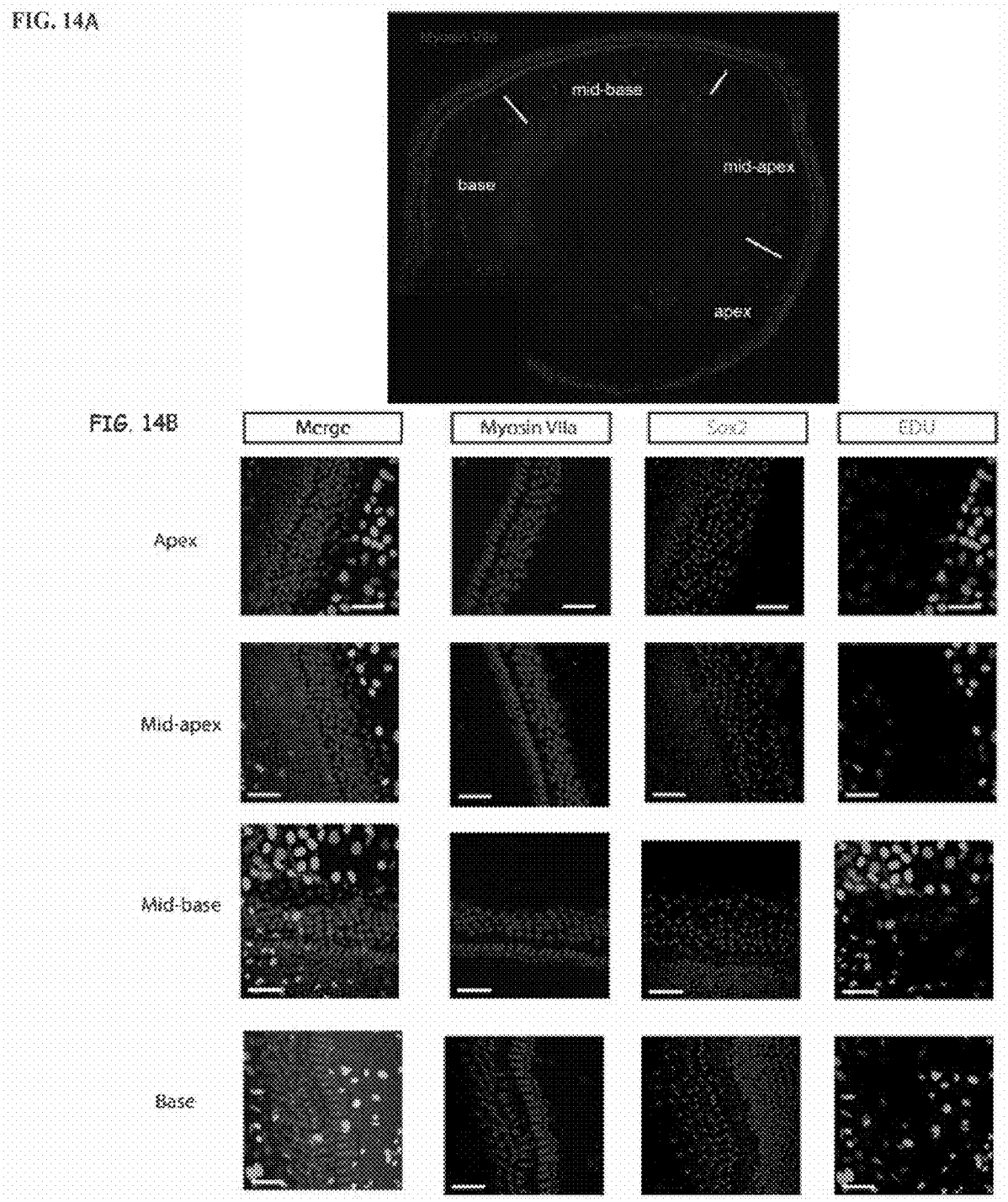
FIGS. 14A-B. Increased number of hair cells is not from proliferation. (A) Myosin VIIa-positive cells are seen throughout the organ of Corti explants. (B) Organ of Corti explants treated with Huwe1 siRNA for 72 hours showed an increase in myosin VIIa-positive cells, without any positive EdU-positive cells. Sox2 was used to stain supporting cells. The scale bar is 100 uM.

Supporting cells and hair cells were not labeled by 5-ethynyl-2'-deoxyuridine (EdU), a marker for cell division 72 hours after siRNA treatment of organ of Corti explants (FIG. 14), indicating that they were not the product of renewed cell division of either cell type. The increase in hair cells generated by siRNA-mediated suppression of Huwe1 was therefore a result of direct transdifferentiation of supporting cells.

Example 14. Huwe1 Knockdown in the Organ of Corti

As described previously, postnatal day 1 mouse organs of Corti were cultured on Matrigel-coated coverslips overnight. Huwe1 or scrambled siRNA (from IDT-DNA, 100 nM) were incubated for 72 hours.

Example 15. Detection of Proliferation by Incorporation of 5-Ethynyl-2'-Deoxyuridine (EdU)

To evaluate cell proliferation, organs of Corti were incubated with 3 uM 5-ethynyl-2'-deoxyuridine (EdU) in combination with siRNA treatment and replenished after 36 hours. The tissue was fixed, blocked and permealized as described.

Example 16. RNA Preparation for Quantitative RT-PCR

Total RNA was extracted with the RNeasy Mini Kit (Qiagen) according to the manufacturer's instructions. 1 ug RNA was reverse transcribed to cDNA using improm-II Reverse Transcription System (Promega). The reverse transcription conditions were 25° C. for 10 min followed by 37° C. for 60 min; the reaction was terminated at 95° C. for 5 min. The cDNA products were mixed with LightCycler Taqman Master Mix (Roche, 04535286001) and Taqman primers (Invitrogen) in 96-well plate according to the manufacturer's instructions. The qPCR was run in triplicate on an ABI 7700 Real-Time PCR machine (Applied Biosystem, Inc.) with initial denaturation at 95° C. for 2 min, denaturation at 95° C. for 15 s, and annealing/extension at 60° C. for 1 min for 45 cycles. Huwe1 gene expression was calculated relative to 18S RNA, and the amount of cDNA applied was adjusted to bring the Ct value for 18S RNA to within one half-cycle.

Example 17. Huwe1 is Required for Cochlear Function

Figure 16A:
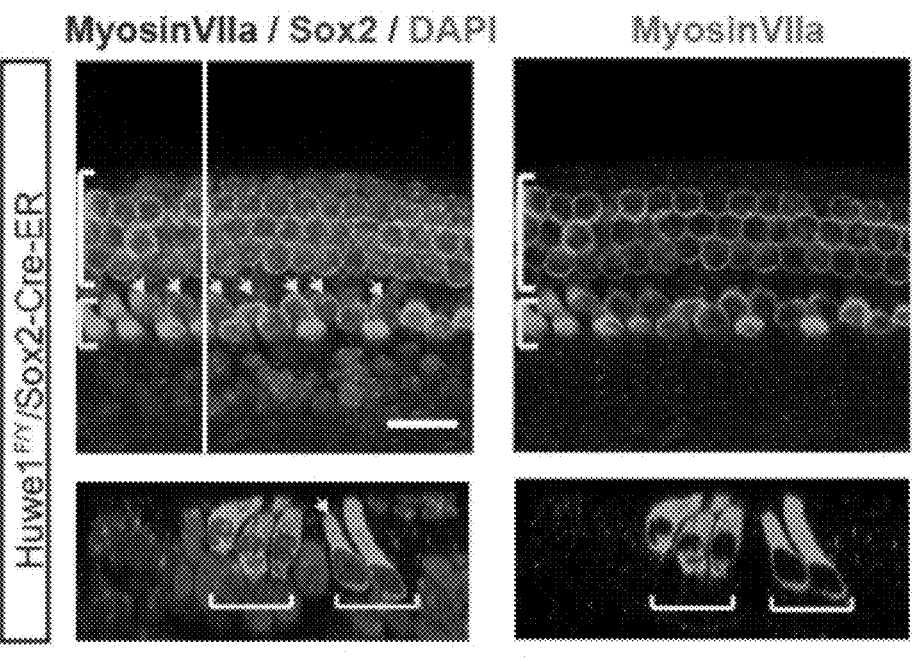
Figure 16B:
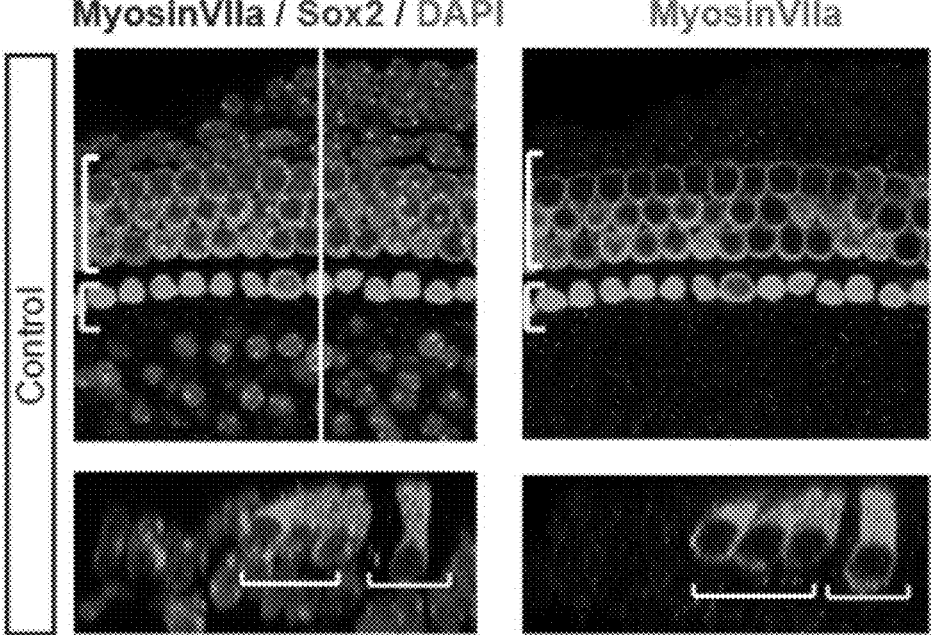
Figure 16F:
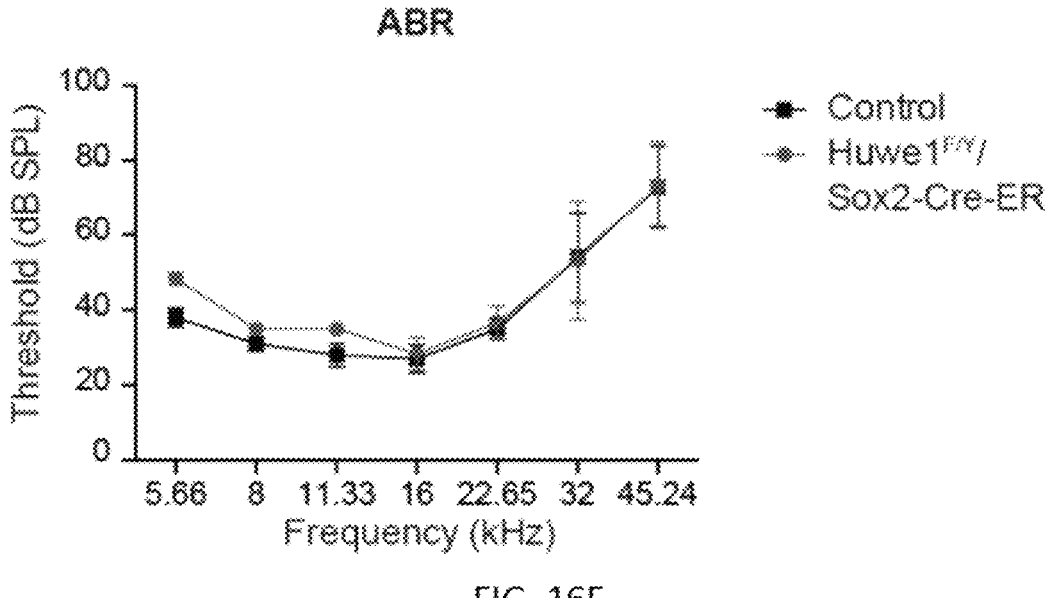

To assess the role of Huwe1 in cochlear development, we induced the conditional deletion of Huwe1 using a Cre driven by Sox2 expression, which is specific for the prosensory progenitors in the developing cochlea and is subsequently expressed in the developing spiral ganglion and cochlear supporting cells. Disruption of Huwe1 at E15.5 stimulated generation of a single extra row of inner hair cells at E18.5 (FIG. 16a compared to FIG. 16b). The extra hair cells were found in the inner pillar cell region, where extra hair cells are also produced upon stimulation of Wnt signaling in cochlear supporting cells (Shi et al., Proc Natl Acad Sci USA 110, 13851-13856 (2013)). We were unable to examine the phenotype in the mature animal after deletion of Huwe1 in Sox2-expressing cells, however, as the mice did not reach maturity. Mice with Huwe1 knocked out at P1 did survive to adulthood, allowing us to assess their phenotype. When analyzed at P30, there was an extra row of inner hair cells, similar to the E15-deleted animals. Further examination revealed that the extra hair cells were normally innervated (16.1 synapses per hair cell in the modular row, 15.3 in the pillar cell row vs 16.6 in control animals) thus effectively doubling the total number of afferent synapses in the cochlea (FIGS. 16C vs 16D). Auditory brainstem response (ABR) and distortion product otoacoustic emission (DPOAE) thresholds remained normal at P30 in ears with Huwe1 knockout at P1 (FIGS. 16E and F). Thus, the alterations in cochlear cells—development of extra inner hair cells that were fully innervated—had no obvious effects on function.

Example 18. Deletion of Sox2 has the Same Phenotype as Deletion of Huwe1

Deletion of Sox2 at E12 in earlier studies resulted in the abolition of hair cells, consistent with a role for Sox2 in the expression of Atoh1( ). We reasoned that its deletion at a later time point would prevent the Huwe1 induction and degradation of Atoh1. The phenotype obtained when Sox2 was deleted at E15.5 was, indeed, similar to the deletion of Huwe1; an extra row of inner hair cells could be seen in the knockout mice. An identical phenotype was seen after deletion at E17.5.

Example 19. Post-Translational Dampening of bHLH Transcription Factors by Sox2 Extends to Neurod1 and Neurog1

Since proneural bHLH transcription factors share homologies in sequence and regulation (see, e.g., Akagi et al., J Biol Chem 279, 28492-28498 (2004); Lo et al., Development 129, 1553-1567 (2002); Ross et al., Neuron 39, 13-25 (2003)), we asked whether other bHLH proneural transcription factors were regulated by Sox2 destabilization after initial upregulation, as we had observed for Atoh1. qPCR analysis showed that overexpression of Sox2 led to significant upregulation of all three tested bHLH transcription factors, Atoh1, Neurog1 and Neurod1, in HEK cells. Like Atoh1, Sox2 also downregulated Neurog1 and Neurod1 proteins post-translationally, and, again, proteasome inhibition rescued the level of each transcription factor after Sox2 overexpression.

REFERENCES

Abbott D W, Yang Y, Hutti J E, Madhavarapu S, Kelliher M A, Cantley L C (2007) Coordinated regulation of Toll-like receptor and NOD2 signaling by K63-linked polyubiquitin chains. Molecular and Cellular Biology 27:6012-6025.

Adhikary S, Marinoni F, Hock A, Hulleman E, Popov N, Beier R, Bernard S, Quarto M, Capra M, Goettig S, Kogel U, Scheffner M, Helin K, Eilers M (2005) The ubiquitin ligase HectH9 regulates transcriptional activation by Myc and is essential for tumor cell proliferation. Cell 123:409-421.

Adler H J, Raphael Y (1996) New hair cells arise from supporting cell conversion in the acoustically damaged chick inner ear. Neuroscience letters 205:17-20.

Barker N, van Es J, Kuipers J, Kujala P, van den Born M, Cozijnsen M, Haegebarth A, Korving J, Begthel H, Peters P (2007) Identification of stem cells in small intestine and colon by marker gene Lgr5. Nature 449:1003-1007.

Ben-Arie N, Bellen H J, Armstrong D L, McCall A E, Gordadze P R, Guo Q, Matzuk M M, Zoghbi H Y (1997) Math1 is essential for genesis of cerebellar granule neurons. Nature 390:169-172.

Ben-Arie N, Hassan B A, Bermingham N A, Malicki D M, Armstrong D, Matzuk M, Bellen H J, Zoghbi H Y (2000) Functional conservation of atonal and Math1 in the CNS and PNS. Development (Cambridge, England) 127:1039-1048.

Bermingham N A, Hassan B A, Price S D, Vollrath M A, Ben-Arie N, Eatock R A, Bellen H J, Lysakowski A, Zoghbi H Y (1999) Math1: an essential gene for the generation of inner ear hair cells. Science (New York, N.Y.) 284:1837-1841.

Bertrand N, Castro D, Guillemot F (2002) Proneural genes and the specification of neural cell types. Nature Reviews Neuroscience 3:517-530.

Bossuyt W, Kazanjian A, De Geest N, Van Kelst S, De Hertogh G, Geboes K, Boivin G P, Luciani J, Fuks F, Chuah M, VandenDriessche T, Marynen P, Cools J, Shroyer N F, Hassan B A (2009) Atonal homolog 1 is a tumor suppressor gene. PLoS biology 7:e39.

Bramhall N F, Shi F, Arnold K, Hochedlinger K, Edge A S B (2014) Lgr5-positive supporting cells generate new hair cells in the postnatal cochlea. Stem cell reports 2:311-322.

Brooker R, Hozumi K, Lewis J (2006) Notch ligands with contrasting functions: Jagged1 and Delta1 in the mouse inner ear. Development (Cambridge, England) 133:1277-1286.

Cafaro J, Lee G S, Stone J S (2007) Atoh1 expression defines activated progenitors and differentiating hair cells during avian hair cell regeneration. Developmental dynamics: an official publication of the American Association of Anatomists 236:156-170.

Cai T, Seymour M L, Zhang H, Pereira F A, Groves A K (2013) Conditional deletion of Atoh1 reveals distinct critical periods for survival and function of hair cells in the organ of Corti. The Journal of neuroscience: the official journal of the Society for Neuroscience 33:10110-10122.

Chen D, Kon N, Li M, Zhang W, Qin J, Gu W (2005) ARF-BP1/Mule is a critical mediator of the ARF tumor suppressor. Cell 121:1071-1083.

Chen P, Johnson J E, Zoghbi H Y, Segil N (2002) The role of Math1 in inner ear development: Uncoupling the establishment of the sensory primordium from hair cell fate determination. Development (Cambridge, England) 129:2495-2505.

Clevers H (2006) Wnt/beta-catenin signaling in development and disease. Cell 127:469-480.

Corwin J T, Cotanche D A (1988) Regeneration of sensory hair cells after acoustic trauma. Science (New York, NY) 240:1772-1774.

D'Arca D, Zhao X, Xu W, Ramirez-Martinez N C, Iavarone A, Lasorella A (2010) Huwe1 ubiquitin ligase is essential to synchronize neuronal and glial differentiation in the developing cerebellum. Proceedings of the National Academy of Sciences of the United States of America 107:5875-5880.

Davis A C (1983) Hearing disorders in the population: first phase findings of the MRC National Study of Hearing. Hearing science and hearing disorders 35.

de Groot R E A, Ganji R S, Bernatik O, Lloyd-Lewis B, Seipel K, Šedová K, Zdráhal Z, Dhople V M, Dale T C, Korswagen H C, Bryja V (2014) Huwe1-mediated ubiquitylation of dishevelled defines a negative feedback loop in the Wnt signaling pathway. Science signaling 7:ra26.

Deshaies R J, Joazeiro C A P (2009) RING domain E3 ubiquitin ligases. Annual review of biochemistry 78:399-434.

Eng J K, McCormack A L, Yates J R (1994) An approach to correlate tandem mass spectral data of peptides with amino acid sequences in a protein database. Journal of the American Society for Mass Spectrometry 5:976-989.

Flora A, Garcia J, Thaller C, Zoghbi H (2007) The E-protein Tcf4 interacts with Math1 to regulate differentiation of a specific subset of neuronal progenitors. Proceedings of the National Academy of Sciences 104:15382.

Flora A, Klisch T J, Schuster G, Zoghbi H Y (2009) Deletion of Atoh1 disrupts Sonic Hedgehog signaling in the developing cerebellum and prevents medulloblastoma. Science (New York, N.Y.) 326:1424-1427.

Forge A, Li L, Corwin J T, Nevill G (1993) Ultrastructural evidence for hair cell regeneration in the mammalian inner ear. Science (New York, NY) 259:1616-1619.

Fritzsch B (2003) Development of inner ear afferent connections: forming primary neurons and connecting them to the developing sensory epithelia. Brain research bulletin 60:423-433.

Gao D, Inuzuka H, Tan M-KM, Fukushima H, Locasale J W, Liu P, Wan L, Zhai B, Chin Y R, Shaik S, Lyssiotis C A, Gygi S P, Toker A, Cantley L C, Asara J M, Harper J W, Wei W (2011a) mTOR drives its own activation via SCF(βTrCP)-dependent degradation of the mTOR inhibitor DEPTOR. Molecular cell 44:290-303.

Gao S S, Xia A, Yuan T, Raphael P D, Shelton R L, Applegate B E, Oghalai J S (2011b) Quantitative imaging of cochlear soft tissues in wild-type and hearing-impaired transgenic mice by spectral domain optical coherence tomography. Optics express 19:15415-15428.

Gregorieff A, Clevers H (2005) Wnt signaling in the intestinal epithelium: from endoderm to cancer. Genes & development 19:877-890.

Gubbels S P, Woessner D W, Mitchell J C, Ricci A J, Brigande J V (2008) Functional auditory hair cells produced in the mammalian cochlea by in utero gene transfer. Nature 455:537-541.

Herold S, Hock A, Herkert B, Berns K, Mullenders J, Beijersbergen R, Bernards R, Eilers M (2008) Miz1 and HectH9 regulate the stability of the checkpoint protein, TopBP1. The EMBO Journal 27:2851-2861.

Hirabayashi Y, Itoh Y, Tabata H, Nakajima K, Akiyama T, Masuyama N, Gotoh Y (2004) The Wnt/beta-catenin pathway directs neuronal differentiation of cortical neural precursor cells. Development (Cambridge, England) 131:2791-2801.

Hu Z, Ulfendahl M (2006) Cell replacement therapy in the inner ear. Stem cells and development 15:449-459.

Hu Z, Andäng M, Ni D, Ulfendahl M (2005) Neural cograft stimulates the survival and differentiation of embryonic stem cells in the adult mammalian auditory system. Brain Research 1051:137-144.

Huang F, Zeng X, Kim W, Balasubramani M, Fortian A, Gygi S P, Yates N A, Sorkin A (2013) Lysine 63-linked polyubiquitination is required for EGF receptor degradation. Proceedings of the National Academy of Sciences of the United States of America 110:15722-15727.

Huibregtse J M, Scheffner M, Beaudenon S, Howley P M (1995) A family of proteins structurally and functionally related to the E6-AP ubiquitin-protein ligase. Proceedings of the National Academy of Sciences of the United States of America 92:5249.

Husseman J, Raphael Y (2009) Gene therapy in the inner ear using adenovirus vectors. Advances in oto-rhino-laryngology 66:37-51.

Ikeda F, Dikic I (2008) Atypical ubiquitin chains: new molecular signals. "Protein Modifications: Beyond the Usual Suspects" review series. EMBO Reports 9:536-542.

Incesulu A, Nadol J B (1998) Correlation of acoustic threshold measures and spiral ganglion cell survival in severe to profound sensorineural hearing loss: implications for cochlear implantation. The Annals of otology, rhinology, and laryngology 107:906-911.

Inoue S et al. (2013) Mule/Huwe1/Arf-B P1 suppresses Ras-driven tumorigenesis by preventing c-Myc/Miz1-mediated down-regulation of p21 and p15. Genes & development 27:1101-1114.

Inuzuka H, Shaik S, Onoyama I, Gao D, Tseng A, Maser R S, Zhai B, Wan L, Gutierrez A, Lau A W, Xiao Y, Christie A L, Aster J, Settleman J, Gygi S P, Kung A L, Look T, Nakayama K I, Depinho R A, Wei W (2012) SCFFBW7 regulates cellular apoptosis by targeting MCL1 for ubiquitylation and destruction. Nature 470:104-109.

Ivan M, Kondo K, Yang H, Kim W, Valiando J, Ohh M, Salic A, Asara J M, Lane W S, Kaelin W G (2001) HIFalpha targeted for VHL-mediated destruction by proline hydroxylation: implications for O2 sensing. Science (New York, NY) 292:464-468.

Izumikawa M, Minoda R, Kawamoto K, Abrashkin K A, Swiderski D L, Dolan D F, Brough D E, Raphael Y (2005) Auditory hair cell replacement and hearing improvement by Atoh1 gene therapy in deaf mammals. Nature Medicine 11:271-276.

Jaakkola P, Mole D R, Tian Y M, Wilson M I, Gielbert J, Gaskell S J, von Kriegsheim A, Hebestreit H F, Mukherji M, Schofield C J, Maxwell P H, Pugh C W, Ratcliffe P J (2001) Targeting of HIF-alpha to the von Hippel-Lindau ubiquitylation complex by O2-regulated prolyl hydroxylation. Science (New York, NY) 292:468-472.

Jarriault S, Brou C, Logeat F, Schroeter E H, Kopan R, Israel A (1995) Signalling downstream of activated mammalian Notch. Nature 377:355-358.

Jeon S-J, Oshima K, Heller S, Edge A S B (2007) Bone marrow mesenchymal stem cells are progenitors in vitro for inner ear hair cells. Molecular and cellular neurosciences 34:59-68.

Jeon S-J, Fujioka M, Kim S-C, Edge A S B (2011) Notch signaling alters sensory or neuronal cell fate specification of inner ear stem cells. The Journal of neuroscience: the official journal of the Society for Neuroscience 31:8351-8358.

Kawamoto K, Izumikawa M, Beyer L A, Atkin G M, Raphael Y (2009) Spontaneous hair cell regeneration in the mouse utricle following gentamicin ototoxicity. Hearing research 247:17-26.

Kelley M W (2006) Regulation of cell fate in the sensory epithelia of the inner ear. Nature Reviews Neuroscience 7:837-849.

Klisch T J, Xi Y, Flora A, Wang L, Li W, Zoghbi H Y (2011) In vivo Atoh1 targetome reveals how a proneural transcription factor regulates cerebellar development. Proceedings of the National Academy of Sciences of the United States of America.

Knippschild U, Kruger M, Richter J, Xu P, Garcia-Reyes B, Peifer C, Halekotte J, Bakulev V, Bischof J (2014) The CK1 Family: Contribution to Cellular Stress Response and Its Role in Carcinogenesis. Frontiers in oncology 4:96.

Kondo T, Matsuoka A J, Shimomura A, Koehler K R, Chan R J, Miller J M, Srour E F, Hashino E (2011) Wnt Signaling Promotes Neuronal Differentiation From Mesenchymal Stem Cells Through Activation of Tlx3. Stem cells (Dayton, Ohio).

Kurokawa M, Kim J, Geradts J, Matsuura K, Liu L, Ran X, Xia W, Ribar T J, Henao R, Dewhirst M W, Kim W-J, Lucas J E, Wang S, Spector N L, Kornbluth S (2013) A network of substrates of the E3 ubiquitin ligases MDM2 and HUWE1 control apoptosis independently of p53. Science signaling 6:ra32.

Lanford P J, Lan Y, Jiang R, Lindsell C, Weinmaster G, Gridley T, Kelley M W (1999) Notch signalling pathway mediates hair cell development in mammalian cochlea. Nature Genetics 21:289-292.

Latres E, Chiaur D S, Pagano M (1999) The human F box protein beta-Trcp associates with the Cul1/Skp1 complex and regulates the stability of beta-catenin. Oncogene 18:849-854.

Ledent V, Paquet O, Vervoort M (2002) Phylogenetic analysis of the human basic helix-loop-helix proteins. Genome biology 3:RESEARCH0030.

Lee J M, Lee J S, Kim H, Kim K, Park H, Kim J-Y, Lee S H, Kim I S, Kim J, Lee M, Chung C H, Seo S-B, Yoon J-B, Ko E, Noh D-Y, Kim K I, Kim K K, Baek S H (2012) EZH2 generates a methyl degron that is recognized by the DCAF1/DDB1/CUL4 E3 ubiquitin ligase complex. Molecular cell 48:572-586.

Lin V, Golub J S, Nguyen T B, Hume C R, Oesterle E C, Stone J S (2011) Inhibition of notch activity promotes nonmitotic regeneration of hair cells in the adult mouse utricles. The Journal of neuroscience: the official journal of the Society for Neuroscience 31:15329-15339.

Lo L C, Johnson J E, Wuenschell C W, Saito T, Anderson D J (1991) Mammalian achaete-scute homolog 1 is transiently expressed by spatially restricted subsets of early neuroepithelial and neural crest cells. Genes & development 5:1524-1537.

Ma E Y, Raible D W (2009) Signaling pathways regulating zebrafish lateral line development. Current biology: CB 19:R381-386.

Maksimovic S, Nakatani M, Baba Y, Nelson A M, Marshall K L, Wellnitz S A, Firozi P, Woo S-H, Ranade S, Patapoutian A, Lumpkin E A (2014) Epidermal Merkel cells are mechanosensory cells that tune mammalian touch receptors. Nature 509:617-621.

Markkanen E, van Loon B, Ferrari E, Parsons J L, Dianov G L, Hübscher U (2012) Regulation of oxidative DNA damage repair by DNA polymerase λ and MutYH by cross-talk of phosphorylation and ubiquitination. Proceedings of the National Academy of Sciences of the United States of America 109:437-442.

Meierhofer D, Wang X, Huang L, Kaiser P (2008) Quantitative analysis of global ubiquitination in HeLa cells by mass spectrometry. Journal of proteome research 7:4566-4576.

Miesegaes G R, Klisch T J, Thaller C, Ahmad K A, Atkinson R C, Zoghbi H Y (2009) Identification and subclassification of new Atoh1 derived cell populations during mouse spinal cord development. Developmental Biology 327:339-351.

Mizutari K, Fujioka M, Hosoya M, Bramhall N, Okano H J, Okano H, Edge A S B (2013) Notch inhibition induces cochlear hair cell regeneration and recovery of hearing after acoustic trauma. Neuron 77:58-69.

Morrison K M, Miesegaes G R, Lumpkin E A, Maricich S M (2009) Mammalian Merkel cells are descended from the epidermal lineage. Developmental Biology 336:76-83.

Murre C, McCaw P S, Vaessin H, Caudy M, Jan L Y, Jan Y N, Cabrera C V, Buskin J N, Hauschka S D, Lassar A B (1989) Interactions between heterologous helix-loop-helix proteins generate complexes that bind specifically to a common DNA sequence. Cell 58:537-544.

Naujokat C, Šarić T (2007) Concise review: role and function of the ubiquitin-proteasome system in mammalian stem and progenitor cells. Stem cells (Dayton, Ohio) 25:2408-2418.

Noy T, Suad O, Taglicht D, Ciechanover A (2012) HUWE1 ubiquitinates MyoD and targets it for proteasomal degradation. Biochemical and Biophysical Research Communications 418:408-413.

Ohyama T, Mohamed O A, Taketo M M, Dufort D, Groves A K (2006) Wnt signals mediate a fate decision between otic placode and epidermis. Development (Cambridge, England) 133:865-875.

Pan N, Jahan I, Kersigo J, Duncan J S, Kopecky B, Fritzsch B (2012) A novel Atoh1 "self-terminating" mouse model reveals the necessity of proper Atoh1 level and duration for hair cell differentiation and viability. PloS one 7:e30358.

Pandya R K, Partridge J R, Love K R, Schwartz T U, Ploegh H L (2010) A structural element within the HUWE1 HECT domain modulates self-ubiquitination and substrate ubiquitination activities. The Journal of biological chemistry 285:5664-5673.

Parker M, Brugeaud A, Edge A S B (2010) Primary culture and plasmid electroporation of the murine organ of Corti. Journal of Visualized Experiments.

Parker M A (2011) Biotechnology in the treatment of sensorineural hearing loss: foundations and future of hair cell regeneration. Journal of speech, language, and hearing research: JSLHR 54:1709-1731.

Parker M A, Cheng Y-f, Kinouchi H, Bieber R, Edge A S B (2014) An independent construct for conditional expression of atonal homolog-1. Human gene therapy methods 25:1-13.

Peng J, Schwartz D, Elias J E, Thoreen C C, Cheng D, Marsischky G, Roelofs J, Finley D, Gygi S P (2003) A proteomics approach to understanding protein ubiquitination. Nature Biotechnology 21:921-926.

Qyang Y, Martin-Puig S, Chiravuri M, Chen S, Xu H, Bu L, Jiang X, Lin L, Granger A, Moretti A, Caron L, Wu X, Clarke J, Taketo M M, Laugwitz K-L, Moon R T, Gruber P, Evans S M, Ding S, Chien K R (2007) The renewal and differentiation of Isl1+ cardiovascular progenitors are controlled by a Wnt/beta-catenin pathway. Cell stem cell 1:165-179.

Riccomagno M, Takada S, Epstein D (2005) Wnt-dependent regulation of inner ear morphogenesis is balanced by the opposing and supporting roles of Shh. Genes & development 19:1612-1623.

Roberson D W, Alosi J A, Cotanche D A (2004) Direct transdifferentiation gives rise to the earliest new hair cells in regenerating avian auditory epithelium. Journal of neuroscience research 78:461-471.

Ross S E, Greenberg M E, Stiles C D (2003) Basic helix-loop-helix factors in cortical development. Neuron 39:13-25.

Rotin D, Kumar S (2009) Physiological functions of the HECT family of ubiquitin ligases. Nature Reviews Molecular Cell Biology 10:398-409.

Scheffner M, Staub O (2007) HECT E3s and human disease. BMC biochemistry 8 Suppl 1:S6.

Schwarz S E, Rosa J L, Scheffner M (1998) Characterization of human hect domain family members and their interaction with UbcH5 and UbcH7. The Journal of biological chemistry 273:12148-12154.

Shi F, Kempfle J S, Edge A S B (2012) Wnt-responsive Lgr5-expressing stem cells are hair cell progenitors in the cochlea. The Journal of neuroscience: the official journal of the Society for Neuroscience 32:9639-9648.

Shi F, Cheng Y-f, Wang X L, Edge A S B (2010) Beta-catenin up-regulates Atoh1 expression in neural progenitor cells by interaction with an Atoh1 3' enhancer. The Journal of biological chemistry 285:392-400.

Shi F, Hu L, Jacques B E, Mulvaney J F, Dabdoub A, Edge A S B (2014) β-Catenin is required for hair-cell differentiation in the cochlea. The Journal of neuroscience: the official journal of the Society for Neuroscience 34:6470-6479.

Skowyra D, Craig K L, Tyers M, Elledge S J, Harper J W (1997) F-box proteins are receptors that recruit phosphorylated substrates to the SCF ubiquitin-ligase complex. Cell 91:209-219.

Sowa M E, Bennett E J, Gygi S P, Harper J W (2009) Defining the human deubiquitinating enzyme interaction landscape. Cell 138:389-403.

Spence J, Sadis S, Haas A L, Finley D (1995) A ubiquitin mutant with specific defects in DNA repair and multiubiquitination. Molecular and Cellular Biology 15:1265-1273.

Staecker H, Praetorius M, Baker K, Brough D E (2007) Vestibular hair cell regeneration and restoration of balance function induced by math1 gene transfer. Otology & neurotology 28:223-231.

Stevens C B, Davies A L, Battista S, Lewis J H, Fekete D M (2003) Forced activation of Wnt signaling alters morphogenesis and sensory organ identity in the chicken inner ear. Developmental Biology 261:149-164.

Stone J S, Cotanche D A (1994) Identification of the timing of S phase and the patterns of cell proliferation during hair cell regeneration in the chick cochlea. The Journal of Comparative Neurology 341:50-67.

Tai H-C, Schuman E M (2008) Ubiquitin, the proteasome and protein degradation in neuronal function and dysfunction. Nature Reviews Neuroscience 9:826-838.

Takebayashi S, Yamamoto N, Yabe D, Fukuda H, Kojima K, Ito J, Honjo T (2007) Multiple roles of Notch signaling in cochlear development. Developmental Biology 307:165-178.

Tan M-KM, Lim H-J, Bennett E J, Shi Y, Harper J W (2013) Parallel SCF adaptor capture proteomics reveals a role for SCFFBXL17 in NRF2 activation via BACH1 repressor turnover. Molecular cell 52:9-24.

Tiveron M C, Pattyn A, Hirsch M R, Brunet J F (2003) Role of Phox2b and Mash1 in the generation of the vestibular efferent nucleus. Developmental Biology 260:46-57.

Tsuchiya K, Nakamura T, Okamoto R, Kanai T, Watanabe M (2007) Reciprocal targeting of Hath1 and beta-catenin by Wnt glycogen synthase kinase 3beta in human colon cancer. Gastroenterology 132:208-220.

Varshavsky A (1991) Naming a targeting signal. Cell 64:13-15.

Wang X, Lu G, Li L, Yi J, Yan K, Wang Y, Zhu B, Kuang J, Lin M, Zhang S, Shao G (2013) HUWE1 interacts with BRCA1 and promotes its degradation in the ubiquitin-proteasome pathway. Biochemical and Biophysical Research Communications.

Warchol M E, Lambert P R, Goldstein B J, Forge A, Corwin J T (1993) Regenerative proliferation in inner ear sensory epithelia from adult guinea pigs and humans. Science (New York, NY) 259:1619-1622.

WHO In.

Woods C, Montcouquiol M, Kelley M W (2004) Math1 regulates development of the sensory epithelium in the mammalian cochlea. Nature Neuroscience 7:1310.

Wu G, Xu G, Schulman B A, Jeffrey P D, Harper J W, Pavletich N P (2003) Structure of a beta-TrCP1-Skp1-beta-catenin complex: destruction motif binding and lysine specificity of the SCF(beta-TrCP1) ubiquitin ligase. Molecular cell 11:1445-1456.

Yamamoto N, Tanigaki K, Tsuji M, Yabe D, Ito J, Honjo T (2006) Inhibition of Notch/RBP-J signaling induces hair cell formation in neonate mouse cochleas. Journal of Molecular Medicine 84:37-45.

Yang H, Xie X, Deng M, Chen X, Gan L (2010a) Generation and characterization of Atoh1-Cre knock-in mouse line. Genesis (New York, N.Y.: 2000) 48:407-413.

Yang Q, Bermingham N, Finegold M, Zoghbi H (2001) Requirement of Math1 for Secretory Cell Lineage Commitment in the Mouse Intestine. Science (New York, NY) 294:2155.

Yang Y, Do H, Tian X, Zhang C, Liu X, Dada L A, Sznajder J I, Liu J (2010b) E3 ubiquitin ligase Mule ubiquitinates Miz1 and is required for TNFalpha-induced JNK activation. Proceedings of the National Academy of Sciences of the United States of America 107:13444-13449.

Ye X, Nalepa G, Welcker M, Kessler B M, Spooner E, Qin J, Elledge S J, Clurman B E, Harper J W (2004) Recognition of phosphodegron motifs in human cyclin E by the SCF(Fbw7) ubiquitin ligase. The Journal of biological chemistry 279:50110-50119.

Zhang J, Kan S, Huang B, Hao Z, Mak T W, Zhong Q (2011) Mule determines the apoptotic response to HDAC inhibitors by targeted ubiquitination and destruction of HDAC2. Genes & development 25:2610-2618.

Zhao X, Heng JI-T, Guardavaccaro D, Jiang R, Pagano M, Guillemot F, Iavarone A, Lasorella A (2008) The HECT-domain ubiquitin ligase Huwe1 controls neural differentiation and proliferation by destabilizing the N-Myc oncoprotein. Nature Cell Biology 10:643-653.

Zhao X, D'Arca D, Lim W K, Brahmachary M, Carro M S, Ludwig T, Cardo C C, Guillemot F, Aldape K, Califano A, Iavarone A, Lasorella A (2009) The N-Myc-DLL3 cascade is suppressed by the ubiquitin ligase Huwe1 to inhibit proliferation and promote neurogenesis in the developing brain. Developmental cell 17:210-221.

Zheng J L, Gao W-Q (2000) Overexpression of Math1 induces robust production of extra hair cells in postnatal rat inner ears. Nature Neuroscience 3:580.

Zhong Q, Gao W, Du F, Wang X (2005) Mule/ARF-BP1, a BH3-only E3 ubiquitin ligase, catalyzes the polyubiquitination of Mcl-1 and regulates apoptosis. Cell 21:1085-1095.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An expression vector comprising a polynucleotide encoding a human Atoh1 variant polypeptide, wherein the human Atoh1 variant polypeptide is a long-lived human Atoh1 variant polypeptide comprising a mutation at the amino acid position corresponding to amino acid 334 of SEQ ID NO: 1, and wherein the long-lived human Atoh1 variant polypeptide is at least 95% identical to SEQ ID NO: 1.

2. The expression vector of claim 1, wherein the amino acid at the position corresponding to amino acid 334 of SEQ ID NO: 1 is not serine.

3. The expression vector of claim 1, wherein the long-lived human Atoh1 variant polypeptide comprises SEQ ID NO: 1 with a mutation of S334A.

4. The expression vector of claim 1, wherein the long-lived human Atoh1 variant polypeptide further comprises a mutation at the amino acid position corresponding to amino acid 331 of SEQ ID NO: 1.

5. The expression vector of claim 4, wherein the amino acid at the position corresponding to amino acid 331 of SEQ ID NO: 1 is not serine.

6. The expression vector of claim 1, wherein the long-lived human Atoh1 variant polypeptide comprises SEQ ID NO: 1 with mutations S331A/S334A.

7. The expression vector of claim 1, which is a viral vector.

8. The expression vector of claim 7, wherein the viral vector is selected from the group consisting of recombinant retrovirus, adenovirus, adeno-associated virus, and lentivirus.

9. An isolated nucleic acid molecule comprising a nucleotide sequence encoding a human Atoh1 variant polypeptide, wherein the human Atoh1 variant polypeptide is a long-lived human Atoh1 variant polypeptide comprising a mutation at the amino acid position corresponding to amino acid position 334 of SEQ ID NO: 1, and wherein the long-lived human Atoh1 variant polypeptide is at least 95% identical to SEQ ID NO: 1.

10. The isolated nucleic acid molecule of claim 9, wherein the long-lived human Atoh1 variant polypeptide comprises SEQ ID NO: 1 with a mutation of S334A.

11. The isolated nucleic acid molecule of claim 9, wherein the long-lived human Atoh1 variant polypeptide comprises SEQ ID NO: 1 with mutations S331A/S334A.

12. The isolated nucleic acid molecule of claim 9, wherein the nucleotide sequence further encodes a 5' untranslated region.

13. The isolated nucleic acid molecule of claim 9, which is at least 95% identical to SEQ ID NO: 2.

* * * * *

SEQUENCE LISTING

```
<160> NUMBER OF SEQ ID NOS: 16

<210> SEQ ID NO 1
<211> LENGTH: 354
<212> TYPE: PRT
<213> ORGANISM: Homo sapiens
<220> FEATURE:
<221> NAME/KEY: VARIANT
<222> LOCATION: 328, 331, 334
<223> OTHER INFORMATION: Xaa = Any Amino Acid

<400> SEQUENCE: 1

Met Ser Arg Leu Leu His Ala Glu Glu Trp Ala Glu Val Lys Glu Leu
1               5                   10                  15

Gly Asp His His Arg Gln Pro Gln Pro His His Leu Pro Gln Pro Pro
                20                  25                  30

Pro Pro Pro Gln Pro Pro Ala Thr Leu Gln Ala Arg Glu His Pro Val
            35                  40                  45

Tyr Pro Pro Glu Leu Ser Leu Leu Asp Ser Thr Asp Pro Arg Ala Trp
        50                  55                  60

Leu Ala Pro Thr Leu Gln Gly Ile Cys Thr Ala Arg Ala Ala Gln Tyr
65                  70                  75                  80

Leu Leu His Ser Pro Glu Leu Gly Ala Ser Glu Ala Ala Ala Pro Arg
                85                  90                  95
```

```
Asp Glu Val Asp Gly Arg Gly Glu Leu Val Arg Arg Ser Ser Gly Gly
            100                 105                 110

Ala Ser Ser Ser Lys Ser Pro Gly Pro Val Lys Val Arg Glu Gln Leu
            115                 120                 125

Cys Lys Leu Lys Gly Gly Val Val Val Asp Glu Leu Gly Cys Ser Arg
            130                 135                 140

Gln Arg Ala Pro Ser Ser Lys Gln Val Asn Gly Val Gln Lys Gln Arg
145                 150                 155                 160

Arg Leu Ala Ala Asn Ala Arg Glu Arg Arg Arg Met His Gly Leu Asn
                165                 170                 175

His Ala Phe Asp Gln Leu Arg Asn Val Ile Pro Ser Phe Asn Asn Asp
            180                 185                 190

Lys Lys Leu Ser Lys Tyr Glu Thr Leu Gln Met Ala Gln Ile Tyr Ile
            195                 200                 205

Asn Ala Leu Ser Glu Leu Leu Gln Thr Pro Ser Gly Gly Glu Gln Pro
            210                 215                 220

Pro Pro Pro Pro Ala Ser Cys Lys Ser Asp His His His Leu Arg Thr
225                 230                 235                 240

Ala Ala Ser Tyr Glu Gly Gly Ala Gly Asn Ala Thr Ala Ala Gly Ala
                245                 250                 255

Gln Gln Ala Ser Gly Gly Ser Gln Arg Pro Thr Pro Pro Gly Ser Cys
            260                 265                 270

Arg Thr Arg Phe Ser Ala Pro Ala Ser Ala Gly Gly Tyr Ser Val Gln
            275                 280                 285

Leu Asp Ala Leu His Phe Ser Thr Phe Glu Asp Ser Ala Leu Thr Ala
            290                 295                 300

Met Met Ala Gln Lys Asn Leu Ser Pro Ser Leu Pro Gly Ser Ile Leu
305                 310                 315                 320

Gln Pro Val Gln Glu Glu Asn Xaa Lys Thr Xaa Pro Arg Xaa His Arg
                325                 330                 335

Ser Asp Gly Glu Phe Ser Pro His Ser His Tyr Ser Asp Ser Asp Glu
            340                 345                 350

Ala Ser
```

<210> SEQ ID NO 2
<211> LENGTH: 1065
<212> TYPE: DNA
<213> ORGANISM: Homo sapiens
<220> FEATURE:
<221> NAME/KEY: misc_feature
<222> LOCATION: 982, 983, 984, 991, 992, 993, 1000, 1001, 1002
<223> OTHER INFORMATION: n = A, T, C or G

<400> SEQUENCE: 2

```
atgtcccgcc tgctgcatgc agaagagtgg gctgaagtga aggagttggg agaccaccat      60
cgccagcccc agccgcatca tctcccgcaa ccgccgccgc cgccgcagcc acctgcaact     120
ttgcaggcga gagagcatcc cgtctacccg cctgagctgt ccctcctgga cagcaccgac     180
ccacgcgcct ggctggctcc cactttgcag ggcatctgca cggcacgcgc cgcccagtat     240
ttgctacatt ccccggagct gggtgcctca gaggccgctg cgccccggga cgaggtggac     300
ggccgggggg agctggtaag gaggagcagc ggcggtgcca gcagcagcaa gagccccggg     360
ccggtgaaag tgcgggaaca gctgtgcaag ctgaaaggcg gggtggtggt agacgagctg     420
ggctgcagcc gccaacgggc cccttccagc aaacaggtga atggggtgca gaagcagaga     480
```

-continued

```
cggctagcag ccaacgccag ggagcggcgc aggatgcatg ggctgaacca cgccttcgac      540
cagctgcgca atgttatccc gtcgttcaac aacgacaaga agctgtccaa atatgagacc      600
ctgcagatgg cccaaatcta catcaacgcc ttgtccgagc tgctacaaac gcccagcgga      660
ggggaacagc caccgccgcc tccagcctcc tgcaaaagcg accaccacca ccttcgcacc      720
gcggcctcct atgaaggggg cgcgggcaac gcgaccgcag ctggggctca gcaggcttcc      780
ggagggagcc agcggccgac cccgcccggg agttgccgga ctcgcttctc agccccagct      840
tctgcgggag ggtactcggt gcagctggac gctctgcact tctcgacttt cgaggacagc      900
gccctgacag cgatgatggc gcaaaagaat ttgtctcctt ctctccccgg gagcatcttg      960
cagccagtgc aggaggaaaa cnnnaaaact nnncctcggn nncacagaag cgacgggaa     1020 ttttcccccc attcccatta cagtgactcg gatgaggcaa gttag                    1065
```

```
<210> SEQ ID NO 3
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 3
gattacaagg atgacga                                                    17

<210> SEQ ID NO 4
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 4
tgggcggcat ggtgcaagtt                                                 20

<210> SEQ ID NO 5
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 5
cggtgctaac cagcgttttc                                                 20

<210> SEQ ID NO 6
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 6
gtatggtcat gattgagtgc ttggaact                                        28

<210> SEQ ID NO 7
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 7
tatacctgaa cacatgggca tatacat                                         27
```

```
<210> SEQ ID NO 8
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 8
gattacaagg atgacga                                                      17

<210> SEQ ID NO 9
<211> LENGTH: 56
<212> TYPE: PRT
<213> ORGANISM: Artificial Sequence
<220> FEATURE:
<223> OTHER INFORMATION: consensus of C-terminus of Atoh1 (area 4)

<400> SEQUENCE: 9

Asp Ser Ala Leu Thr Ala Met Met Ala Gln Lys Asn Leu Ser Pro Ser
1               5                   10                  15

Leu Pro Gly Gly Ile Leu Gln Pro Val Gln Glu Glu Asn Ser Lys Thr
            20                  25                  30

Ser Pro Arg Ser His Arg Ser Asp Gly Glu Phe Ser Pro His Ser His
        35                  40                  45

Tyr Ser Asp Ser Asp Glu Ala Ser
    50                  55

<210> SEQ ID NO 10
<211> LENGTH: 56
<212> TYPE: PRT
<213> ORGANISM: Mus sp.

<400> SEQUENCE: 10

Asp Arg Ala Leu Thr Ala Met Met Ala Gln Lys Asp Leu Ser Pro Ser
1               5                   10                  15

Leu Pro Gly Gly Ile Leu Gln Pro Val Gln Glu Asp Asn Ser Lys Thr
            20                  25                  30

Ser Pro Arg Ser His Arg Ser Asp Gly Glu Phe Ser Pro His Ser His
        35                  40                  45

Tyr Ser Asp Ser Asp Glu Ala Ser
    50                  55

<210> SEQ ID NO 11
<211> LENGTH: 56
<212> TYPE: PRT
<213> ORGANISM: Homo sp.

<400> SEQUENCE: 11

Asp Ser Ala Leu Thr Ala Met Met Ala Gln Lys Asn Leu Ser Pro Ser
1               5                   10                  15

Leu Pro Gly Ser Ile Leu Gln Pro Val Gln Glu Glu Asn Ser Lys Thr
            20                  25                  30

Ser Pro Arg Ser His Arg Ser Asp Gly Glu Phe Ser Pro His Ser His
        35                  40                  45

Tyr Ser Asp Ser Asp Glu Ala Ser
    50                  55

<210> SEQ ID NO 12
<211> LENGTH: 56
<212> TYPE: PRT
```

-continued

```
<213> ORGANISM: Pan sp.

<400> SEQUENCE: 12

Asp Ser Ala Leu Thr Ala Met Met Ala Gln Lys Asn Leu Ser Pro Ser
1               5                   10                  15

Leu Pro Gly Ser Ile Leu Gln Pro Val Gln Glu Glu Asn Ser Lys Thr
            20                  25                  30

Ser Pro Arg Ser His Arg Ser Asp Gly Glu Phe Ser Pro His Ser His
        35                  40                  45

Tyr Ser Asp Ser Asp Glu Ala Ser
    50                  55

<210> SEQ ID NO 13
<211> LENGTH: 56
<212> TYPE: PRT
<213> ORGANISM: Rattus sp.

<400> SEQUENCE: 13

Asp Arg Ala Leu Thr Ala Met Met Ala Gln Lys Asp Leu Ser Pro Ser
1               5                   10                  15

Leu Pro Gly Gly Ile Leu Gln Pro Val Pro Glu Asp Ser Ser Lys Thr
            20                  25                  30

Ser Pro Arg Ser His Arg Ser Asp Gly Glu Phe Ser Pro His Ser His
        35                  40                  45

Tyr Ser Asp Ser Asp Glu Ala Ser
    50                  55

<210> SEQ ID NO 14
<211> LENGTH: 56
<212> TYPE: PRT
<213> ORGANISM: Bos sp.

<400> SEQUENCE: 14

Asp Ser Ala Leu Thr Ala Met Met Ala Gln Lys Asn Leu Ser Pro Ser
1               5                   10                  15

Leu Pro Gly Gly Ile Leu Gln Pro Val Gln Glu Glu Ser Ser Lys Thr
            20                  25                  30

Ser Pro Arg Ser His Arg Ser Asp Gly Glu Phe Ser Pro His Ser His
        35                  40                  45

Tyr Ser Asp Ser Asp Glu Ala Ser
    50                  55

<210> SEQ ID NO 15
<211> LENGTH: 48
<212> TYPE: PRT
<213> ORGANISM: Gallus sp.

<400> SEQUENCE: 15

Ala Gln Lys Ala Pro Ser Pro Ala Leu Leu Leu Gly Pro Pro Ala Pro
1               5                   10                  15

Gln Gln Pro Glu Arg Ser Lys Ala Ser Pro Arg Ser His Arg Ser Asp
            20                  25                  30

Gly Glu Phe Ser Pro Arg Ser His Tyr Ser Asp Ser Asp Glu Ala Ser
        35                  40                  45

<210> SEQ ID NO 16
<211> LENGTH: 38
<212> TYPE: PRT
<213> ORGANISM: Danio sp.
```

```
<400> SEQUENCE: 16

Glu Gln Asp Leu Gln Ser Pro Ser Gly Thr Ser Lys Ser Gly Ser Glu
1               5               10              15

Ala Ser Lys Asp Ser Pro Arg Ser Asn Arg Ser Asp Gly Glu Val Leu
            20              25              30

Ala Ser Leu Lys Cys Glu
        35
```